US012698269B2

(12) United States Patent
Fujita et al.

(10) Patent No.: US 12,698,269 B2
(45) Date of Patent: Aug. 4, 2026

(54) 1-ARYLTETRAHYDROPYRIDAZINE-3,5-DIONE DERIVATIVE OR SALT THEREOF AND INSECTICIDAL AGENT CONTAINING THE COMPOUND AND METHOD FOR USING SAME

(71) Applicant: NIHON NOHYAKU CO., LTD., Tokyo (JP)

(72) Inventors: Naoya Fujita, Kawachinagano (JP); Ryosuke Tanaka, Kawachinagano (JP); Ikki Yonemura, Kawachinagano (JP); Keisuke Mitsugi, Kawachinagano (JP); Hinoki Oikawa, Kawachinagano (JP); Taiki Yokoi, Kawachinagano (JP); Takayuki Yamada, Kawachinagano (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 160 days.

(21) Appl. No.: 18/850,816

(22) PCT Filed: Mar. 23, 2023

(86) PCT No.: PCT/JP2023/011457
§ 371 (c)(1),
(2) Date: Sep. 25, 2024

(87) PCT Pub. No.: WO2023/190015
PCT Pub. Date: Oct. 5, 2023

(65) Prior Publication Data

US 2025/0223275 A1 Jul. 10, 2025

(30) Foreign Application Priority Data

Mar. 28, 2022 (JP) ................................ 2022-051061

(51) Int. Cl.

| | |
|---|---|
| ***C07D 401/04*** | (2006.01) |
| ***A01N 43/58*** | (2006.01) |
| ***A01N 47/38*** | (2006.01) |
| ***A01P 7/04*** | (2006.01) |

(52) U.S. Cl.
CPC .......... *C07D 401/04* (2013.01); *A01N 43/58* (2013.01); *A01N 47/38* (2013.01); *A01P 7/04* (2021.08)

(58) Field of Classification Search
CPC ....... C07D 401/04; A01N 43/58; A01N 47/38
See application file for complete search history.

(56) References Cited

U.S. PATENT DOCUMENTS

2023/0303522 A1 9/2023 Tanaka et al.

FOREIGN PATENT DOCUMENTS

WO WO-2021261563 A1 * 12/2021 .......... C07D 413/12

OTHER PUBLICATIONS

International Preliminary Report on Patentability for International Application No. PCT/JP2023/011457, dated Dec. 25, 2023, with English translation.
International Search Report for International Application No. PCT/JP2023/011457, dated Jun. 6, 2023, with English translation.
Extended European Search Report for European Application No. 23780026.3, dated Mar. 3, 2026.

* cited by examiner

*Primary Examiner* — Andrew S Rosenthal
(74) *Attorney, Agent, or Firm* — Birch, Stewart, Kolasch & Birch, LLP

(57) ABSTRACT

For example, in agricultural and horticultural crop production, pests, etc. still cause heavy damage, and there is a demand for the development of novel agricultural and horticultural insecticidal agents due to factors such as the emergence of pests resistant to existing drugs.
The present invention has found that a compound represented by the general formula (1):

[Formula 1]

(1)

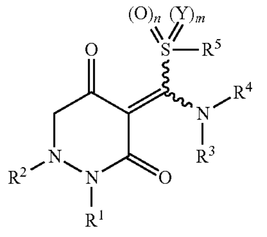

wherein $R^1$ represents an alkoxycarbonyl group or the like, $R^2$ represents a substituted phenyl group or the like, $R^3$ represents a hydrogen atom or the like, $R^4$ represents a substituted phenyl group or the like, $R^5$ represents an alkyl group or the like, Y represents an oxygen atom or the like and m and n each represent 0 or 1, or a salt thereof exhibits a high insecticidal effect on pests, etc. in the agricultural and horticultural field, and provides an agricultural and horticultural insecticidal agent comprising the same as an active ingredient and a method for using the same.

7 Claims, No Drawings

1-ARYLTETRAHYDROPYRIDAZINE-3,5-DIONE DERIVATIVE OR SALT THEREOF AND INSECTICIDAL AGENT CONTAINING THE COMPOUND AND METHOD FOR USING SAME

TECHNICAL FIELD

The present invention relates to a 1-aryltetrahydropyridazine-3,5-dione derivative or a salt thereof and an insecticidal agent containing the compound as an active ingredient and a method for using the same.

BACKGROUND ART

Patent Literature 1 has reported that certain tetrahydropyridazine-3,5-dione derivatives are useful as an insecticidal agent. However, the literature neither discloses nor suggests compounds having a sulfanyl-aminomethylidene structure of the invention of the present application.

CITATION LIST

Patent Literature

Patent Literature 1: International Publication No. WO 2021/261563

SUMMARY OF INVENTION

Technical Problem

For example, in agricultural and horticultural crop production, pests, etc. still cause heavy damage, and there is a demand for the development of novel insecticidal and acaricidal agents due to factors such as the emergence of pests resistant to existing drugs.

Solution to Problem

The present inventors have conducted diligent studies to develop novel insecticidal agents, particularly, agricultural and horticultural insecticidal agents, and consequently completed the present invention by finding that the compound represented by the general formula (1) of the present invention which has a sulfanyl-aminomethylidene structure in a 1-aryltetrahydropyridazine-3,5-dione skeleton, or a salt thereof exhibits an excellent effect as an insecticidal agent.

[1] A compound represented by the general formula (1) or a salt thereof:

[Formula 1]

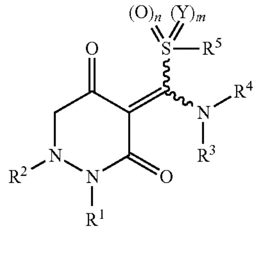

(1)

wherein $R^1$ represents (a1) a hydrogen atom;

(a2) a $(C_1-C_6)$ alkyl group;
(a3) a $(C_2-C_6)$ alkenyl group;
(a4) a $(C_2-C_6)$ alkynyl group;
(a5) a $(C_3-C_6)$ cycloalkyl group;
(a6) a halo $(C_1-C_6)$ alkyl group;
(a7) a halo $(C_3-C_6)$ cycloalkyl group;
(a8) a $(C_1-C_6)$ alkoxy group;
(a9) a substituted $(C_1-C_6)$ alkyl group having, on a chain, one to three substituents each independently selected from the group consisting of a cyano group, a $(C_1-C_6)$ alkoxy group and a $(C_3-C_6)$ cycloalkyl group;
(a10) a substituted $(C_3-C_6)$ cycloalkyl group having one to three substituents each independently selected from the group consisting of a cyano group, a $(C_1-C_6)$ alkyl group and a $(C_1-C_6)$ alkoxy group;
(a11) a $(C_1-C_6)$ alkylcarbonyl group;
(a12) a halo $(C_1-C_6)$ alkylcarbonyl group;
(a13) a $(C_3-C_6)$ cycloalkylcarbonyl group;
(a14) a $(C_1-C_6)$ alkoxy $(C_1-C_6)$ alkylcarbonyl group;
(a15) a $(C_1-C_6)$ alkylsulfanyl $(C_1-C_6)$ alkylcarbonyl group;
(a16) a phenylcarbonyl group;
(a17) a substituted phenylcarbonyl group having, on a ring, one to five substituents each independently selected from the group consisting of a halogen atom, a cyano group, a $(C_1-C_6)$ alkyl group and a $(C_1-C_6)$ alkoxy group;
(a18) a thienylcarbonyl group;
(a19) a substituted thienylcarbonyl group having, on a ring, one to three substituents each independently selected from the group consisting of a halogen atom, a cyano group, a $(C_1-C_6)$ alkyl group and a $(C_1-C_6)$ alkoxy group;
(a20) a thiazolylcarbonyl group;
(a21) a substituted thiazolylcarbonyl group having, on a ring, one or two substituents each independently selected from the group consisting of a halogen atom, a cyano group, a $(C_1-C_6)$ alkyl group and a $(C_1-C_6)$ alkoxy group;
(a22) a $(C_1-C_6)$ alkoxycarbonyl group;
(a23) a halo $(C_1-C_6)$ alkoxycarbonyl group;
(a24) a $(C_1-C_6)$ alkoxy $(C_1-C_6)$ alkoxycarbonyl group;
(a25) a $(C_1-C_6)$ alkylsulfanyl $(C_1-C_6)$ alkoxycarbonyl group;
(a26) a $(C_1-C_6)$ alkoxy $(C_1-C_6)$ alkoxy $(C_1-C_6)$ alkoxycarbonyl group;
(a27) a $(C_2-C_6)$ alkenyloxycarbonyl group;
(a28) a $(C_2-C_6)$ alkynyloxycarbonyl group;
(a29) a $(C_3-C_6)$ cycloalkoxycarbonyl group;
(a30) a phenyloxycarbonyl group;
(a31) a substituted phenyloxycarbonyl group having, on a ring, one to five substituents each independently selected from the group consisting of a halogen atom, a cyano group, a nitro group and a $(C_1-C_6)$ alkyl group;
(a32) a phenyl $(C_1-C_6)$ alkoxycarbonyl group;
(a33) a substituted phenyl $(C_1-C_6)$ alkoxycarbonyl group having, on a ring, one to five substituents each independently selected from the group consisting of a halogen atom, a cyano group, a nitro group and a $(C_1-C_6)$ alkyl group;
(a34) an aminocarbonyl group;
(a35) a N—$(C_1-C_6)$ alkylaminocarbonyl group;
(a36) a N,N-di-$(C_1-C_6)$ alkylaminocarbonyl group (wherein the $(C_1-C_6)$ alkyl moieties are the same as or different from each other);
(a37) a N-halo $(C_1-C_6)$ alkylaminocarbonyl group;
(a38) a N—$(C_2-C_6)$ alkenylaminocarbonyl group;

(a39) a N—($C_2$-$C_6$) alkynylaminocarbonyl group;
(a40) a N—($C_1$-$C_6$) alkyl-N—($C_2$-$C_6$) alkynylaminocarbonyl group;
(a41) a N—($C_3$-$C_6$) cycloalkylaminocarbonyl group;
(a42) a N—($C_1$-$C_6$) alkoxyaminocarbonyl group;
(a43) a N—($C_1$-$C_6$) alkoxy ($C_1$-$C_6$) alkylaminocarbonyl group;
(a44) a N—($C_1$-$C_6$) alkylsulfanyl ($C_1$-$C_6$) alkylaminocarbonyl group;
(a45) a N-phenyl ($C_1$-$C_6$) alkylaminocarbonyl group;
(a46) a N-substituted phenyl ($C_1$-$C_6$) alkylaminocarbonyl group having, on a ring, one to five substituents each independently selected from the group consisting of a halogen atom, a cyano group, a nitro group and a ($C_1$-$C_6$) alkyl group;
(a47) a pyrrolidinylcarbonyl group;
(a48) a N—($C_1$-$C_6$) alkylhydrazinocarbonyl group;
(a49) a N,N-di-($C_1$-$C_6$) alkylhydrazinocarbonyl group (wherein the ($C_1$-$C_6$) alkyl moieties are the same as or different from each other);
(a50) a N-phenylaminocarbonyl group;
(a51) a N-substituted phenylaminocarbonyl group having, on a ring, one to five substituents each independently selected from the group consisting of a halogen atom, a cyano group and a ($C_1$-$C_6$) alkyl group;
(a52) a ($C_1$-$C_6$) alkylsulfonyl group;
(a53) a halo ($C_1$-$C_6$) alkylsulfonyl group;
(a54) a N—($C_1$-$C_6$) alkylaminosulfonyl group;
(a55) a N-halo ($C_1$-$C_6$) alkylaminosulfonyl group;
(a56) a ($C_1$-$C_6$) alkylthiocarbonyl group;
(a57) a halo ($C_1$-$C_6$) alkylthiocarbonyl group;
(a58) a ($C_3$-$C_6$) cycloalkylthiocarbonyl group;
(a59) a ($C_1$-$C_6$) alkoxy ($C_1$-$C_6$) alkylthiocarbonyl group;
(a60) a ($C_1$-$C_6$) alkylthio($C_1$-$C_6$) alkylthiocarbonyl group;
(a61) a ($C_1$-$C_6$) alkoxythiocarbonyl group;
(a62) a halo ($C_1$-$C_6$) alkoxythiocarbonyl group;
(a63) a pyrrolidinylthiocarbonyl group;
(a64) a phenylthiocarbonyl group;
(a65) a substituted phenylthiocarbonyl group having, on a ring, one to five substituents each independently selected from the group consisting of a halogen atom, a cyano group and a ($C_1$-$C_6$) alkyl group;
(a66) a phenyloxythiocarbonyl group;
(a67) a phenyl ($C_1$-$C_6$) alkylthiocarbonyl group;
(a68) a substituted phenyl ($C_1$-$C_6$) alkylthiocarbonyl group having, on a ring, one to five substituents each independently selected from the group consisting of a halogen atom, a cyano group and a ($C_1$-$C_6$) alkyl group;
(a69) a N—($C_1$-$C_6$) alkylaminothiocarbonyl group;
(a70) a N-halo ($C_1$-$C_6$) alkylaminothiocarbonyl group;
(a71) a N,N-di-($C_1$-$C_6$) alkylaminothiocarbonyl group (wherein the ($C_1$-$C_6$) alkyl moieties are the same as or different from each other);
(a72) a N—($C_2$-$C_6$) alkenylaminothiocarbonyl group;
(a73) a N—($C_2$-$C_6$) alkynylaminothiocarbonyl group;
(a74) a N—($C_1$-$C_6$) alkyl-N—($C_2$-$C_6$) alkynylaminothiocarbonyl group;
(a75) a N—($C_1$-$C_6$) alkylsulfanyl ($C_1$-$C_6$) alkylaminothiocarbonyl group;
(a76) a N—($C_3$-$C_6$) cycloalkylaminothiocarbonyl group;
(a77) a N—($C_1$-$C_6$) alkoxy ($C_1$-$C_6$) alkylaminothiocarbonyl group;
(a78) a N-phenylaminothiocarbonyl group;
(a79) a substituted N-phenylaminothiocarbonyl group having, on a ring, one to five substituents each independently selected from the group consisting of a halogen atom, a cyano group and a ($C_1$-$C_6$) alkyl group;

(a80) a N-phenyl ($C_1$-$C_6$) alkylaminothiocarbonyl group;
(a81) a substituted N-phenyl ($C_1$-$C_6$) alkylaminothiocarbonyl group having, on a ring, one to five substituents each independently selected from the group consisting of a halogen atom, a cyano group and a ($C_1$-$C_6$) alkyl group;
(a82) a phenyl ($C_1$-$C_6$) alkyl group;
(a83) a substituted phenyl ($C_1$-$C_6$) alkyl group having, on a ring, one to five substituents each independently selected from the group consisting of a halogen atom, a ($C_1$-$C_6$) alkyl group, a halo ($C_1$-$C_6$) alkyl group and a ($C_1$-$C_6$) alkoxy group;
(a84) a thiazolyl ($C_1$-$C_6$) alkyl group;
(a85) a substituted thiazolyl ($C_1$-$C_6$) alkyl group having, on a ring, one or two substituents each independently selected from the group consisting of a halogen atom, a ($C_1$-$C_6$) alkyl group, a halo ($C_1$-$C_6$) alkyl group and a ($C_1$-$C_6$) alkoxy group;
(a86) a phenylsulfonyl group; or
(a87) a substituted phenylsulfonyl group having, on a ring, one to five substituents each independently selected from the group consisting of a halogen atom, a ($C_1$-$C_6$) alkyl group, a halo ($C_1$-$C_6$) alkyl group and a ($C_1$-$C_6$) alkoxy group, $R^2$ represents
(b1) an aryl group;
(b2) a substituted aryl group having, on a ring, one or more substituents each independently selected from substituent group A;
(b3) a 5- to 10-membered ring heterocyclic group; or
(b4) a substituted 5- to 10-membered ring heterocyclic group having, on a ring, one or more substituents each independently selected from substituent group A, $R^3$ represents
(c1) a hydrogen atom;
(c2) a ($C_1$-$C_6$) alkyl group;
(c3) a ($C_3$-$C_6$) cycloalkyl group;
(c4) a ($C_1$-$C_6$) alkoxy group;
(c5) a ($C_1$-$C_6$) alkylcarbonyl group; or
(c6) a ($C_1$-$C_6$) alkoxycarbonyl group, $R^4$ represents
(d1) a ($C_1$-$C_6$) alkyl group;
(d2) a ($C_2$-$C_6$) alkenyl group;
(d3) a ($C_2$-$C_6$) alkynyl group;
(d4) a ($C_3$-$C_6$) cycloalkyl group;
(d5) a halo ($C_1$-$C_6$) alkyl group;
(d6) a halo ($C_2$-$C_6$) alkenyl group;
(d7) a halo ($C_2$-$C_6$) alkynyl group;
(d8) a halo ($C_3$-$C_6$) cycloalkyl group;
(d9) a substituted ($C_1$-$C_6$) alkyl group having one to three substituents each independently selected from substituent group B;
(d10) a substituted ($C_3$-$C_6$) cycloalkyl group having, on a ring, one to three substituents each independently selected from substituent group C;
(d11) a N,N-di-($C_1$-$C_6$) alkylamino group (wherein the ($C_1$-$C_6$) alkyl moieties are the same as or different from each other);
(d12) a N—($C_1$-$C_6$) alkyl-N-phenylamino group;
(d13) a ($C_1$-$C_6$) alkylsulfonyl group;
(d14) a N—($C_1$-$C_6$) alkylaminosulfonyl group;
(d15) a piperidinyl group;
(d16) a morpholinyl group;
(d17) a phenyl group;
(d18) a substituted phenyl group having, on a ring, one to five substituents each independently selected from substituent group D;

(d19) a pyridyl group;
(d20) a substituted pyridyl group having, on a ring, one to four substituents each independently selected from substituent group D;
(d21) a pyridazinyl group;
(d22) a substituted pyridazinyl group having, on a ring, one to three substituents each independently selected from substituent group D;
(d23) a pyrimidinyl group;
(d24) a substituted pyrimidinyl group having, on a ring, one to three substituents each independently selected from substituent group D;
(d25) a pyrazinyl group;
(d26) a substituted pyrazinyl group having, on a ring, one to three substituents each independently selected from substituent group D;
(d27) a triazinyl group;
(d28) a substituted triazinyl group having, on a ring, one or two substituents each independently selected from substituent group D;
(d29) a furanyl group;
(d30) a substituted furanyl group having, on a ring, one to three substituents each independently selected from substituent group D;
(d31) an oxazolyl group;
(d32) a substituted oxazolyl group having, on a ring, one or two substituents each independently selected from substituent group D;
(d33) an isoxazolyl group;
(d34) a substituted isoxazolyl group having, on a ring, one or two substituents each independently selected from substituent group D;
(d35) a thienyl group;
(d36) a substituted thienyl group having, on a ring, one to three substituents each independently selected from substituent group D;
(d37) a thiazolyl group;
(d38) a substituted thiazolyl group having, on a ring, one or two substituents each independently selected from substituent group D;
(d39) an isothiazolyl group;
(d40) a substituted isothiazolyl group having, on a ring, one or two substituents each independently selected from substituent group D;
(d41) a thiadiazolyl group;
(d42) a substituted thiadiazolyl group having, on a ring, one substituent each independently selected from substituent group D;
(d43) a pyrazolyl group;
(d44) a substituted pyrazolyl group having, on a ring, one to three substituents each independently selected from substituent group D;
(d45) a triazolyl group;
(d46) a substituted triazolyl group having, on a ring, one or two substituents each independently selected from substituent group D;
(d47) a tetrazolyl group;
(d48) a substituted tetrazolyl group having, on a ring, one substituent each independently selected from substituent group D;
(d49) a benzoxazolyl group;
(d50) a substituted benzoxazolyl group having, on a ring, one to four substituents each independently selected from substituent group D;
(d51) a benzothiazolyl group;
(d52) a substituted benzothiazolyl group having, on a ring, one to four substituents each independently selected from substituent group D;
(d53) a quinolinyl group;
(d54) a substituted quinolinyl group having, on a ring, one to six substituents each independently selected from substituent group D;
(d55) a naphthyl group;
(d56) a substituted naphthyl group having, on a ring, one to seven substituents each independently selected from substituent group D;
(d57) a tetrahydronaphthyl group;
(d58) a substituted tetrahydronaphthyl group having, on a ring, one to ten substituents each independently selected from substituent group D;
(d59) a phenyl ($C_1$-$C_6$) alkyl group;
(d60) a substituted phenyl ($C_1$-$C_6$) alkyl group having, on a ring, one to five substituents each independently selected from substituent group D;
(d61) a pyridyl ($C_1$-$C_6$) alkyl group;
(d62) a substituted pyridyl ($C_1$-$C_6$) alkyl group having, on a ring, one to four substituents each independently selected from substituent group D;
(d63) a pyrazinyl ($C_1$-$C_6$) alkyl group;
(d64) a substituted pyrazinyl ($C_1$-$C_6$) alkyl group having, on a ring, one to three substituents each independently selected from substituent group D;
(d65) a pyrimidinyl ($C_1$-$C_6$) alkyl group;
(d66) a substituted pyrimidinyl ($C_1$-$C_6$) alkyl group having, on a ring, one to three substituents each independently selected from substituent group D;
(d67) a furanyl ($C_1$-$C_6$) alkyl group;
(d68) a substituted furanyl ($C_1$-$C_6$) alkyl group having, on a ring, one to three substituents each independently selected from substituent group D;
(d69) a thienyl ($C_1$-$C_6$) alkyl group; or
(d70) a substituted thienyl ($C_1$-$C_6$) alkyl group having, on a ring, one to three substituents each independently selected from substituent group D, $R^3$ and $R^4$ are optionally bonded to each other to form a ring, $R^5$ represents
(e1) a ($C_1$-$C_6$) alkyl group;
(e2) a ($C_2$-$C_6$) alkenyl group;
(e3) a ($C_2$-$C_6$) alkynyl group;
(e4) a ($C_3$-$C_6$) cycloalkyl group;
(e5) a halo ($C_1$-$C_6$) alkyl group;
(e6) a halo ($C_2$-$C_6$) alkenyl group;
(e7) a halo ($C_2$-$C_6$) alkynyl group;
(e8) a halo ($C_3$-$C_6$) cycloalkyl group;
(e9) a substituted ($C_1$-$C_6$) alkyl group having, on a chain, one to three substituents each independently selected from the group consisting of a cyano group, a ($C_1$-$C_6$) alkoxy group, a ($C_3$-$C_6$) cycloalkyl group, a ($C_1$-$C_6$) alkylcarbonyl group, a ($C_3$-$C_6$) cycloalkylcarbonyl group, a phenylcarbonyl group, a ($C_1$-$C_6$) alkoxycarbonyl group, an aminocarbonyl group, a halo ($C_1$-$C_6$) alkylcarbonyl group, a ($C_1$-$C_6$) alkylsulfanyl group, a tri-($C_1$-$C_6$) alkylsilyl ($C_1$-$C_6$) alkoxy group (wherein the ($C_1$-$C_6$) alkyl groups are the same as or different from each other), and a tri-($C_1$-$C_6$) alkylsilyl group (wherein the ($C_1$-$C_6$) alkyl groups are the same as or different from each other);
(e10) a substituted ($C_3$-$C_6$) cycloalkyl group having one to three substituents each independently selected from the group consisting of a cyano group, a ($C_1$-$C_6$) alkyl group, and a ($C_1$-$C_6$) alkoxy group;

(e11) a phenyl ($C_1$-$C_6$) alkyl group;

(e12) a substituted phenyl ($C_1$-$C_6$) alkyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_3$-$C_6$) cycloalkyl group, a ($C_1$-$C_6$) alkoxycarbonyl group, a ($C_1$-$C_6$) alkylsulfanyl group, a ($C_1$-$C_6$) alkylsulfinyl group, a ($C_1$-$C_6$) alkylsulfonyl group, a halo ($C_1$-$C_6$) alkylsulfanyl group, a diphenylamino group, a phenoxy group, and a methylenedioxy group formed by two adjacent substituents together;

(e13) a pyridyl ($C_1$-$C_6$) alkyl group;

(e14) a substituted pyridyl ($C_1$-$C_6$) alkyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e15) a thiazolyl ($C_1$-$C_6$) alkyl group;

(e16) a substituted thiazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e17) an oxadiazolyl ($C_1$-$C_6$) alkyl group;

(e18) a substituted oxadiazolyl ($C_1$-$C_6$) alkyl group having a pyridyl group on a ring;

(e19) a naphthyl ($C_1$-$C_6$) alkyl group;

(e20) a substituted naphthyl ($C_1$-$C_6$) alkyl group having, on a ring, one to seven substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e21) a quinolinyl ($C_1$-$C_6$) alkyl group;

(e22) a substituted quinolinyl ($C_1$-$C_6$) alkyl group having, on a ring, one to six substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e23) a thienyl ($C_1$-$C_6$) alkyl group;

(e24) a substituted thienyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e25) a pyrazolyl ($C_1$-$C_6$) alkyl group;

(e26) a substituted pyrazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e27) an oxazolyl ($C_1$-$C_6$) alkyl group;

(e28) a substituted oxazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e29) an imidazolyl ($C_1$-$C_6$) alkyl group;

(e30) a substituted imidazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e31) a pyridyl group;

(e32) a substituted pyridyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e33) a phenyl group;

(e34) a substituted phenyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e35) a ($C_1$-$C_6$) alkylcarbonyl group; or (e36) a hydrogen atom, $R^3$ and $R^5$ are optionally bonded to each other to form a 5- or 6-membered ring, Y represents an oxygen atom or $NR^6$ (wherein $R^6$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, a halo ($C_1$-$C_6$) alkylcarbonyl group, a ($C_1$-$C_6$) alkoxycarbonyl group, a phenylsulfonyl group, or a phenylsulfonyl group having, on a ring, one to five substituents each independently selected from the group consisting of a halogen atom, a cyano group, and a ($C_1$-$C_6$) alkyl group), m represents 0 or 1, n represents 0 or 1, substituent group A consists of (f1) a halogen atom;

(f2) a cyano group;

(f3) a nitro group;

(f4) a hydroxyl group;

(f5) a carboxyl group;

(f6) a ($C_1$-$C_6$) alkyl group;

(f7) a ($C_2$-$C_6$) alkenyl group;

(f8) a ($C_2$-$C_6$) alkynyl group;

(f9) a ($C_1$-$C_6$) alkoxy group;

(f10) a ($C_3$-$C_6$) cycloalkyl group;

(f11) a ($C_1$-$C_6$) alkylsulfanyl group;

(f12) a ($C_1$-$C_6$) alkylsulfinyl group;

(f13) a ($C_1$-$C_6$) alkylsulfonyl group;

(f14) a halo ($C_1$-$C_6$) alkyl group;

(f15) a halo ($C_2$-$C_6$) alkenyl group;

(f16) a halo ($C_2$-$C_6$) alkynyl group;

(f17) a halo ($C_1$-$C_6$) alkoxy group;

(f18) a halo ($C_3$-$C_6$) cycloalkyl group;

(f19) a halo ($C_1$-$C_6$) alkylsulfanyl group;

(f20) a halo ($C_1$-$C_6$) alkylsulfinyl group;

(f21) a halo ($C_1$-$C_6$) alkylsulfonyl group;

(f22) a N,N-di-($C_1$-$C_6$) alkylaminosulfonyl group (wherein the ($C_1$-$C_6$) alkyl moieties are the same as or different from each other);
(f23) a substituted ($C_3$-$C_6$) cycloalkyl group having, on a ring, one to three substituents each independently selected from the group consisting of a halogen atom, a cyano group, a ($C_1$-$C_6$) alkyl group, a ($C_1$-$C_6$) alkoxy group and a ($C_1$-$C_6$) alkylcarbonyl group;
(f24) a $SF_5$ group;
(f25) a ($C_1$-$C_6$) alkoxy ($C_1$-$C_6$) alkyl group;
(f26) a ($C_1$-$C_6$) alkoxy ($C_1$-$C_6$) alkoxy group;
(f27) a ($C_1$-$C_6$) alkylcarbonylamino group;
(f28) a halo ($C_1$-$C_6$) alkylcarbonylamino group;
(f29) a ($C_1$-$C_6$) alkylsulfonylamino group;
(f30) a halo ($C_1$-$C_6$) alkylsulfonylamino group;
(f31) a ($C_1$-$C_6$) alkoxycarbonyl group;
(f32) a methylenedioxy group formed by two adjacent substituents together and optionally substituted by one or two substituents each selected from the group consisting of a halogen atom, a phenyl group and a ($C_1$-$C_6$) alkyl group;
(f33) a ($C_1$-$C_6$) alkylaminocarbonyl group;
(f34) a N-halo ($C_1$-$C_6$) alkylaminocarbonyl group;
(f35) a furanyl group;
(f36) a substituted furanyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f37) an oxazolyl group;
(f38) a substituted oxazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f39) an isoxazolyl group;
(f40) a substituted isoxazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f41) an oxadiazolyl group;
(f42) a substituted oxadiazolyl group having, on a ring, one substituent each independently selected from the group consisting of a halogen atom, a cyano group, a ($C_1$-$C_6$) alkyl group, a ($C_1$-$C_6$) alkoxy group, a ($C_3$-$C_6$) cycloalkyl group, a halo ($C_1$-$C_6$) alkyl group and a halo ($C_1$-$C_6$) alkoxy group;
(f43) a thienyl group;
(f44) a substituted thienyl group having, on a ring, one to three substituents each independently selected from the group consisting of a halogen atom, a cyano group, a ($C_1$-$C_6$) alkyl group, a ($C_1$-$C_6$) alkoxy group, a ($C_3$-$C_6$) cycloalkyl group, a halo ($C_1$-$C_6$) alkyl group and a halo ($C_1$-$C_6$) alkoxy group;
(f45) a thiazolyl group;
(f46) a substituted thiazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f47) an isothiazolyl group;
(f48) a substituted isothiazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f49) a thiadiazolyl group;
(f50) a substituted thiadiazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f51) a pyrrolyl group;
(f52) a substituted pyrrolyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f53) a pyrazolyl group;
(f54) a substituted pyrazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f55) an imidazolyl group;
(f56) a substituted imidazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f57) a triazolyl group;
(f58) a substituted triazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f59) a tetrazolyl group;
(f60) a substituted tetrazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f61) an oxazolinyl group;
(f62) a substituted oxazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f63) a thiazolinyl group;
(f64) a substituted thiazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f65) an isoxazolinyl group;
(f66) a substituted isoxazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f67) an isothiazolinyl group;
(f68) a substituted isothiazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f69) a pyrrolidinyl group;

(f70) a substituted pyrrolidinyl group having, on a ring, one to four substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f71) an imidazolinyl group;
(f72) a substituted imidazolinyl group having, on a ring, one to four substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f73) a phenyl group;
(f74) a substituted phenyl group having, on a ring, one to five substituents each independently selected from the group consisting of a halogen atom, a cyano group, a $(C_1-C_6)$ alkyl group, a $(C_1-C_6)$ alkoxy group, a $(C_3-C_6)$ cycloalkyl group, a halo $(C_1-C_6)$ alkyl group and a halo $(C_1-C_6)$ alkoxy group;
(f75) a pyridyl group;
(f76) a substituted pyridyl group having, on a ring, one to four substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f77) a pyridazinyl group;
(f78) a substituted pyridazinyl group having, on a ring, one to three substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f79) a pyrimidinyl group;
(f80) a substituted pyrimidinyl group having, on a ring, one to three substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f81) a pyrazinyl group;
(f82) a substituted pyrazinyl group having, on a ring, one to three substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f83) a triazinyl group;
(f84) a substituted triazinyl group having, on a ring, one or two substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f85) a dihydrofuranyl group;
(f86) a dihydropyranyl group;
(f87) a phenyloxy group;
(f88) a substituted phenyloxy group having, on a ring, one to five substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f89) a phenyl $(C_1-C_6)$ alkoxy group;
(f90) a substituted phenyl $(C_1-C_6)$ alkoxy group having, on a ring, one to five substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f91) a phenyl $(C_1-C_6)$ alkylsulfanyl group;
(f92) a substituted phenyl $(C_1-C_6)$ alkylsulfanyl group having, on a ring, one to five substituents each independently selected from the group consisting of a halogen atom, a cyano group, a $(C_1-C_6)$ alkyl group, a $(C_1-C_6)$ alkoxy group, a halo $(C_1-C_6)$ alkyl group and a halo $(C_1-C_6)$ alkoxy group;
(f93) a $R^6—(R^7—N═)O═S$ group (wherein $R^6$ represents a $(C_1-C_6)$ alkyl group, a $(C_3-C_6)$ cycloalkyl group, a halo $(C_1-C_6)$ alkyl group, or $(C_1-C_6)$ alkoxy $(C_1-C_6)$ alkyl group, and $R^7$ represents a hydrogen atom, a cyano group, a $(C_1-C_6)$ alkyl group, a $(C_3-C_6)$ cycloalkyl group, a halo $(C_1-C_6)$ alkyl group, a $(C_1-C_6)$ alkylcarbonyl group, or a halo $(C_1-C_6)$ alkylcarbonyl group); and
(f94) an aminocarbonyl group,
substituent group B consists of
(g1) a cyano group;
(g2) a $(C_3-C_6)$ cycloalkyl group;
(g3) a $(C_1-C_6)$ alkoxy group;
(g4) a $(C_1-C_6)$ alkylsulfanyl group;
(g5) a $(C_1-C_6)$ alkylsulfinyl group;
(g6) a $(C_1-C_6)$ alkylsulfonyl group;
(g7) a halo $(C_3-C_6)$ cycloalkyl group;
(g8) a halo $(C_1-C_6)$ alkoxy group;
(g9) a halo $(C_1-C_6)$ alkylsulfanyl group;
(g10) a halo $(C_1-C_6)$ alkylsulfinyl group;
(g11) a halo $(C_1-C_6)$ alkylsulfonyl group;
(g12) a $(C_1-C_6)$ alkoxycarbonyl group;
(g13) an aminocarbonyl group; and
(g14) a phenylcarbonyl group,
substituent group C consists of
(h1) a cyano group;
(h2) a $(C_1-C_6)$ alkyl group;
(h3) a $(C_2-C_6)$ alkenyl group;
(h4) a $(C_2-C_6)$ alkynyl group;
(h5) a $(C_3-C_6)$ cycloalkyl group;
(h6) a $(C_1-C_6)$ alkoxy group;
(h7) a $(C_1-C_6)$ alkylsulfanyl group;
(h8) a $(C_1-C_6)$ alkylsulfinyl group;
(h9) a $(C_1-C_6)$ alkylsulfonyl group;
(h10) a halo $(C_1-C_6)$ alkyl group;
(h11) a halo $(C_3-C_6)$ cycloalkyl group;
(h12) a halo $(C_1-C_6)$ alkoxy group;
(h13) a halo $(C_1-C_6)$ alkylsulfanyl group;
(h14) a halo $(C_1-C_6)$ alkylsulfinyl group;
(h15) a halo $(C_1-C_6)$ alkylsulfonyl group;
(h16) an aminocarbonyl group; and
(h17) a phenyl group, and
substituent group D consists of
(i1) a halogen atom;
(i2) a cyano group;
(i3) a nitro group;
(i4) an amino group;
(i5) a hydroxyl group;
(i6) a carboxyl group;
(i7) a $(C_1-C_6)$ alkyl group;
(i8) a $(C_1-C_6)$ alkoxy group;
(i9) a $(C_3-C_6)$ cycloalkyl group;
(i10) a $(C_1-C_6)$ alkylsulfanyl group;
(i11) a $(C_1-C_6)$ alkylsulfinyl group;
(i12) a $(C_1-C_6)$ alkylsulfonyl group;
(i13) a halo $(C_1-C_6)$ alkyl group;
(i14) a halo $(C_3-C_6)$ alkoxy group;
(i15) a halo $(C_3-C_6)$ cycloalkyl group;
(i16) a halo $(C_1-C_6)$ alkylsulfanyl group;
(i17) a halo $(C_1-C_6)$ alkylsulfinyl group;

(i18) a halo ($C_1$-$C_6$) alkylsulfonyl group;

(i19) a ($C_1$-$C_6$) alkoxycarbonyl group;

(i20) a phenyl ($C_1$-$C_6$) alkoxycarbonyl group;

(i21) a ($C_1$-$C_6$) alkylaminocarbonyl group;

(i22) a N-halo ($C_1$-$C_6$) alkylaminocarbonyl group;

(i23) a phenyl group;

(i24) a substituted phenyl group having, on a ring, one to five substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group; and (i25) a methylenedioxy group formed by two adjacent substituents together and optionally substituted by one or two substituents each selected from the group consisting of a halogen atom, a phenyl group and a ($C_1$-$C_6$) alkyl group, on the proviso that in $R^2$, an adjacent atom of an atom bonded to the tetrahydropyridazine ring is not substituted by a ($C_1$-$C_6$) alkylsulfonyl group, a halo ($C_1$-$C_6$) alkylsulfonyl group, N—($C_1$-$C_6$) alkylaminosulfonyl group, N,N-di-($C_1$-$C_6$) alkylaminosulfonyl group, and $R^6$—($R^7$—N═)O═S group (wherein $R^6$ represents a ($C_1$-$C_6$) alkyl group, a ($C_3$-$C_6$) cycloalkyl group, a halo ($C_1$-$C_6$) alkyl group, or a ($C_1$-$C_6$) alkoxy ($C_1$-$C_6$) alkyl group, and $R^7$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, or a halo ($C_1$-$C_6$) alkylcarbonyl group),

[2] The compound according to [1] or a salt thereof, wherein $R^1$, $R^3$, $R^4$, $R^5$, Y, m, n, substituent groups A, B, C and D are as defined in [1], and $R^2$ is (b5) a phenyl group;

(b6) a substituted phenyl group having, on a ring, one to five substituents each independently selected from substituent group A;

(b7) a pyridyl group;

(b8) a substituted pyridyl group having, on a ring, one to four substituents each independently selected from substituent group A;

(b9) a pyridazinyl group;

(b10) a substituted pyridazinyl group having, on a ring, one to three substituents each independently selected from substituent group A;

(b11) a pyrimidinyl group;

(b12) a substituted pyrimidinyl group having, on a ring, one to three substituents each independently selected from substituent group A;

(b13) a pyrazinyl group;

(b14) a substituted pyrazinyl group having, on a ring, one to three substituents each independently selected from substituent group A;

(b15) a triazinyl group;

(b16) a substituted triazinyl group having, on a ring, one or two substituents each independently selected from substituent group A;

(b17) a 2-oxopyridyl group;

(b18) a substituted 2-oxopyridyl group having, on a ring, one to four substituents each independently selected from substituent group A;

(b19) a furanyl group;

(b20) a substituted furanyl group having, on a ring, one to three substituents each independently selected from substituent group A;

(b21) an oxazolyl group;

(b22) a substituted oxazolyl group having, on a ring, one or two substituents each independently selected from substituent group A;

(b23) an isoxazolyl group;

(b24) a substituted isoxazolyl group having, on a ring, one or two substituents each independently selected from substituent group A;

(b25) an oxadiazolyl group;

(b26) a substituted oxadiazolyl group having, on a ring, one substituent each independently selected from substituent group A;

(b27) a thienyl group;

(b28) a substituted thienyl group having, on a ring, one to three substituents each independently selected from substituent group A;

(b29) a thiazolyl group;

(b30) a substituted thiazolyl group having, on a ring, one or two substituents each independently selected from substituent group A;

(b31) an isothiazolyl group;

(b32) a substituted isothiazolyl group having, on a ring, one or two substituents each independently selected from substituent group A;

(b33) a thiadiazolyl group;

(b34) a substituted thiadiazolyl group having, on a ring, one substituent each independently selected from substituent group A;

(b35) a pyrrolyl group;

(b36) a substituted pyrrolyl group having, on a ring, one to four substituents each independently selected from substituent group A;

(b37) a pyrazolyl group;

(b38) a substituted pyrazolyl group having, on a ring, one to three substituents each independently selected from substituent group A;

(b39) an imidazolyl group;

(b40) a substituted imidazolyl group having, on a ring, one to three substituents each independently selected from substituent group A;

(b41) a triazolyl group;

(b42) a substituted triazolyl group having, on a ring, one or two substituents each independently selected from substituent group A;

(b43) a tetrazolyl group;

(b44) a substituted tetrazolyl group having, on a ring, one substituent each independently selected from substituent group A;

(b45) a benzofuranyl group;

(b46) a substituted benzofuranyl group having, on a ring, one to five substituents each independently selected from substituent group A;

(b47) a benzoxazolyl group;

(b48) a substituted benzoxazolyl group having, on a ring, one to four substituents each independently selected from substituent group A;

(b49) a benzisoxazolyl group;

(b50) a substituted benzisoxazolyl group having, on a ring, one to four substituents each independently selected from substituent group A;

(b51) a benzothienyl group;

(b52) a substituted benzothienyl group having, on a ring, one to five substituents each independently selected from substituent group A;

(b53) a benzothiazolyl group;

(b54) a substituted benzothiazolyl group having, on a ring, one to four substituents each independently selected from substituent group A;

(b55) a benzisothiazolyl group;
(b56) a substituted benzisothiazolyl group having, on a ring, one to four substituents each independently selected from substituent group A;
(b57) an indolyl group;
(b58) a substituted indolyl group having, on a ring, one to six substituents each independently selected from substituent group A;
(b59) an isoindolyl group;
(b60) a substituted isoindolyl group having, on a ring, one to six substituents each independently selected from substituent group A;
(b61) an indazolyl group;
(b62) a substituted indazolyl group having, on a ring, one to five substituents each independently selected from substituent group A;
(b63) a benzimidazolyl group;
(b64) a substituted benzimidazolyl group having, on a ring, one to five substituents each independently selected from substituent group A;
(b65) a benzotriazolyl group;
(b66) a substituted benzotriazolyl group having, on a ring, one to four substituents each independently selected from substituent group A;
(b67) a furopyridyl group;
(b68) a substituted furopyridyl group having, on a ring, one to four substituents each independently selected from substituent group A;
(b69) a thienopyridyl group;
(b70) a substituted thienopyridyl group having, on a ring, one to four substituents each independently selected from substituent group A;
(b71) a thiazolopyridyl group;
(b72) a substituted thiazolopyridyl group having, on a ring, one to four substituents each independently selected from substituent group A;
(b73) an imidazopyridyl group;
(b74) a substituted imidazopyridyl group having, on a ring, one to five substituents each independently selected from substituent group A;
(b75) an indolizinyl group;
(b76) a substituted indolizinyl group having, on a ring, one to six substituents each independently selected from substituent group A;
(b77) a pyrrolopyridyl group;
(b78) a substituted pyrrolopyridyl group having, on a ring, one to five substituents each independently selected from substituent group A;
(b79) a pyrrolopyrimidinyl group;
(b80) a substituted pyrrolopyrimidinyl group having, on a ring, one to five substituents each independently selected from substituent group A;
(b81) an oxazolopyridyl group;
(b82) a substituted oxazolopyridyl group having, on a ring, one to three substituents each independently selected from substituent group A;
(b83) an isoxazolopyridyl group;
(b84) a substituted isoxazolopyridyl group having, on a ring, one to three substituents each independently selected from substituent group A;
(b85) an isothiazolopyridyl group;
(b86) a substituted isothiazolopyridyl group having, on a ring, one to three substituents each independently selected from substituent group A;
(b87) an imidazopyrimidinyl group;
(b88) a substituted imidazopyrimidinyl group having, on a ring, one to five substituents each independently selected from substituent group A;
(b89) a pyrazolopyridyl group;
(b90) a substituted pyrazolopyridyl group having, on a ring, one to five substituents each independently selected from substituent group A;
(b91) a pyrazolopyrimidinyl group;
(b92) a substituted pyrazolopyrimidinyl group having, on a ring, one to five substituents each independently selected from substituent group A;
(b93) a triazolopyridyl group;
(b94) a substituted triazolopyridyl group having, on a ring, one to four substituents each independently selected from substituent group A;
(b95) a triazolopyrimidinyl group;
(b96) a substituted triazolopyrimidinyl group having, on a ring, one to four substituents each independently selected from substituent group A;
(b97) a quinoxalinyl group;
(b98) a substituted quinoxalinyl group having, on a ring, one to five substituents each independently selected from substituent group A;
(b99) a quinolinyl group;
(b100) a substituted quinolinyl group having, on a ring, one to six substituents each independently selected from substituent group A;
(b101) a naphthyl group;
(b102) a substituted naphthyl group having, on a ring, one to seven substituents each independently selected from substituent group A;
(b103) an isoquinolinyl group;
(b104) a substituted isoquinolinyl group having, on a ring, one to six substituents each independently selected from substituent group A;
(b105) a cinnolinyl group;
(b106) a substituted cinnolinyl group having, on a ring, one to five substituents each independently selected from substituent group A;
(b107) a phthalazinyl group;
(b108) a substituted phthalazinyl group having, on a ring, one to five substituents each independently selected from substituent group A;
(b109) a quinazolinyl group;
(b110) a substituted quinazolinyl group having, on a ring, one to five substituents each independently selected from substituent group A;
(b111) a naphthyridinyl group; or
(b112) a substituted naphthyridinyl group having, on a ring, one to five substituents each independently selected from substituent group A,

[3] The compound according to [1] or [2] or a salt thereof, wherein $R^1$ is
(a1) a hydrogen atom;
(a2) a $(C_1-C_6)$ alkyl group;
(a6) a halo $(C_1-C_6)$ alkyl group;
(a9) a substituted $(C_1-C_6)$ alkyl group having, on a chain, one to three substituents each independently selected from the group consisting of a cyano group, a $(C_1-C_6)$ alkoxy group and a $(C_3-C_6)$ cycloalkyl group;
(a11) a $(C_1-C_6)$ alkylcarbonyl group;
(a12) a halo $(C_1-C_6)$ alkylcarbonyl group;
(a13) a $(C_3-C_6)$ cycloalkylcarbonyl group;
(a22) a $(C_1-C_6)$ alkoxycarbonyl group;
(a23) a halo $(C_1-C_6)$ alkoxycarbonyl group;
(a24) a $(C_1-C_6)$ alkoxy $(C_1-C_6)$ alkoxycarbonyl group;

(a35) a N—($C_1$-$C_6$) alkylaminocarbonyl group;
(a41) a N—($C_3$-$C_6$) cycloalkylaminocarbonyl group;
(a52) a ($C_1$-$C_6$) alkylsulfonyl group;
(a69) a N—($C_1$-$C_6$) alkylaminothiocarbonyl group;
(a76) a N—($C_3$-$C_6$) cycloalkylaminothiocarbonyl group;
(a82) a phenyl ($C_1$-$C_6$) alkyl group;
(a84) a thiazolyl ($C_1$-$C_6$) alkyl group;
(a85) a substituted thiazolyl ($C_1$-$C_6$) alkyl group having, on a ring, one or two substituents each independently selected from the group consisting of a halogen atom, a ($C_1$-$C_6$) alkyl group, a halo ($C_1$-$C_6$) alkyl group and a ($C_1$-$C_6$) alkoxy group;
(a86) a phenylsulfonyl group; or
(a87) a substituted phenylsulfonyl group having, on a ring, one to five substituents each independently selected from the group consisting of a halogen atom, a ($C_1$-$C_6$) alkyl group, a halo ($C_1$-$C_6$) alkyl group and a ($C_1$-$C_6$) alkoxy group,
$R^2$ is
(b5) a phenyl group;
(b6) a substituted phenyl group having, on a ring, one to five substituents each independently selected from substituent group A;
(b7) a pyridyl group;
(b8) a substituted pyridyl group having, on a ring, one to four substituents each independently selected from substituent group A;
(b9) a pyridazinyl group;
(b10) a substituted pyridazinyl group having, on a ring, one to three substituents each independently selected from substituent group A;
(b11) a pyrimidinyl group;
(b12) a substituted pyrimidinyl group having, on a ring, one to three substituents each independently selected from substituent group A;
(b13) a pyrazinyl group;
(b14) a substituted pyrazinyl group having, on a ring, one to three substituents each independently selected from substituent group A;
(b21) an oxazolyl group;
(b22) a substituted oxazolyl group having, on a ring, one or two substituents each independently selected from substituent group A;
(b25) an oxadiazolyl group;
(b26) a substituted oxadiazolyl group having, on a ring, one substituent each independently selected from substituent group A;
(b27) a thienyl group;
(b28) a substituted thienyl group having, on a ring, one to three substituents each independently selected from substituent group A;
(b29) a thiazolyl group;
(b30) a substituted thiazolyl group having, on a ring, one or two substituents each independently selected from substituent group A;
(b31) an isothiazolyl group;
(b32) a substituted isothiazolyl group having, on a ring, one or two substituents each independently selected from substituent group A;
(b33) a thiadiazolyl group;
(b34) a substituted thiadiazolyl group having, on a ring, one substituent each independently selected from substituent group A;
(b97) a quinoxalinyl group;
(b98) a substituted quinoxalinyl group having, on a ring, one to five substituents each independently selected from substituent group A;
(b99) a quinolinyl group; or
(b100) a substituted quinolinyl group having, on a ring, one to six substituents each independently selected from substituent group A;
$R^3$ is
(c1) a hydrogen atom;
(c2) a ($C_1$-$C_6$) alkyl group;
(c3) a ($C_3$-$C_6$) cycloalkyl group;
(c5) a ($C_1$-$C_6$) alkylcarbonyl group; or
(c6) a ($C_1$-$C_6$) alkoxycarbonyl group,
$R^4$ is
(d1) a ($C_1$-$C_6$) alkyl group;
(d3) a ($C_2$-$C_6$) alkynyl group;
(d4) a ($C_3$-$C_6$) cycloalkyl group;
(d5) a halo ($C_1$-$C_6$) alkyl group;
(d9) a substituted ($C_1$-$C_6$) alkyl group having one to three substituents each independently selected from substituent group B;
(d10) a substituted ($C_3$-$C_6$) cycloalkyl group having, on a ring, one to three substituents each independently selected from substituent group C;
(d17) a phenyl group;
(d18) a substituted phenyl group having, on a ring, one to five substituents each independently selected from substituent group D;
(d19) a pyridyl group;
(d20) a substituted pyridyl group having, on a ring, one to four substituents each independently selected from substituent group D;
(d21) a pyridazinyl group;
(d22) a substituted pyridazinyl group having, on a ring, one to three substituents each independently selected from substituent group D;
(d23) a pyrimidinyl group;
(d24) a substituted pyrimidinyl group having, on a ring, one to three substituents each independently selected from substituent group D;
(d25) a pyrazinyl group;
(d26) a substituted pyrazinyl group having, on a ring, one to three substituents each independently selected from substituent group D;
(d43) a pyrazolyl group; or
(d44) a substituted pyrazolyl group having, on a ring, one to three substituents each independently selected from substituent group D,
$R^5$ is
(e1) a ($C_1$-$C_6$) alkyl group;
(e2) a ($C_2$-$C_6$) alkenyl group;
(e3) a ($C_2$-$C_6$) alkynyl group;
(e4) a ($C_3$-$C_6$) cycloalkyl group;
(e5) a halo ($C_1$-$C_6$) alkyl group;
(e6) a halo ($C_2$-$C_6$) alkenyl group;
(e9) a substituted ($C_1$-$C_6$) alkyl group having, on a chain, one to three substituents each independently selected from the group consisting of a cyano group, a ($C_1$-$C_6$) alkoxy group, a ($C_3$-$C_6$) cycloalkyl group, a ($C_1$-$C_6$) alkylcarbonyl group, a ($C_3$-$C_6$) cycloalkylcarbonyl group, a phenylcarbonyl group, a ($C_1$-$C_6$) alkoxycarbonyl group, an aminocarbonyl group, a halo ($C_1$-$C_6$) alkylcarbonyl group, a ($C_1$-$C_6$) alkylsulfanyl group, a tri-($C_1$-$C_6$) alkylsilyl ($C_1$-$C_6$) alkoxy group (wherein the ($C_1$-$C_6$) alkyl groups are the same as or different from each other), and a tri-($C_1$-$C_6$) alkylsilyl group (wherein the ($C_1$-$C_6$) alkyl groups are the same as or different from each other);
(e11) a phenyl ($C_1$-$C_6$) alkyl group;

(e12) a substituted phenyl ($C_1$-$C_6$) alkyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_3$-$C_6$) cycloalkyl group, a ($C_1$-$C_6$) alkoxycarbonyl group, a ($C_1$-$C_6$) alkylsulfanyl group, a ($C_1$-$C_6$) alkylsulfinyl group, a ($C_1$-$C_6$) alkylsulfonyl group, a halo ($C_1$-$C_6$) alkylsulfanyl group, a diphenylamino group, a phenoxy group, and a methylenedioxy group formed by two adjacent substituents together;

(e13) a pyridyl ($C_1$-$C_6$) alkyl group;

(e14) a substituted pyridyl ($C_1$-$C_6$) alkyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e15) a thiazolyl ($C_1$-$C_6$) alkyl group;

(e16) a substituted thiazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e17) an oxadiazolyl ($C_1$-$C_6$) alkyl group;

(e18) a substituted oxadiazolyl ($C_1$-$C_6$) alkyl group having a pyridyl group on a ring;

(e19) a naphthyl ($C_1$-$C_6$) alkyl group;

(e20) a substituted naphthyl ($C_1$-$C_6$) alkyl group having, on a ring, one to seven substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e21) a quinolinyl ($C_1$-$C_6$) alkyl group;

(e22) a substituted quinolinyl ($C_1$-$C_6$) alkyl group having, on a ring, one to six substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e23) a thienyl ($C_1$-$C_6$) alkyl group;

(e24) a substituted thienyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e25) a pyrazolyl ($C_1$-$C_6$) alkyl group;

(e26) a substituted pyrazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e27) an oxazolyl ($C_1$-$C_6$) alkyl group;

(e28) a substituted oxazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e29) an imidazolyl ($C_1$-$C_6$) alkyl group;

(e30) a substituted imidazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e31) a pyridyl group;

(e32) a substituted pyridyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e33) a phenyl group;

(e34) a substituted phenyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e35) a ($C_1$-$C_6$) alkylcarbonyl group; or (e36) a hydrogen atom, $R^3$ and $R^5$ are optionally bonded to each other to form a 5- or 6-membered ring, Y is an oxygen atom or $NR^6$ (wherein $R^6$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, a halo ($C_1$-$C_6$) alkylcarbonyl group, a ($C_1$-$C_6$) alkoxycarbonyl group, a phenylsulfonyl group, or a phenylsulfonyl group having, on a ring, one to five substituents each independently selected from the group consisting of a halogen atom, a cyano group, and a ($C_1$-$C_6$) alkyl group), m is 0 or 1, n is 0 or 1, substituent group A consists of (f1) a halogen atom;

(f2) a cyano group;

(f6) a ($C_1$-$C_6$) alkyl group;

(f9) a ($C_1$-$C_6$) alkoxy group;

(f10) a ($C_3$-$C_6$) cycloalkyl group;

(f11) a ($C_1$-$C_6$) alkylsulfanyl group;

(f14) a halo ($C_1$-$C_6$) alkyl group;

(f17) a halo ($C_1$-$C_6$) alkoxy group;

(f22) a N,N-di-($C_1$-$C_6$) alkylaminosulfonyl group (wherein the ($C_1$-$C_6$) alkyl moieties are the same as or different from each other);

(f59) a tetrazolyl group;

(f60) a substituted tetrazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group; and (f94) an aminocarbonyl group, substituent group B consists of (g1) a cyano group;

(g2) a ($C_3$-$C_6$) cycloalkyl group;

(g3) a ($C_1$-$C_6$) alkoxy group; and (g4) a ($C_1$-$C_6$) alkylsulfanyl group, substituent group C consists of (h1) a cyano group;

(h2) a ($C_1$-$C_6$) alkyl group; and (h10) a halo ($C_1$-$C_6$) alkyl group, and substituent group D consists of (i1) a halogen atom;

(i2) a cyano group;

(i7) a ($C_1$-$C_6$) alkyl group;

(i8) a ($C_1$-$C_6$) alkoxy group;

(i9) a ($C_3$-$C_6$) cycloalkyl group;

(i10) a ($C_1$-$C_6$) alkylsulfanyl group;

(i13) a halo ($C_1$-$C_6$) alkyl group;

(i14) a halo ($C_1$-$C_6$) alkoxy group;

(i15) a halo ($C_3$-$C_6$) cycloalkyl group;

(i19) a ($C_1$-$C_6$) alkoxycarbonyl group; and (i25) a methylenedioxy group formed by two adjacent substituents together and optionally substituted by one or two substituents each selected from the group consisting of a halogen atom, a phenyl group and a ($C_1$-$C_6$) alkyl group,

[4] The compound according to any one of [1] to [3] or a salt thereof, wherein $R^1$ is (a1) a hydrogen atom;

(a2) a ($C_1$-$C_6$) alkyl group;

(a6) a halo ($C_1$-$C_6$) alkyl group;

(a9) a substituted ($C_1$-$C_6$) alkyl group having, on a chain, one to three substituents each independently selected from the group consisting of a cyano group, a ($C_1$-$C_6$) alkoxy group and a ($C_3$-$C_6$) cycloalkyl group;

(a13) a ($C_3$-$C_6$) cycloalkylcarbonyl group;

(a22) a ($C_1$-$C_6$) alkoxycarbonyl group;

(a24) a ($C_1$-$C_6$) alkoxy ($C_1$-$C_6$) alkoxycarbonyl group;

(a35) a N—($C_1$-$C_6$) alkylaminocarbonyl group;

(a52) a ($C_1$-$C_6$) alkylsulfonyl group;

(a82) a phenyl ($C_1$-$C_6$) alkyl group; or (a85') a substituted thiazolyl ($C_1$-$C_6$) alkyl group having, on a ring, one or two substituents each independently selected from the group consisting of a halogen atom, $R^2$ is (b5) a phenyl group;

(b6) a substituted phenyl group having, on a ring, one to five substituents each independently selected from substituent group A;

(b7) a pyridyl group;

(b8) a substituted pyridyl group having, on a ring, one to four substituents each independently selected from substituent group A;

(b10) a substituted pyridazinyl group having, on a ring, one to three substituents each independently selected from substituent group A; or (b12) a substituted pyrimidinyl group having, on a ring, one to three substituents each independently selected from substituent group A, $R^3$ is (c1) a hydrogen atom;

(c2) a ($C_1$-$C_6$) alkyl group;

(c5) a ($C_1$-$C_6$) alkylcarbonyl group; or (c6) a ($C_1$-$C_6$) alkoxycarbonyl group, $R^4$ is (d4) a ($C_3$-$C_6$) cycloalkyl group;

(d17) a phenyl group;

(d18) a substituted phenyl group having, on a ring, one to five substituents each independently selected from substituent group D;

(d20) a substituted pyridyl group having, on a ring, one to four substituents each independently selected from substituent group D; or (d44) a substituted pyrazolyl group having, on a ring, one to three substituents each independently selected from substituent group D, $R^5$ is (e1) a ($C_1$-$C_6$) alkyl group;

(e2) a ($C_2$-$C_6$) alkenyl group;

(e5) a halo ($C_1$-$C_6$) alkyl group;

(e9') a substituted ($C_1$-$C_6$) alkyl group having, on a chain, one to three substituents each independently selected from the group consisting of a cyano group, a ($C_1$-$C_6$) alkoxy group, a ($C_3$-$C_6$) cycloalkyl group, an aminocarbonyl group, a ($C_1$-$C_6$) alkylsulfanyl group, and a tri-($C_1$-$C_6$) alkylsilyl ($C_1$-$C_6$) alkoxy group (wherein the ($C_1$-$C_6$) alkyl groups are the same as or different from each other);

(e11) a phenyl ($C_1$-$C_6$) alkyl group;

(e12') a substituted phenyl ($C_1$-$C_6$) alkyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_3$-$C_6$) cycloalkyl group, a ($C_1$-$C_6$) alkoxycarbonyl group, a ($C_1$-$C_6$) alkylsulfanyl group, a ($C_1$-$C_6$) alkylsulfonyl group, a halo ($C_1$-$C_6$) alkylsulfanyl group, and a diphenylamino group;

(e14') a substituted pyridyl ($C_1$-$C_6$) alkyl group having, on a ring, one to four substituents each independently selected from a halogen atom;

(e16') a substituted thiazolyl ($C_1$-$C_6$) alkyl group having, on a ring, one or two substituents each independently selected from a halogen atom;

(e18) a substituted oxadiazolyl ($C_1$-$C_6$) alkyl group having a pyridyl group on a ring;

(e19) a naphthyl ($C_1$-$C_6$) alkyl group;

(e21) a quinolinyl ($C_1$-$C_6$) alkyl group;

(e23) a thienyl ($C_1$-$C_6$) alkyl group;

(e27) an oxazolyl ($C_1$-$C_6$) alkyl group;

(e35) a ($C_1$-$C_6$) alkylcarbonyl group; or (e36) a hydrogen atom, $R^3$ and $R^5$ are optionally bonded to each other to form a 5- or 6-membered ring, each of n and m is 0, substituent group A consists of (f1) a halogen atom;

(f2) a cyano group;

(f6) a ($C_1$-$C_6$) alkyl group;

(f9) a ($C_1$-$C_6$) alkoxy group;

(f11) a ($C_1$-$C_6$) alkylsulfanyl group;

(f14) a halo ($C_1$-$C_6$) alkyl group; and (f94) an aminocarbonyl group, and substituent group D consists of (i1) a halogen atom;

(i2) a cyano group;

(i7) a ($C_1$-$C_6$) alkyl group;

(i8) a ($C_1$-$C_6$) alkoxy group;

(i10) a ($C_1$-$C_6$) alkylsulfanyl group;

(i14) a halo ($C_1$-$C_6$) alkoxy group; and (i19) a ($C_1$-$C_6$) alkoxycarbonyl group,

[5] An insecticidal agent comprising a compound according to any one of [1] to [4] or a salt thereof as an active ingredient,

[6] An agricultural and horticultural insecticidal agent comprising a compound according to any one of [1] to [4] or a salt thereof as an active ingredient,

[7] A method for using an insecticidal agent according to [5] or [6], comprising treating a plant or soil with an effective amount of the insecticidal agent, and

[8] Use of a compound according to any one of [1] to [4] or a salt thereof as an insecticidal agent.

Advantageous Effects of Invention

The compounds or salts thereof of the present invention have an excellent effect as an insecticidal agent. Also, compounds or salts thereof of the present invention exhibit an effect not only on pests in the agricultural and horticultural field but on pests parasitic on pet animals such as dogs or cats or livestock such as bovines or sheep.

DESCRIPTION OF EMBODIMENTS

In the definition of the general formula (1) for the compounds of the present invention, the term "halo" means "halogen atom" and refers to a chlorine atom, a bromine atom, an iodine atom or a fluorine atom.

The term "($C_1$-$C_6$) alkyl group" refers to a linear or branched alkyl group having 1 to 6 carbon atoms, for example, a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 2,3-dimethylpropyl group, a 1-ethylpropyl group, a 1-methylbutyl group, a 2-methylbutyl group, a normal hexyl group, an isohexyl group, a 2-hexyl group, a 3-hexyl group, a 2-methylpentyl group, a 3-methylpentyl group, a 1,1,2-trimethylpropyl group, and a 3,3-dimethylbutyl group.

The term "($C_2$-$C_6$) alkenyl group" refers to a linear or branched alkenyl group having 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, and a 3,3-dimethyl-1-butenyl group. The term "($C_2$-$C_6$) alkynyl group" refers to a linear or branched alkynyl group having 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexenyl group, a 3-methyl-1-butynyl group, and a 3,3-dimethyl-1-butynyl group.

The term "($C_3$-$C_6$) cycloalkyl group" refers to a cyclic alkyl group having 3 to 6 carbon atoms, for example, a cyclopropyl group, a cyclobutyl group, a cyclopentyl group, and a cyclohexyl group. The term "($C_1$-$C_6$) alkoxy group" refers to a linear or branched alkoxy group having 1 to 6 carbon atoms, for example, a methoxy group, an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group, an isohexyloxy group, and a 1,1,2-trimethylpropyloxy group.

The term "($C_1$-$C_6$) alkylsulfanyl group" refers to a linear or branched alkylsulfanyl group having 1 to 6 carbon atoms, for example, a methylsulfanyl group, an ethylsulfanyl group, a normal propylsulfanyl group, an isopropylsulfanyl group, a normal butylsulfanyl group, a secondary butylsulfanyl group, a tertiary butylsulfanyl group, a normal pentylsulfanyl group, an isopentylsulfanyl group, a tertiary pentylsulfanyl group, a neopentylsulfanyl group, a 2,3-dimethylpropylsulfanyl group, a 1-ethylpropylsulfanyl group, a 1-methylbutylsulfanyl group, a normal hexylsulfanyl group, an isohexylsulfanyl group, and a 1,1,2-trimethylpropylsulfanyl group.

The term "($C_1$-$C_6$) alkylsulfinyl group" refers to a linear or branched alkylsulfinyl group having 1 to 6 carbon atoms, for example, a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group, a tertiary pentylsulfinyl group, a neopentylsulfinyl group, a 2,3-dimethylpropylsulfinyl group, a 1-ethylpropylsulfinyl group, a 1-methylbutylsulfinyl group, a normal hexylsulfinyl group, an isohexylsulfinyl group, and a 1,1,2-trimethylpropylsulfinyl group.

The term "($C_1$-$C_6$) alkylsulfonyl group" refers to a linear or branched alkylsulfonyl group having 1 to 6 carbon atoms, for example, a methylsulfonyl group, an ethylsulfonyl group, a normal propylsulfonyl group, an isopropylsulfonyl group, a normal butylsulfonyl group, a secondary butylsulfonyl group, a tertiary butylsulfonyl group, a normal pentylsulfonyl group, an isopentylsulfonyl group, a tertiary pentylsulfonyl group, a neopentylsulfonyl group, a 2,3-dimethylpropylsulfonyl group, a 1-ethylpropylsulfonyl group, a 1-methylbutylsulfonyl group, a normal hexylsulfonyl group, an isohexylsulfonyl group, and a 1,1,2-trimethylpropylsulfonyl group.

The term "($C_1$-$C_6$) alkylcarbonyl group" refers to an alkylcarbonyl group having 2 to 7 carbon atoms, such as an alkylcarbonyl group having the above-described ($C_1$-$C_6$) alkyl group, for example, an acetyl group, a propanoyl group, a butanoyl group, a 2-methylpropanoyl group, a pentanoyl group, a 2-methylbutanoyl group, a 3-methylbutanoyl group, a pivaloyl group, and a hexanoyl group.

The term "($C_3$-$C_6$) cycloalkylcarbonyl group" refers to a cycloalkylcarbonyl group having 4 to 7 carbon atoms, such as a cycloalkylcarbonyl group having the above-described ($C_3$-$C_6$) cycloalkyl group, for example, a cyclopropylcarbonyl group, a cyclobutylcarbonyl group, a cyclopentylcarbonyl group, and a cyclohexylcarbonyl group.

The term "($C_1$-$C_6$) alkylcarbonylLamino group" refers to an alkylcarbonylamino group having 2 to 7 carbon atoms, such as an alkylcarbonylamino group having the above-described ($C_1$-$C_6$) alkyl group, for example, an acetylamino group, a propanoylamino group, a butanoylamino group, a 2-methylpropanoylamino group, a pentanoylamino group, a 2-methylbutanoylamino group, a 3-methylbutanoylamino group, a pivaloylamino group, and a hexanoylamino group.

The term "($C_1$-$C_6$) alkylsulfonylamino group" refers to a linear or branched alkylsulfonylamino group having 1 to 6 carbon atoms, for example, a methylsulfonylamino group, an ethylsulfonylamino group, a normal propylsulfonylamino group, an isopropylsulfonylamino group, a normal butylsulfonylamino group, a secondary butylsulfonylamino group, a tertiary butylsulfonylamino group, a normal pentylsulfonylamino group, an isopentylsulfonylamino group, a tertiary pentylsulfonylamino group, a neopentylsulfonylamino group, a 2,3-dimethylpropylsulfonylamino group, a 1-ethylpropylsulfonylamino group, a 1-methylbutylsulfonylamino group, a normal hexylsulfonylamino group, an isohexylsulfonylamino group, and a 1,1,2-trimethylpropylsulfonylamino group.

The term "N—($C_1$-$C_6$) alkylaminocarbonyl group" refers to an alkylaminocarbonyl group having 2 to 7 carbon atoms which has a linear or branched alkyl group having 1 to 6 carbon atoms, for example, a N-methylaminocarbonyl group, a N-ethylaminocarbonyl group, a N-normal propylaminocarbonyl group, a N-isopropylaminocarbonyl group, a N-normal butylaminocarbonyl group, a N-isobutylaminocarbonyl group, a N-secondary butylaminocarbonyl group, a N-tertiary butylaminocarbonyl group, a N-normal pentylaminocarbonyl group, a N-isopentylaminocarbonyl group, a N-tertiary pentylaminocarbonyl group, a N-neopentyaminocarbonyl group, a N-normal hexylaminocarbonyl group, and a N-isohexylaminocarbonyl group.

The term "N,N-di-($C_1$-$C_6$) alkylaminocarbonyl group" refers to a dialkylaminocarbonyl group having 3 to 13 carbon atoms which has a linear or branched alkyl group having 1 to 6 carbon atoms, for example, a N,N-dimethylaminocarbonyl group, a N,N-diethylaminocarbonyl group, a N,N-di-normal propylaminocarbonyl group, a N,N-diisopropylaminocarbonyl group, a N,N-di-normal butylaminocarbonyl group, a N,N-di-secondary butylaminocarbonyl group, a N,N-di-tertiary butylaminocarbonyl group, a N-methyl-N-ethylaminocarbonyl group, a N-methyl-N-normal propylaminocarbonyl group, a N-methyl-N-isopropylaminocarbonyl group, a N-methyl-N-normal butylaminocarbonyl group, a N-methyl-N-secondary butylaminocarbonyl group, a N-methyl-N-tertiary butylaminocarbonyl group, a N-methyl-N-normal pentylaminocarbonyl group, a N-methyl-N-isopentylaminocarbonyl group, a N-methyl-N-tertiary pentylaminocarbonyl group, a N-methyl-N-neopentylaminocarbonyl group, a N-methyl-N-(2,3-dimethylpropyl)aminocarbonyl group, a N-methyl-N-(1-ethylpropyl)aminocarbonyl group, a N-methyl-N-(1-methylbutyl)aminocarbonyl group, a N-methyl-N-normal hexylaminocarbonyl group, a N-methyl-N-isohexylaminocarbonyl group, and a N-methyl-N-(1,1,2-trimethylpropyl)aminocarbonyl group.

The term "($C_1$-$C_6$) alkoxycarbonyl group" refers to an alkoxycarbonyl group having 2 to 7 carbon atoms, such as an alkoxycarbonyl group having the above-described ($C_1$-$C_6$) alkoxy group, for example, a methoxycarbonyl group, an ethoxycarbonyl group, a normal propoxycarbonyl group, an isopropoxycarbonyl group, a normal butoxycarbonyl group, an isobutoxycarbonyl group, a secondary butoxycarbonyl group, a tertiary butoxycarbonyl group, and a pentyloxycarbonyl group.

The term "N—($C_1$-$C_6$) alkylaminosulfonyl group" refers to a linear or branched alkylaminosulfonyl group having 1 to 6 carbon atoms, for example, a N-methylaminosulfonyl group, a N-ethylaminosulfonyl group, a N-normal propylaminosulfonyl group, a N-isopropylaminosulfonyl group, a N-normal butylaminosulfonyl group, a N-secondary butylaminosulfonyl group, a N-tertiary butylaminosulfonyl group, a N-normal pentylaminosulfonyl group, a N-isopentylaminosulfonyl group, a N-tertiary pentylaminosulfonyl group, a N-neopentylaminosulfonyl group, a N-(2,3-dimethylpropyl)aminosulfonyl group, a N-(1-ethylpropyl)aminosulfonyl group, a N-(1-methylbutyl)aminosulfonyl group, a N-normal hexylaminosulfonyl group, a N-isohexylaminosulfonyl group, and a N-(1,1,2-trimethylpropyl)aminosulfonyl group.

The term "N,N-di-($C_1$-$C_6$) alkylaminosulfonyl group" refers to a dialkylaminosulfonyl group having 2 to 12 carbon atoms which has a linear or branched alkyl group having 1 to 6 carbon atoms, for example, a N,N-dimethylaminosulfonyl group, a N,N-diethylaminosulfonyl group, a N,N-di-normal propylaminosulfonyl group, a N,N-diisopropylaminosulfonyl group, a N,N-di-normal butylaminosulfonyl group, a N,N-di-secondary butylaminosulfonyl group, a N,N-di-tertiary butylaminosulfonyl group, a N-methyl-N-ethylaminosulfonyl group, a N-methyl-N-normal propylaminosulfonyl group, a N-methyl-N-isopropylaminosulfonyl group, a N-methyl-N-normal butylaminosulfonyl group, a N-methyl-N-secondary butylaminosulfonyl group, a N-methyl-N-tertiary butylaminosulfonyl group, a N-methyl-N-normal pentylaminosulfonyl group, a N-methyl-N-isopentylaminosulfonyl group, a N-methyl-N-tertiary pentylaminosulfonyl group, a N-methyl-N-neopentylaminosulfonyl group, a N-methyl-N-(2,3-dimethylpropyl)aminosulfonyl group, a N-methyl-N-(1-ethylpropyl)aminosulfonyl group, a N-methyl-N-(1-methylbutyl)aminosulfonyl group, a N-methyl-N-normal hexylaminosulfonyl group, a N-methyl-N-isohexylaminosulfonyl group, and a N-methyl-N-(1,1,2-trimethylpropyl)aminosulfonyl group.

The above-described "($C_1$-$C_6$) alkyl group", "($C_2$-$C_6$) alkenyl group", "($C_2$-$C_6$) alkynyl group", "($C_1$-$C_6$) alkoxy group", "($C_1$-$C_6$) alkylsulfanyl group", "($C_1$-$C_6$) alkylsulfinyl group", "($C_1$-$C_6$) alkylsulfonyl group", "($C_3$-$C_6$) cycloalkyl group", "($C_1$-$C_6$) alkylcarbonylamino group", "($C_1$-$C_6$) alkylsulfonylamino group", "N—($C_1$-$C_6$) alkylaminocarbonyl group", or the like may be substituted at a substitutable position by one or two or more halogen atoms. Two or more halogen atoms as such substituents may be the same as or different from each other.

The substituted groups are referred to as "halo ($C_1$-$C_6$) alkyl group", "halo ($C_2$-$C_6$) alkenyl group", "halo ($C_2$-$C_6$) alkynyl group", "halo ($C_1$-$C_6$) alkoxy group", "halo ($C_1$-$C_6$) alkylsulfanyl group", "halo ($C_1$-$C_6$) alkylsulfinyl group", "halo ($C_1$-$C_6$) alkylsulfonyl group", "halo ($C_3$-$C_6$) cycloalkyl group", "halo ($C_1$-$C_6$) alkylcarbonylamino group", "halo ($C_1$-$C_6$) alkylsulfonylamino group", "N-halo ($C_1$-$C_6$) alkylaminocarbonyl group", and the like, respectively.

An expression such as "($C_1$-$C_6$)", "($C_2$-$C_6$)", or "($C_3$-$C_6$)" refers to the range of the number of carbon atoms in each substituent. Further, groups linked to the above-described substituents can also be defined as above. For example, the term "($C_1$-$C_6$) alkoxy ($C_1$-$C_6$) alkyl group" represents that a linear or branched alkoxy group having 1 to 6 carbon atoms is bonded to a linear or branched alkyl group having 1 to 6 carbon atoms.

The term "aryl group" refers to an aromatic hydrocarbon group having 6 to 10 carbon atoms, for example, a phenyl group, a 1-naphthyl group, and a 2-naphthyl group.

Examples of the term "5- to 10-membered ring heterocyclic group" include a 5- or 6-membered monocyclic aromatic heterocyclic group containing one to four heteroatoms selected from an oxygen atom, a sulfur atom and a nitrogen atom in addition to a carbon atom as ring-constituting atoms, an aromatic condensed heterocyclic group in which the monocyclic aromatic heterocyclic ring is condensed with a benzene ring or a monocyclic aromatic ring, a 4- to 6-membered monocyclic non-aromatic heterocyclic group, and a non-aromatic condensed heterocyclic group in which the monocyclic non-aromatic heterocyclic ring is condensed with a benzene ring or a monocyclic aromatic ring. A ring-constituting atom of the 5- to 10-membered ring heterocyclic group may be oxidized with an oxo group.

Examples of the "monocyclic aromatic heterocyclic group" include a furyl group, a thienyl group, a pyridyl group, a 2-oxopyridyl group, a pyrimidinyl group, a pyridazinyl group, a pyrazinyl group, a pyrrolyl group, an imidazolyl group, a pyrazolyl group, a thiazolyl group, an isothiazolyl group, an oxazolyl group, an isoxazolyl group, an oxadiazolyl group (e.g., a 1,3,4-oxadiazolyl group and a 1,2,4-oxadiazolyl group), a thiadiazolyl group (e.g., a 1,3,4-thiadiazolyl group and a 1,2,4-thiadiazolyl group), a triazolyl group (e.g., a 1,2,4-triazolyl group), a tetrazolyl group, and a triazinyl group (e.g., a 1,3,5-triazinyl group and a 1,2,4-triazinyl group). Examples of the "aromatic condensed heterocyclic group" include a quinolinyl group, an isoquinolinyl group, a quinazolinyl group, a quinoxalinyl group, a cinnolinyl group, a phthalazinyl group, a naphthyridinyl group, a benzofuranyl group, a benzothienyl group, a benzoxazolyl group, a benzisoxazolyl group, a benzothiazolyl group, a benzisothiazolyl group, a benzimidazolyl group, a benzotriazolyl group, an indolyl group, an isoindolyl group, an indazolyl group, a furopyridyl group, a thienopyridyl group, a pyrrolopyridyl group (e.g., a pyrrolo[1,2-a]pyridyl group and a pyrrolo[2,3-b]pyridyl group), an oxazolopyridyl group (e.g., an oxazolo[3,2-a]pyridyl group, an oxazolo[5,4-b]pyridyl group, and an oxazolo[4,5-b]pyridyl group), an isoxazolopyridyl group (e.g., an isoxazolo[2,3-a]pyridyl group, an isoxazolo[4,5-b]pyridyl group, and an isoxazolo[5,4-b]pyridyl group), a thiazolopyridyl group (e.g., a thiazolo[3,2-a]pyridyl group, a thiazolo[5,4-b]pyridyl group, and a thiazolo[4,5-b]pyridyl group), an isothiazolopyridyl group (e.g., an isothiazolo[2,3-a]pyridyl group, an isothiazolo[4,5-b]pyridyl group, and an isothiazolo[5,4-b]pyridyl group), an imidazopyridyl group (e.g., an imidazo[1,2-a]pyridyl group and an imidazo[4,5-b]pyridyl group), a pyrazolopyridyl group (e.g., a pyrazolo[1,5-a]pyridyl group, a pyrazolo[3,4-a]pyridyl group, and a pyrazolo[4,3-a]pyridyl group), an indolizinyl group, a triazolopyridyl group (e.g., a [1,2,4]triazolo[1,5-a]pyridyl group), a triazolopyrimidinyl group, a pyrrolopyrimidinyl group, a pyrrolopyrazinyl group, an imidazopyrimidinyl group, an imidazopyrazinyl group, a pyrazolopyrimidinyl group, a pyrazolothienyl group, and a pyrazolotriazinyl group.

Examples of the "monocyclic non-aromatic heterocyclic group" include an oxetanyl group, a thietanyl group, an azetidinyl group, a pyrrolidinyl group, a pyrrolidinyl-2-one group, a piperidinyl group, a morpholinyl group, a thiomorpholinyl group, a piperazinyl group, a hexamethyleneiminyl group, an oxazolidinyl group, a thiazolidinyl group, an imidazolidinyl group, an oxazolinyl group, a thiazolinyl group, an isoxazolinyl group, an imidazolinyl group, a dioxolyl group, a dioxolanyl group, a dihydrooxadiazolyl group, a 2-oxo-pyrrolidin-1-yl group, a 2-oxopyridin-4-yl group, a 2,4-dioxopyrimidin-5-yl group, a 2-oxo-1,3-oxazolidin-5-yl group, a 5-oxo-1,2,4-oxadiazolin-3-yl group, a 1,3-dioxolan-2-yl group, a 1,3-dioxan-2-yl group, a 1,3-dioxepan-2-yl group, a pyranyl group, a tetrahydropyranyl group, a thiopyranyl group, a tetrahydrothiopyranyl group, a 1-oxidotetrahydrothiopyranyl group, a 1,1-dioxidotetrahydrothiopyranyl group, a tetrahydrofuranyl group, a dioxanyl group, a pyrazolidinyl group, a pyrazolinyl group, a tetrahydropyrimidinyl group, a dihydrotriazolyl group, and a tetrahydrotriazolyl group. Examples of the "non-aromatic condensed heterocyclic group" include a dihydroindolyl group, a dihydroisoindolyl group, a dihydrobenzofuranyl group, a dihydrobenzodioxinyl group, a dihydrobenzodioxepinyl group, a tetrahydrobenzofuranyl group, a chromenyl group, a dihydroquinolinyl group, a tetrahydroquinolinyl group, a dihydroisoquinolinyl group, a tetrahydroisoquinolinyl group, and a dihydrophthalazinyl group.

$R^3$ and $R^4$ are optionally bonded to each other to form a ring. The "ring" is a ring formed through the binding between a group derived from $R^3$ by the removal of an arbitrary hydrogen atom and a group derived from $R^4$ by the removal of an arbitrary hydrogen atom. For example, when $R^3$ is an ethyl group and $R^4$ is a normal propyl group, piperidine is formed through the binding between a group derived from $R^3$ by the removal of a hydrogen atom at the distal end from the ethyl group and a group derived from $R^4$ by the removal of a hydrogen atom at the distal end from the normal propyl group. Examples of the "ring" include 3- to 7-membered nitrogen-containing heterocyclic rings such as aziridine, azetidine, pyrrolidine, piperidine, homopiperidine, piperazine, homopiperazine, morpholine, and homomorpholine. The nitrogen-containing heterocyclic ring may be condensed with a benzene ring. The nitrogen-containing heterocyclic ring and the benzene ring may each be substituted by one to six substituents selected from the group consisting of a halogen atom, a $(C_1-C_6)$ alkyl group, a halo $(C_1-C_6)$ alkyl group, and the like.

$R^3$ and $R^5$ are optionally bonded to each other to form a 5- or 6-membered ring. The "5- or 6-membered ring" is a ring formed through the binding between a group derived from $R^3$ by the removal of an arbitrary hydrogen atom and a group derived from $R^5$ by the removal of an arbitrary hydrogen atom. For example, when $R^3$ is an acetyl group and $R^5$ is a methyl group, 1,3-thiazolidin-4-one is formed through the binding between a group derived from $R^3$ by the removal of a hydrogen atom from the acetyl group and a group derived from $R^5$ by the removal of a hydrogen atom from the methyl group. When one of $R^3$ and $R^5$ is a hydrogen atom, the other group may be directly bonded to the nitrogen atom bonded to $R^3$ or the sulfur atom bonded to $R^5$ to form a 5- or 6-membered ring. Examples of the "5- or 6-membered ring" include 1,3-thiazolidine, hexahydro-1,3-thiazine, 1,3-thiazolidin-4-one, 1,3-thiazolidin-5-one, hexahydro-1,3-thiazin-4-one, and hexahydro-1,3-thiazin-6-one.

Examples of the salts of the compounds represented by the general formula (1) of the present invention can include inorganic acid salts such as hydrochloride, sulfate, nitrate, and phosphate, organic acid salts such as acetate, fumarate, maleate, oxalate, methanesulfonate, benzenesulfonate, and p-toluenesulfonate, and salts with inorganic or organic bases such as sodium ions, potassium ions, calcium ions, cesium ions, magnesium ions, ammonium ions, and trimethylammonium.

The compounds represented by the general formula (1) of the present invention and salts thereof may have one or more asymmetric centers in their structural formulas and may also have two or more optical isomers and diastereomers. The present invention also encompasses all of the respective optical isomers and mixtures containing these isomers at arbitrary ratios. Also, the compound represented by the general formula (1) of the present invention and a salt thereof may have two or more geometric isomers derived from carbon-carbon double bonds or carbon-nitrogen double bonds in its structural formula. The present invention also encompasses all of the respective geometric isomers and mixtures containing these isomers at arbitrary ratios. Furthermore, the compounds represented by the general formula (1) of the present invention and salts thereof may have a plurality of tautomers. The present invention also encompasses all of the respective tautomers and mixtures containing these tautomers at arbitrary ratios.

Preferred forms of the compounds represented by the general formula (1) of the present invention will be given below.

In the general formula (1), $R^1$ is preferably the above-described group (a1), (a2), (a6), (a9), (a11), (a12), (a13), (a22), (a23), (a24), (a35), (a41), (a52), (a69), (a76), (a82), (a84), (a85), (a86), or (a87), more preferably the above-described group (a1), (a2), (a6), (a9), (a13), (a22), (a24), (a35), (a52), (a82), or (a85').

In the general formula (1), $R^2$ is preferably the above-described group (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), (b48), (b49), (b50), (b51), (b52), (b53), (b54), (b55), (b56), (b57), (b58), (b59), (b60), (b61), (b62), (b63), (b64), (b65), (b66), (b67), (b68), (b69), (b70), (b71), (b72), (b73), (b74), (b75), (b76), (b77), (b78), (b79), (b80), (b81), (b82), (b83), (b84), (b85), (b86), (b87), (b88), (b89), (b90), (b91), (b92), (b93), (b94), (b95), (b96), (b97), (b98), (b99), (b100), (b101), (b102), (b103), (b104), (b105), (b106), (b107), (b108), (b109), (b110), (b111), or (b112), more preferably the above-described group (b5), (b6), (b7), (b8), (b9), (b10), (b11), (b12), (b13), (b14), (b21), (b22), (b25), (b26), (b27), (b28), (b29), (b30), (b31), (b32), (b33), (b34), (b97), (b98), (b99), or (b100), further preferably the above-described group (b5), (b6), (b7), (b8), (b10), or (b12).

In the general formula (1), $R^3$ is preferably the above-described group (c1), (c2), (c3), (c5), or (c6), more preferably the above-described group (c1), (c2), (c5), or (c6).

In the general formula (1), $R^4$ is preferably the above-described group (d1), (d3), (d4), (d5), (d9), (d10), (d17), (d18), (d19), (d20), (d21), (d22), (d23), (d24), (d25), (d26), (d43), or (d44), more preferably the above-described group (d4), (d17), (d18), (d20), or (d44).

In the general formula (1), $R^5$ is preferably the above-described group (e1), (e2), (e3), (e4), (e5), (e6), (e9), (e11), (e12), (e13), (e14), (e15), (e16), (e17), (e18), (e19), (e20), (e21), (e22), (e23), (e24), (e25), (e26), (e27), (e28), (e29), (e30), (e31), (e32), (e33), (e34), (e35), or (e36), more preferably the above-described group (e1), (e2), (e5), (e9'), (e11), (e12'), (e14'), (e16'), (e18), (e19), (e21), (e23), (e27), (e35), or (e36).

In the general formula (1), substituent group A preferably consists of the above-described groups (f1), (f2), (f6), (f9), (f10), (f11), (f14), (f17), (f22), (f59), (f60), and (f94), more preferably the above-described groups (f1), (f2), (f6), (f9), (f11), (f14), and (f94).

In the general formula (1), substituent group B preferably consists of the above-described groups (g1), (g2), (g3), and (g4).

In the general formula (1), substituent group C preferably consists of the above-described groups (h1), (h2), and (h10).

In the general formula (1), substituent group D preferably consists of the above-described groups (i1), (i2), (a7), (i8), (i9), (i10), (i13), (i14), (i15), (119), and (i25), more preferably the above-described groups (i1), (i2), (i7), (i8), (i10), (i14), and (i19).

Various compounds of the present invention can be produced by, for example, production methods given below, though the present invention is not limited by these methods.

Production Method 1

The compounds represented by the general formulas (1-1) and (1-2) of the present invention can be produced by the following steps [a] and [b] from a compound represented by the general formula (2).

[Formula 2]

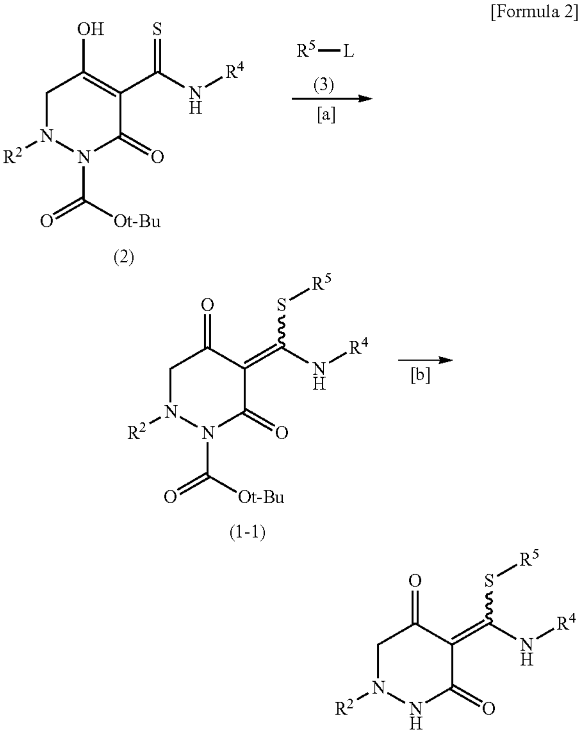

(2)

(1-1)

(1-2)

wherein $R^2$, $R^4$ and $R^5$ are the same as above; and L represents a leaving group, for example, chlorine, bromine, iodine, a ($C_1$-$C_6$) alkylcarbonyloxy group, or a ($C_1$-$C_6$) alkoxycarbonyloxy group.

Production Method of Step [a]

The compound represented by the general formula (1-1) of the present invention can be produced by reacting the compound represented by the general formula (2) with a compound represented by the general formula (3) in the presence of a base and an inert solvent.

Examples of the base that can be used in this reaction can include inorganic bases including hydroxides of alkali metal atoms such as sodium hydroxide and potassium hydroxide, hydrides of alkali metals such as sodium hydride and potassium hydride, alkali metal salts of alcohols such as sodium ethoxide and potassium t-butoxide, and carbonates such as sodium carbonate, potassium carbonate, and sodium bicarbonate, and organic bases including triethylamine, pyridine, N,N-dimethyl-4-aminopyridine, and DBU. The amount of the base used is in the range of usually 1 to 10 times the mol of the compound represented by the general formula (2).

The inert solvent that can be used in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, esters such as methyl acetate, ketones such as acetone and methyl ethyl ketone, aprotic polar solvents such as N,N-dimethylformamide, N,N-dimethylacetamide, dimethyl sulfoxide, and 1,3-dimethyl-2-imidazolidinone, and alcohols such as methanol, ethanol, propanol, butanol, and 2-propanol. These inert solvents can each be used singly or can be used as a mixture of two or more thereof. The amount of the solvent used can be appropriately selected from the range of usually 0.1 to 100 L per mol of the compound represented by the general formula (2).

Since this reaction is equimolar reaction, each compound can be used in an equimolar amount, or an excess of any compound may be used. The reaction temperature in the reaction can be in the range of usually 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method of Step [b]

The compound represented by the general formula (1-2) can be produced by hydrolyzing the compound represented by the general formula (1-1) in the presence or absence of an acid and an inert solvent.

Examples of the acid that can be used in this reaction can include inorganic acids such as hydrochloric acid, sulfuric acid, and nitric acid, organic acids such as formic acid, acetic acid, propionic acid, trifluoroacetic acid, and benzoic acid, sulfonic acids such as methanesulfonic acid, a trifluoromethanesulfonic acid, and p-toluenesulfonic acid, and phosphoric acid. The amount of the acid used can be appropriately selected in the range of 0.01 to 10 times the mol of the compound represented by the general formula (1-1). The acid may be used as a solvent.

The inert solvent for use in this reaction can be a solvent that does not markedly inhibit the progression of the reaction. Examples of the inert solvent can include aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, chain or cyclic ethers such as diethyl ether, methyl tertiary butyl ether, dioxane, and tetrahydrofuran, esters such as ethyl acetate, amides such as N,N-dimethylformamide and N,N-dimethylacetamide, ketones such as acetone and methyl ethyl ketone, and aprotic polar solvents such as dimethyl sulfoxide and 1,3-dimethyl-2-imidazolidinone. These inert solvents can each be used singly or can be used as a mixture of two or more thereof. The amount of the inert solvent used is not particularly limited as long as the amount allows a reaction reagent to be dissolved. The amount can be appropriately selected from the range of 0.5 L to 100 L per mol of the compound represented by the general formula (1-1). No solvent may be used when the acid is used as a solvent.

The reaction temperature can be in the range of room temperature to the boiling point of the acid or the inert solvent used, and the reaction time varies depending on a reaction scale or the reaction temperature and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method 2

The compounds represented by the general formulas (1-3) and (1-4) of the present invention can be produced by the following steps [a] and [c] from a compound represented by the general formula (4). The reaction conditions of the step [a] are the same as above.

[Formula 3]

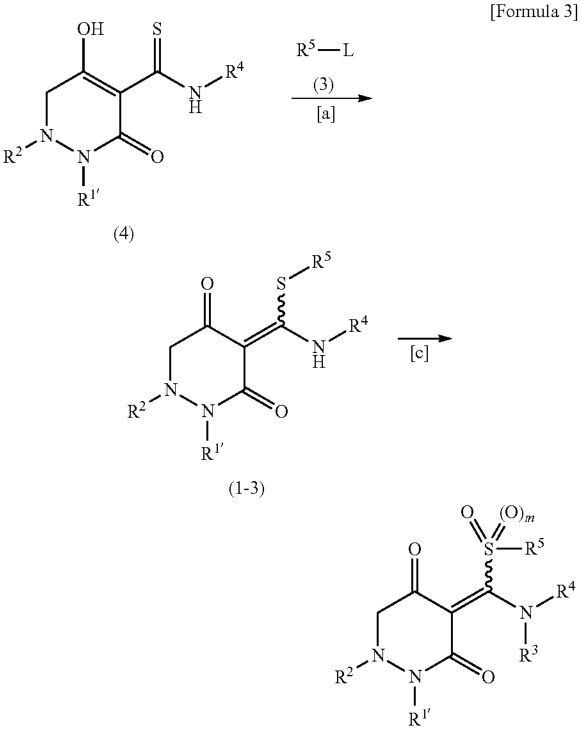

(4)

(1-3)

(1-4)

wherein $R^2$, $R^4$, $R^5$ and m are the same as above; $R^{1'}$ represents a $(C_1\text{-}C_6)$ alkyl group, a $(C_2\text{-}C_6)$ alkenyl group, a $(C_2\text{-}C_6)$ alkynyl group, a $(C_3\text{-}C_6)$ cycloalkyl group, a halo $(C_1\text{-}C_6)$ alkyl group, a halo $(C_3\text{-}C_6)$ cycloalkyl group, a $(C_1\text{-}C_6)$ alkoxy group, a substituted $(C_1\text{-}C_6)$ alkyl group having, on a chain, one to three substituents each independently selected from the group consisting of a cyano group, a $(C_1\text{-}C_6)$ alkoxy group and a $(C_3\text{-}C_6)$ cycloalkyl group, a substituted $(C_3\text{-}C_6)$ cycloalkyl group having one to three substituents each independently selected from the group consisting of a cyano group, a $(C_1\text{-}C_6)$ alkyl group and a $(C_1\text{-}C_6)$ alkoxy group, a $(C_1\text{-}C_6)$ alkylcarbonyl group, a halo $(C_1\text{-}C_6)$ alkylcarbonyl group, a $(C_3\text{-}C_6)$ cycloalkylcarbonyl group, a $(C_1\text{-}C_6)$ alkoxy $(C_1\text{-}C_6)$ alkylcarbonyl group, a $(C_1\text{-}C_6)$ alkylsulfanyl $(C_1\text{-}C_6)$ alkylcarbonyl group, a phenylcarbonyl group, a substituted phenylcarbonyl group having one to three substituents each independently selected from the group consisting of a halogen atom, a cyano group, a $(C_1\text{-}C_6)$ alkyl group and a $(C_1\text{-}C_6)$ alkoxy group, a thienylcarbonyl group, a substituted thienylcarbonyl group having one to three substituents each independently selected from the group consisting of a halogen atom, a cyano group, a $(C_1\text{-}C_6)$ alkyl group and a $(C_1\text{-}C_6)$ alkoxy group, a thiazolylcarbonyl group, a substituted thiazolylcarbonyl group having one to three substituents each independently selected from the group consisting of a halogen atom, a cyano group, a ($C_1$-$C_6$) alkyl group and a ($C_1$-$C_6$) alkoxy group, a ($C_1$-$C_6$) alkoxycarbonyl group, a halo ($C_1$-$C_6$) alkoxycarbonyl group, a ($C_1$-$C_6$) alkoxy ($C_1$-$C_6$) alkoxycarbonyl group, a ($C_1$-$C_6$) alkylsulfanyl ($C_1$-$C_6$) alkoxycarbonyl group, a ($C_1$-$C_6$) alkoxy ($C_1$-$C_6$) alkoxy ($C_1$-$C_6$) alkoxycarbonyl group, a ($C_2$-$C_6$) alkenyloxycarbonyl group, a ($C_2$-$C_6$) alkynyloxycarbonyl group, a ($C_3$-$C_6$) cycloalkoxycarbonyl group, a phenyloxycarbonyl group, a substituted phenyloxycarbonyl group having one to three substituents each independently selected from the group consisting of a halogen atom, a cyano group, a nitro group and a ($C_1$-$C_6$) alkyl group, a phenyl ($C_1$-$C_6$) alkoxycarbonyl group, a substituted phenyl ($C_1$-$C_6$) alkoxycarbonyl group having one to three substituents each independently selected from the group consisting of a halogen atom, a cyano group, a nitro group and a ($C_1$-$C_6$) alkyl group, an aminocarbonyl group, a N—($C_1$-$C_6$) alkylaminocarbonyl group, a N,N-di-($C_1$-$C_6$) alkylaminocarbonyl group (wherein the ($C_1$-$C_6$) alkyl moieties are the same as or different from each other), a N-halo ($C_1$-$C_6$) alkylaminocarbonyl group, a N—($C_2$-$C_6$) alkenylaminocarbonyl group, a N—($C_2$-$C_6$) alkynylaminocarbonyl group, a N—($C_1$-$C_6$) alkyl-N—($C_2$-$C_6$) alkynylaminocarbonyl group, a N—($C_3$-$C_6$) cycloalkylaminocarbonyl group, a N—($C_1$-$C_6$) alkoxyaminocarbonyl group, a N—($C_1$-$C_6$) alkoxy ($C_1$-$C_6$) alkylaminocarbonyl group, a N—($C_1$-$C_6$) alkylsulfanyl ($C_1$-$C_6$) alkylaminocarbonyl group, a N-phenyl ($C_1$-$C_6$) alkylaminocarbonyl group, a N-substituted phenyl ($C_1$-$C_6$) alkylaminocarbonyl group having one to three substituents each independently selected from the group consisting of a halogen atom, a cyano group, a nitro group and a ($C_1$-$C_6$) alkyl group, a pyrrolidinylcarbonyl group, a N—($C_1$-$C_6$) alkylhydrazinocarbonyl group, a N,N-di-($C_1$-$C_6$) alkylhydrazinocarbonyl group (wherein the ($C_1$-$C_6$) alkyl moieties are the same as or different from each other), a N-phenylaminocarbonyl group, a N-substituted phenylaminocarbonyl group having one to three substituents each independently selected from the group consisting of a halogen atom, a cyano group and a ($C_1$-$C_6$) alkyl group, a ($C_1$-$C_6$) alkylsulfonyl group, a halo ($C_1$-$C_6$) alkylsulfonyl group, a N—($C_1$-$C_6$) alkylaminosulfonyl group, a N-halo ($C_1$-$C_6$) alkylaminosulfonyl group, a ($C_1$-$C_6$) alkylthiocarbonyl group, a halo ($C_1$-$C_6$) alkylthiocarbonyl group, a ($C_3$-$C_6$) cycloalkylthiocarbonyl group, a ($C_1$-$C_6$) alkoxy ($C_1$-$C_6$) alkylthiocarbonyl group, a ($C_1$-$C_6$) alkylthio ($C_1$-$C_6$) alkylthiocarbonyl group, a ($C_1$-$C_6$) alkoxythiocarbonyl group, a halo ($C_1$-$C_6$) alkoxythiocarbonyl group, a pyrrolidinylthiocarbonyl group, a phenylthiocarbonyl group, a substituted phenylthiocarbonyl group having one to three substituents each independently selected from the group consisting of a halogen atom, a cyano group and a ($C_1$-$C_6$) alkyl group, a phenyloxythiocarbonyl group, a phenyl ($C_1$-$C_6$) alkylthiocarbonyl group, a substituted phenyl ($C_1$-$C_6$) alkylthiocarbonyl group having one to three substituents each independently selected from the group consisting of a halogen atom, a cyano group and a ($C_1$-$C_6$) alkyl group, a N—($C_1$-$C_6$) alkylaminothiocarbonyl group, a N-halo ($C_1$-$C_6$) alkylaminothiocarbonyl group, a N,N-di-($C_1$-$C_6$) alkylaminothiocarbonyl group (wherein the ($C_1$-$C_6$) alkyl moieties are the same as or different from each other), a N—($C_2$-$C_6$) alkenylaminothiocarbonyl group, a N—($C_2$-$C_6$) alkynylaminothiocarbonyl group, a N—($C_1$-$C_6$) alkyl-N—($C_2$-$C_6$) alkynylaminothiocarbonyl group, a N—($C_1$-$C_6$) alkylsulfanyl ($C_1$-$C_6$) alkylaminothiocarbonyl group, a N—($C_3$-$C_6$) cycloalkylaminothiocarbonyl group, a N—($C_1$-$C_6$) alkoxy ($C_1$-$C_6$) alkylaminothiocarbonyl group, a N-phenylaminothiocarbonyl group, a substituted N-phenylaminothiocarbonyl group having one to three substituents each independently selected from the group consisting of a halogen atom, a cyano group and a ($C_1$-$C_6$) alkyl group, a N-phenyl ($C_1$-$C_6$) alkylaminothiocarbonyl group, a substituted N-phenyl ($C_1$-$C_6$) alkylaminothiocarbonyl group having one to three substituents each independently selected from the group consisting of a halogen atom, a cyano group and a ($C_1$-$C_6$) alkyl group, a phenyl ($C_1$-$C_6$) alkyl group, or a substituted phenyl ($C_1$-$C_6$) alkyl group having, on a ring, one to three substituents each independently selected from the group consisting of a halogen atom, a ($C_1$-$C_6$) alkyl group, a halo ($C_1$-$C_6$) alkyl group and a ($C_1$-$C_6$) alkoxy group; and L represents a leaving group, for example, chlorine, bromine, iodine, a ($C_1$-$C_6$) alkylcarbonyloxy group, or a ($C_1$-$C_6$) alkoxycarbonyloxy group.

Production Method of Step [c]

The compound represented by the general formula (1-4) of the present invention can be produced by reacting the compound represented by the general formula (1-3) with an oxidizing agent in an inert solvent.

Examples of the oxidizing agent for use in this reaction can include peroxides such as hydrogen peroxide water, perbenzoic acid, and m-chloroperbenzoic acid. The amount of the oxidizing agent used can be appropriately selected from the range of 1 to 5 times the mol of the compound represented by the general formula (1-3).

The inert solvent that can be used in this reaction can be a solvent that does not markedly inhibit the reaction. Examples thereof can include chain or cyclic ethers such as diethyl ether, tetrahydrofuran, and dioxane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, nitriles such as acetonitrile, esters such as ethyl acetate, organic acids such as formic acid and acetic acid, and polar solvents such as N,N-dimethylformamide, N,N-dimethylacetamide, 1,3-dimethyl-2-imidazolidinone, and water. These inert solvents can each be used singly or can be used as a mixture of two or more thereof. The amount of the inert solvent used is not particularly limited as long as the amount allows a reaction reagent to be dissolved. The amount can be appropriately selected from the range of 0.5 L to 100 L per mol of the compound represented by the general formula (1-3).

The reaction temperature in the reaction can be appropriately selected from the range of −10° C. to the reflux temperature of the inert solvent used. The reaction time varies depending on a reaction scale, the reaction temperature, etc. and is thus not constant. The reaction time can be appropriately selected from the range of several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method 3

The compound represented by the general formula (1-5) of the present invention can be produced by the following step [d] from a compound represented by the general formula (1-3) of the present invention.

[Formula 4]

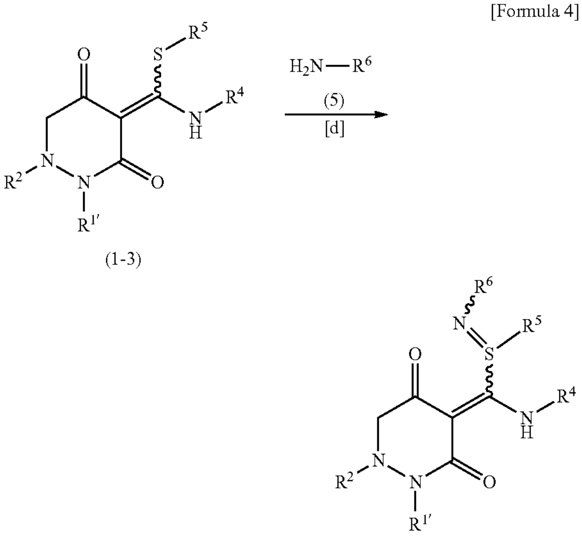

(1-3)

(1-5)

wherein $R^2$, $R^4$, $R^5$, $R^6$ and $R^{1'}$ are the same as above.

Production Method of Step [d]

The compound represented by the general formula (1-5) of the present invention can be produced by reacting the compound represented by the general formula (1-3) with an oxidizing agent and a compound represented by the general formula (5) in an inert solvent.

Examples of the oxidizing agent for use in this reaction can include bisacetoxyiodobenzene, N-chlorosuccinimide, and N-bromosuccinimide. The amount of the oxidizing agent used can be appropriately selected from the range of 1 to 5 times the mol of the compound represented by the general formula (1-3).

The inert solvent that can be used in this reaction can be a solvent that does not markedly inhibit the reaction. Examples thereof can include chain or cyclic ethers such as diethyl ether, tetrahydrofuran, and dioxane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, nitriles such as acetonitrile, esters such as ethyl acetate, organic acids such as formic acid and acetic acid, and polar solvents such as N,N-dimethylformamide, N,N-dimethylacetamide, 1,3-dimethyl-2-imidazolidinone, and water. These inert solvents can each be used singly or can be used as a mixture of two or more thereof. The amount of the inert solvent used is not particularly limited as long as the amount allows a reaction reagent to be dissolved. The amount can be appropriately selected from the range of 0.5 L to 100 L per mol of the compound represented by the general formula (1-3).

Since this reaction is equimolar reaction, each compound can be used in an equimolar amount, or an excess of any compound may be used. The reaction temperature in the reaction can be appropriately selected from the range of −10° C. to the reflux temperature of the inert solvent used, and the reaction time varies depending on a reaction scale, the reaction temperature, etc. and is thus not constant. The reaction time can be appropriately selected from the range of several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method 4

The compound represented by the general formula (1-5) of the present invention can be produced by the following step [e] from a compound represented by the general formula (1-3) of the present invention.

[Formula 5]

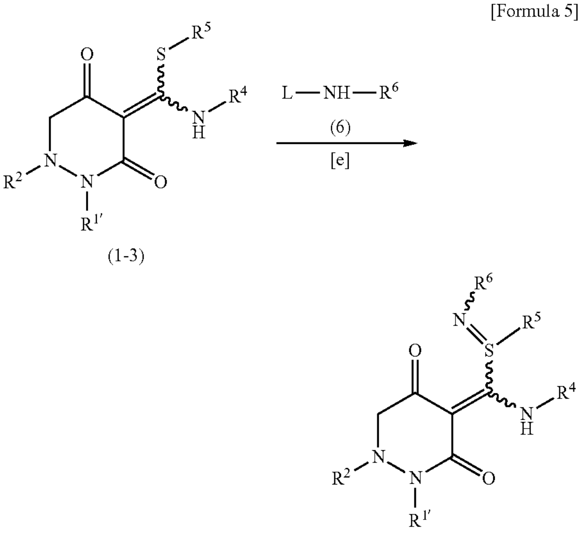

(1-3)

(1-5)

wherein $R^2$, $R^4$, $R^5$, $R^6$, $R^{1'}$ and L are the same as above.

Production Method of Step [e]

The compound represented by the general formula (1-5) of the present invention can be produced by reacting the compound represented by the general formula (1-3) with a compound represented by the general formula (6) in an inert solvent.

The inert solvent that can be used in this reaction can be a solvent that does not markedly inhibit the reaction. Examples thereof can include chain or cyclic ethers such as diethyl ether, tetrahydrofuran, and dioxane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, nitriles such as acetonitrile, esters such as ethyl acetate, organic acids such as formic acid and acetic acid, and polar solvents such as N,N-dimethylformamide, N,N-dimethylacetamide, 1,3-dimethyl-2-imidazolidinone, alcohols such as methanol, ethanol, propanol, butanol, and 2-propanol, and water. These inert solvents can each be used singly or can be used as a mixture of two or more thereof. The amount of the inert solvent used is not particularly limited as long as the amount allows a reaction reagent to be dissolved. The amount can be appropriately selected from the range of 0.5 L to 100 L per mol of the compound represented by the general formula (1-3).

Since this reaction is equimolar reaction, each compound can be used in an equimolar amount, or an excess of any compound may be used. The reaction temperature in the reaction can be appropriately selected from the range of 0° C. to the reflux temperature of the inert solvent used, and the reaction time varies depending on a reaction scale, the reaction temperature, etc. and is thus not constant. The reaction time can be appropriately selected from the range of several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method 5

The compound represented by the general formula (1-6) of the present invention can be produced by the following step [f] from a compound represented by the general formula (1-3) of the present invention.

[Formula 6]

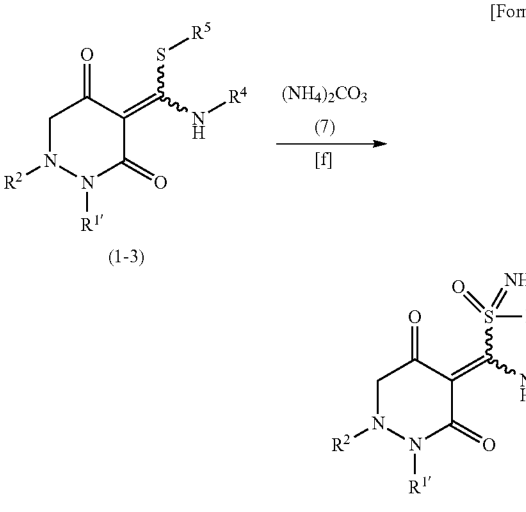

(1-3)

(1-6)

wherein $R^2$, $R^4$, $R^5$ and $R^{1'}$ are the same as above.

Production Method of Step [f]

The compound represented by the general formula (1-6) of the present invention can be produced by reacting the compound represented by the general formula (1-3) with an oxidizing agent and ammonium carbonate (7) in an inert solvent.

Examples of the oxidizing agent for use in this reaction can include bisacetoxyiodobenzene, N-chlorosuccinimide, and N-bromosuccinimide. The amount of the oxidizing agent used can be appropriately selected from the range of 1 to 5 times the mol of the compound represented by the general formula (1-3).

The inert solvent that can be used in this reaction can be a solvent that does not markedly inhibit the reaction. Examples thereof can include chain or cyclic ethers such as diethyl ether, tetrahydrofuran, and dioxane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, nitriles such as acetonitrile, esters such as ethyl acetate, organic acids such as formic acid and acetic acid, and polar solvents such as N,N-dimethylformamide, N,N-dimethylacetamide, 1,3-dimethyl-2-imidazolidinone, alcohols such as methanol, ethanol, propanol, butanol, and 2-propanol, and water. These inert solvents can each be used singly or can be used as a mixture of two or more thereof. The amount of the inert solvent used is not particularly limited as long as the amount allows a reaction reagent to be dissolved. The amount can be appropriately selected from the range of 0.5 L to 100 L per mol of the compound represented by the general formula (1-3).

Since this reaction is equimolar reaction, each compound can be used in an equimolar amount, or an excess of any compound may be used. The reaction temperature in the reaction can be appropriately selected from the range of 0° C. to the reflux temperature of the inert solvent used, and the reaction time varies depending on a reaction scale, the reaction temperature, etc. and is thus not constant. The reaction time can be appropriately selected from the range of several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method 6

The compound represented by the general formula (1-7) of the present invention can be produced by the following step [g] from a compound represented by the general formula (1-2) of the present invention.

[Formula 7]

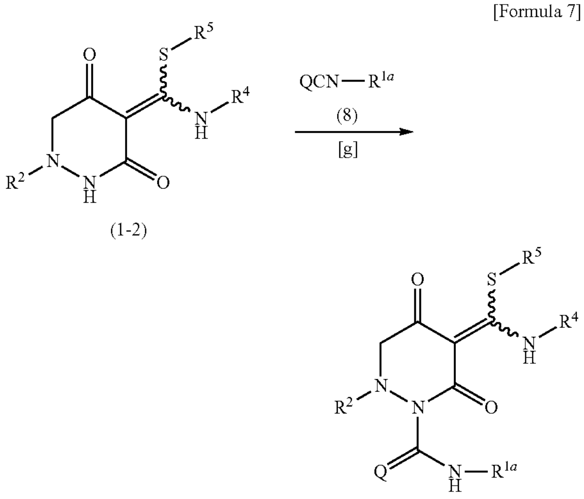

(1-2)

(1-7)

wherein $R^2$, $R^4$ and $R^5$ are the same as above; Q represents an oxygen atom or a sulfur atom; and $R^{1a}$ represents a $(C_1\text{-}C_6)$ alkyl group, a halo $(C_1\text{-}C_6)$ alkyl group, a $(C_2\text{-}C_6)$ alkenyl group, a $(C_2\text{-}C_6)$ alkynyl group, a $(C_3\text{-}C_6)$ cycloalkyl group, a $(C_1\text{-}C_6)$ alkoxy group, a $(C_1\text{-}C_6)$ alkoxy $(C_1\text{-}C_6)$ alkyl group, a $(C_1\text{-}C_6)$ alkylsulfanyl $(C_1\text{-}C_6)$ alkyl group, a phenyl $(C_1\text{-}C_6)$ alkyl group, a substituted phenyl $(C_1\text{-}C_6)$ alkyl group having one to three substituents each independently selected from the group consisting of a halogen atom, a cyano group, a nitro group and a $(C_1\text{-}C_6)$ alkyl group, a phenyl group, or a substituted phenyl group having one to three substituents each independently selected from the group consisting of a halogen atom, a cyano group and a $(C_1\text{-}C_6)$ alkyl group.

Production Method of Step [g]

The compound represented by the general formula (1-7) of the present invention can be produced by reacting the compound represented by the general formula (1-2) of the present invention with a compound represented by the general formula (8) in the presence of a base and an inert solvent.

Examples of the base that can be used in this reaction can include hydroxides such as lithium hydroxide, sodium hydroxide, potassium hydroxide, and calcium hydroxide, alkoxides such as sodium methoxide, sodium ethoxide, sodium tertiary butoxide, and potassium tertiary butoxide, alkali metal hydrides such as sodium hydride and potassium hydride, carbonates such as lithium carbonate, lithium bicarbonate, sodium carbonate, sodium bicarbonate, potassium carbonate, potassium bicarbonate, calcium carbonate, magnesium carbonate, and cesium carbonate, acetates such as lithium acetate, sodium acetate, and potassium acetate, and organic bases including pyridine, picoline, lutidine, triethylamine, tributylamine, and N,N-diisopropylethylamine. The amount of the base used is in the range of usually 1 to 10 times the mol of the compound represented by the general formula (1-2).

The inert solvent that can be used in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, aprotic polar solvents such as N,N-dimethylformamide, N,N-dimethylacetamide, dimethyl sulfoxide, and 1,3-dimethyl-2-imidazolidinone, and alcohols such as methanol, ethanol, propanol, butanol, and 2-propanol. These inert solvents can each be used singly or can be used as a mixture of two or more thereof. The amount of the solvent used can be appropriately selected from the range of usually 0.1 to 100 L per mol of the compound represented by the general formula (1-2).

Since this reaction is equimolar reaction, each compound can be used in an equimolar amount, or an excess of any compound may be used. The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method 7

The compound represented by the general formula (1-3) of the present invention can be produced by the following step [a] from a compound represented by the general formula (1-2). The reaction conditions is the same as above.

[Formula 8]

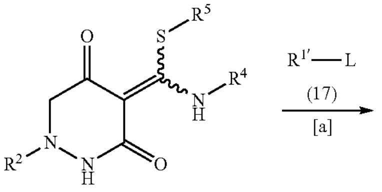

(1-2)

-continued

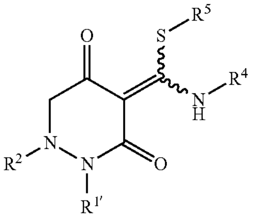

(1-3)

wherein $R^1$, $R^2$, $R^4$ and $R^5$ are the same as above; and L represents a leaving group, for example, chlorine, bromine, iodine, a ($C_1$-$C_6$) alkylcarbonyloxy group, or a ($C_1$-$C_6$) alkoxycarbonyloxy group.

Production Method 1 of Starting Material

The compound represented by the general formula (2) which is a starting material can be produced by the following production method, i.e., by the following steps [h], [i], [j], [k] and [g] from a compound represented by the general formula (9). The reaction conditions of the step [g] are the same as above. The compound represented by the general formula (13) may be produced in accordance with a method described in International Publication No. WO 2021/261563.

[Formula 9]

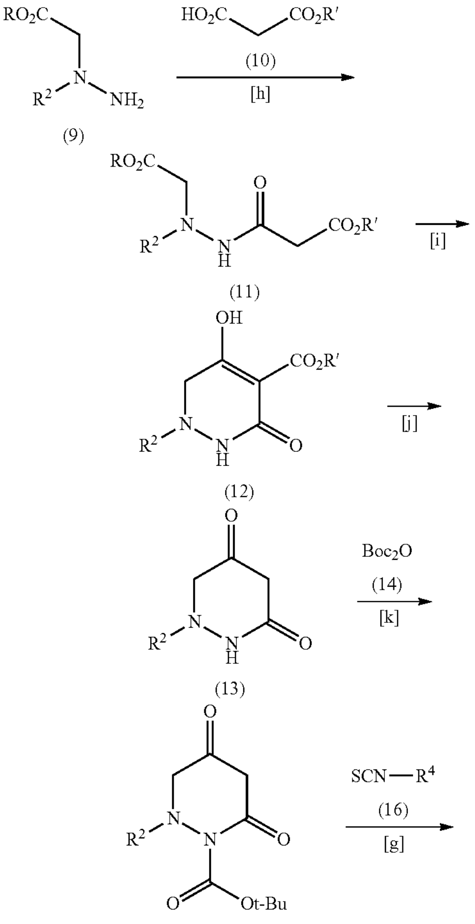

-continued

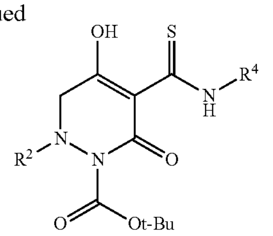

(2)

wherein $R^2$ and $R^4$ are the same as above; and R and R' each represent a ($C_1$-$C_6$) alkyl group, for example, a methyl group or an ethyl group.

Production Method of Step [h]

The compound represented by the general formula (11) can be produced by condensing the compound represented by the general formula (9) with a compound represented by the general formula (10) by an amidation method that is generally used in organic synthesis.

Production Method of Step [i]

The compound represented by the general formula (12) can be produced by subjecting the compound represented by the general formula (11) to cyclization reaction in the presence of a base and an inert solvent.

Examples of the base for use in this reaction can include hydroxides such as lithium hydroxide, sodium hydroxide, potassium hydroxide, and calcium hydroxide, alkoxides such as sodium methoxide, sodium ethoxide, sodium tertiary butoxide, and potassium tertiary butoxide, alkali metal hydrides such as sodium hydride and potassium hydride, carbonates such as lithium carbonate, lithium bicarbonate, sodium carbonate, sodium bicarbonate, potassium carbonate, potassium bicarbonate, calcium carbonate, and magnesium carbonate, acetates such as lithium acetate, sodium acetate, and potassium acetate, and organic bases including pyridine, picoline, lutidine, triethylamine, tributylamine, and diisopropylethylamine. The amount of the base used is in the range of usually 1 to 10 times the mol of the compound represented by the general formula (11).

The inert solvent for use in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, aprotic polar solvents such as N,N-dimethylformamide, N,N-dimethylacetamide, dimethyl sulfoxide, and 1,3-dimethyl-2-imidazolidinone, and alcohols such as methanol, ethanol, propanol, butanol, and 2-propanol. These inert solvents can each be used singly or can be used as a mixture of two or more thereof. The amount of the solvent used can be appropriately selected from the range of usually 0.1 to 100 L per mol of the compound represented by the general formula (11).

The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest.

Production Method of Step [j]

The compound represented by the general formula (13) can be produced by reacting the compound represented by the general formula (12) under heating conditions in the presence of an inert solvent.

The inert solvent for use in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, aprotic polar solvents such as N,N-dimethylformamide, N,N-dimethylacetamide, dimethyl sulfoxide, and 1,3-dimethyl-2-imidazolidinone, alcohols such as methanol, ethanol, propanol, butanol, and 2-propanol, and water. These inert solvents can each be used singly or can be used as a mixture of two or more thereof. The amount of the solvent used can be appropriately selected from the range of usually 0.1 to 100 L per mol of the compound represented by the general formula (12).

The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest. Alternatively, the reaction solution may be subjected to the next step without isolation.

Production Method of Step [k]

The compound represented by the general formula (15) can be produced by reacting the compound represented by the general formula (13) with a compound represented by di-tertiary butyl dicarbonate (6) in the presence of a base and an inert solvent.

Examples of the base that can be used in this reaction can include inorganic bases including hydroxides of alkali metal atoms such as sodium hydroxide and potassium hydroxide, hydrides of alkali metals such as sodium hydride and potassium hydride, alkali metal salts of alcohols such as sodium ethoxide and potassium t-butoxide, and carbonates such as sodium carbonate, potassium carbonate, and sodium bicarbonate, and organic bases including triethylamine, pyridine, N,N-dimethyl-4-aminopyridine, and DBU. The amount of the base used is in the range of usually 1 to 10 times the mol of the compound represented by the general formula (13).

The inert solvent that can be used in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, esters such as methyl acetate, ketones such as acetone and methyl ethyl ketone, aprotic polar solvents such as N,N-dimethylformamide, N,N-dimethylacetamide, dimethyl sulfoxide, and 1,3-dimethyl-2-imidazolidinone, and alcohols such as methanol, ethanol, propanol, butanol, and 2-propanol. These inert solvents can each be used singly or can be used as a mixture of two or more thereof. The amount of the solvent used can be appropriately selected from the range of usually 0.1 to 100 L per mol of the compound represented by the general formula (13).

Since this reaction is equimolar reaction, each compound can be used in an equimolar amount, or an excess of any compound may be used. The reaction temperature in the reaction can be in the range of usually 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest. Alternatively, the reaction solution may be subjected to the next step without isolation.

Production Method 2 of Starting Material

The compound represented by the general formula (4) which is a starting material can be produced by the following production method, i.e., by the following steps [a] and [g] from a compound represented by the general formula (13). The reaction conditions of the steps [a] and [g] are the same as above.

[Formula 10]

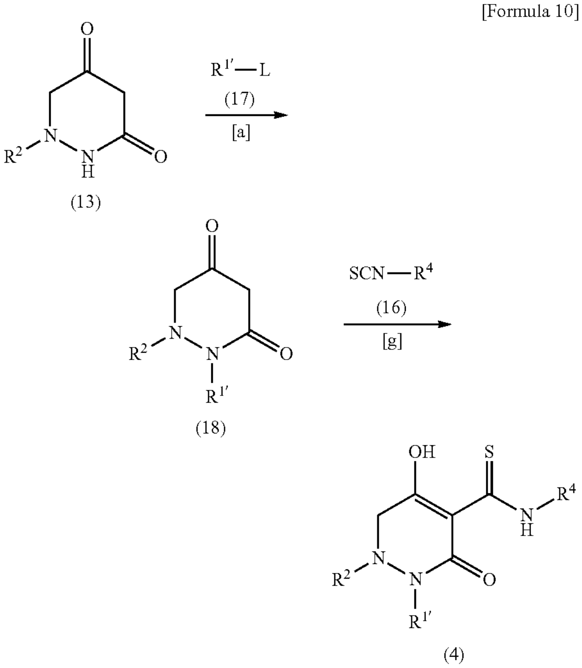

wherein $R^{1'}$, $R^2$ and $R^4$ are the same as above; and L represents a leaving group, for example, chlorine, bromine, iodine, a ($C_1$-$C_6$) alkylcarbonyloxy group, or a ($C_1$-$C_6$) alkoxycarbonyloxy group.

Production Method 3 of Starting Material

The compound represented by the general formula (9) can be produced by the following production method, i.e., by the following steps [l] and [m] from a compound represented by the general formula (19).

[Formula 11]

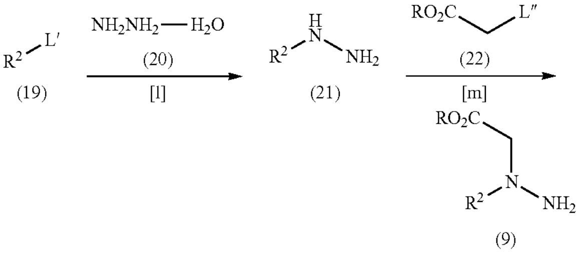

wherein $R^2$ and R are the same as above; and L' and L" each represent a leaving group, for example, fluorine, chlorine, bromine, or iodine.

Production Method of Step [l]

The compound represented by the general formula (21) can be produced by reacting the compound represented by the general formula (19) with hydrazine monohydrate represented by the formula (20) in the presence of an inert solvent.

The inert solvent for use in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated aromatic hydrocarbons such as chlorobenzene and dichlorobenzene, chain or cyclic ethers such as diethyl ether, methyl tertiary butyl ether, dioxane, and tetrahydrofuran, and alcohols such as methanol, ethanol, propanol, butanol, and 2-propanol. These inert solvents can each be used singly or can be used as a mixture of two or more thereof. The amount of the solvent used can be appropriately selected from the range of usually 0.1 to 100 L per mol of the compound represented by the general formula (19).

Since this reaction is equimolar reaction, each compound can be used in an equimolar amount, or an excess of any compound may be used. The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest. Alternatively, the reaction solution may be subjected to the next step without isolation.

Production Method of Step [m]

The compound represented by the general formula (9) can be produced by reacting the compound represented by the general formula (21) with a compound represented by the general formula (22) in the presence of a base and an inert solvent. In accordance with a method described in International Publication No. WO 2021/261563, a group represented by —$NH_2$ in the compound represented by the general formula (21) may be protected through reaction with a compound represented by R"—C(═O)—R" (wherein R" independently represents a ($C_1$-$C_6$) alkyl group such as a methyl group or an ethyl group, a phenyl group, or the like), and the step [m] can then be performed, followed by deprotection.

Examples of the base for use in this reaction can include hydroxides such as lithium hydroxide, sodium hydroxide, potassium hydroxide, and calcium hydroxide, alkoxides such as sodium methoxide, sodium ethoxide, sodium tertiary butoxide, and potassium tertiary butoxide, alkali metal hydrides such as sodium hydride and potassium hydride, carbonates such as lithium carbonate, lithium bicarbonate, sodium carbonate, sodium bicarbonate, potassium carbonate, potassium bicarbonate, calcium carbonate, magnesium carbonate, and cesium carbonate, acetates such as lithium acetate, sodium acetate, and potassium acetate, and organic bases including pyridine, picoline, lutidine, triethylamine, tributylamine, and N,N-diisopropylethylamine. The amount of the base used is in the range of usually 1 to 10 times the mol of the compound represented by the general formula (21).

The inert solvent for use in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, and aprotic polar solvents such as N,N-dimethylformamide, N,N-dimethylacetamide, dimethyl sulfoxide, and 1,3-dimethyl-2-imidazolidinone. These inert solvents can each be used singly or can be used as a mixture of two or more thereof. The amount of the solvent used can be appropriately selected from the range of usually 0.1 to 100 L per mol of the compound represented by the general formula (21).

Since this reaction is equimolar reaction, each compound can be used in an equimolar amount, or an excess of any compound may be used. The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest. Alternatively, the reaction solution may be subjected to the next step without isolation.

Production Method 4 of Starting Material

The compound represented by the general formula (9) can also be produced by the following production method, i.e., by the following step [n] from a compound represented by the general formula (19).

[Formula 12]

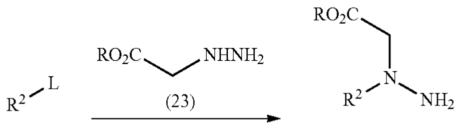

(19) (9)

wherein $R^2$, R and L are the same as above.

Production Method of Step [n]

The compound represented by the general formula (9) can be produced by reacting the compound represented by the general formula (19) with a compound represented by the general formula (23) in the presence of a base and an inert solvent. In accordance with a method described in International Publication No. WO 2021/261563, a group represented by —$NH_2$ in the compound represented by the general formula (23) may be protected through reaction with a compound represented by R"—C(═O)—R" (wherein R" independently represents a ($C_1$-$C_6$) alkyl group such as a methyl group or an ethyl group, a phenyl group, or the like), and the step [n] can then be performed, followed by deprotection.

Examples of the base that can be used in this reaction can include hydroxides such as lithium hydroxide, sodium hydroxide, potassium hydroxide, and calcium hydroxide, alkoxides such as sodium methoxide, sodium ethoxide, sodium tertiary butoxide, and potassium tertiary butoxide, alkali metal hydrides such as sodium hydride and potassium hydride, carbonates such as lithium carbonate, lithium bicarbonate, sodium carbonate, sodium bicarbonate, potassium carbonate, potassium bicarbonate, calcium carbonate, magnesium carbonate, and cesium carbonate, acetates such as lithium acetate, sodium acetate, and potassium acetate, and organic bases including pyridine, picoline, lutidine, triethylamine, tributylamine, and N,N-diisopropylethylamine. The amount of the base used is in the range of usually 1 to 10 times the mol of the compound represented by the general formula (19).

The inert solvent that can be used in this reaction can be a solvent that does not markedly inhibit the progression of the reaction. Examples thereof can include chain or cyclic saturated hydrocarbons such as pentane, hexane, and cyclohexane, aromatic hydrocarbons such as benzene, toluene, and xylene, halogenated hydrocarbons such as methylene chloride, chloroform, and carbon tetrachloride, halogenated aromatic hydrocarbons such as chlorobenzene and dichlorobenzene, chain or cyclic ethers such as diethyl ether, methyl tertiary butyl ether, dioxane, and tetrahydrofuran, nitriles such as acetonitrile and propionitrile, esters such as methyl acetate, ketones such as acetone and methyl ethyl ketone, aprotic polar solvents such as N,N-dimethylformamide, N,N-dimethylacetamide, dimethyl sulfoxide, and 1,3-dimethyl-2-imidazolidinone, and alcohols such as methanol, ethanol, propanol, butanol, and 2-propanol. These inert solvents can each be used singly or can be used as a mixture of two or more thereof. The amount of the solvent used can be appropriately selected from the range of usually 0.1 to 100 L per mol of the compound represented by the general formula (19).

Since this reaction is equimolar reaction, each compound can be used in an equimolar amount, or an excess of any compound may be used. The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest. Alternatively, the reaction solution may be subjected to the next step without isolation.

Production Method 5 of Starting Material

The compound represented by the general formula (9) can also be produced by the following production method, i.e., by the following steps [m] and [o] from a compound represented by the general formula (24). The reaction conditions of the step [m] are the same as above.

[Formula 13]

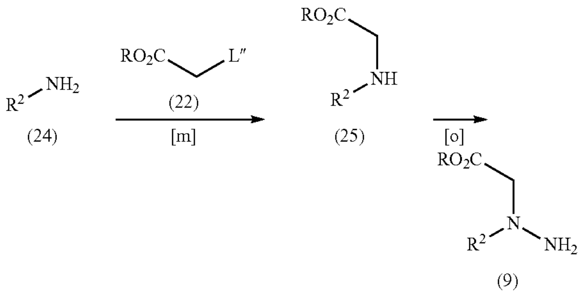

wherein $R^2$, R and L" are the same as above.

Production Method of Step [o]

The compound represented by the general formula (9) can be produced by reacting the compound represented by the general formula (25) with sodium nitrite in the presence of an acid, followed by reduction with a reducing agent.

Examples of the acid that can be used in this reaction can include inorganic acids such as hydrochloric acid, sulfuric acid, and nitric acid, and organic acids such as formic acid, acetic acid, propionic acid, trifluoroacetic acid, and benzoic acid. The amount of the acid used can be appropriately selected in the range of 0.01 to 10 times the mol of the compound represented by the general formula (25). The acid may be used as a solvent.

Examples of the reducing agent for use in this reaction can include sodium sulfite and tin chloride. The amount of the reducing agent used can be appropriately selected from the range of usually 1.0 to 10 times the mol of the compound represented by the general formula (25).

The reaction temperature in the reaction can be in the range of usually approximately 0° C. to the boiling point of the solvent used, and the reaction time varies depending on a reaction scale, the reaction temperature, etc. and is thus not constant. The reaction time can be appropriately selected from the range of usually several minutes to 48 hours. After the completion of reaction, the compound of interest can be isolated by a routine method from the reaction system containing the compound of interest, and can be purified, if necessary, by recrystallization, column chromatography, or the like to produce the compound of interest. Alternatively, the reaction solution may be subjected to the next step without isolation.

Hereinafter, typical examples of the compound represented by the general formula (1) of the present invention will be listed in Tables 1 to 4, though the present invention is not limited by these examples. Also, typical examples of the compound (21) and the compound (9) will be listed in Tables 5 and 6, respectively.

In the tables, the term "Me" represents a methyl group, the term "Et" represents an ethyl group, the term "c-Pr" represents a cyclopropyl group, the term "n-Pr" represents a normal propyl group, the term "t-Bu" represents a tertiary butyl group, the term "Ac" represents an acetyl group, the term "Bn" represents a benzyl group, and the term "TMS" represents a trimethylsilyl group. Physical properties are indicated by a melting point (° C.), a refractive index, or $H^1$-NMR. The $H^1$-NMR data is shown in Table 7.

[Formula 14]

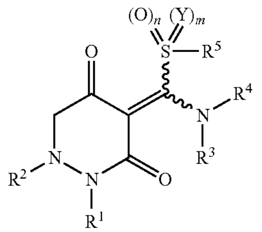

(1)

TABLE 1

(In Table 1, $R^3$ represents a hydrogen atom, n represents 0, and m represents 0.)

| Compound No. | $R^1$ | $R^2$ | $R^4$ | $R^5$ | Physical property value |
|---|---|---|---|---|---|
| 1-1 | H | 6-$CF_3$-pyridin-3-yl | 4-F-Ph | Me | 158-159 |
| 1-2 | H | 6-$CF_3$-pyridin-3-yl | 4-F-Ph | Et | 93-95 |
| 1-3 | H | 6-$CF_3$-pyridin-3-yl | 4-F-Ph | $CH_2CN$ | 138-140 |
| 1-4 | H | 6-$CF_3$-pyridin-3-yl | 4-F-Ph | $CH_2CF_3$ | 192-194 |
| 1-5 | H | 6-$CF_3$-pyridin-3-yl | 4-F-Ph | $CH_2CH{=}CH_2$ | 128-130 |
| 1-6 | H | 6-$CF_3$-pyridin-3-yl | 4-F-Ph | 4-t-Bu-Bn | 59-61 |
| 1-7 | H | 6-$CF_3$-pyridin-3-yl | 4-F-Ph | 4-Cl-Bn | 57-60 |
| 1-8 | H | 6-$CF_3$-pyridin-3-yl | 4-F-Ph | 3-Cl-Bn | 88-91 |
| 1-9 | Ac | 6-$CF_3$-pyridin-3-yl | 4-F-Ph | Me | |
| 1-10 | Ac | 6-CN-pyridin-3-yl | 4-F-Ph | Me | |
| 1-11 | $CO_2Me$ | 3-F-4-CN-Ph | 4-F-Ph | Me | |
| 1-12 | $CO_2Me$ | 3-Me-4-CN-Ph | 4-F-Ph | Me | 111-114 |
| 1-13 | $CO_2Me$ | 3-OMe-4-CN-Ph | 4-F-Ph | Me | |
| 1-14 | $CO_2Me$ | 4-CN-Ph | 4-F-Ph | Me | 194-196 |
| 1-15 | $CO_2Me$ | 5-Cl-6-CN-pyridin-3-yl | 4-F-Ph | Me | 116-120 |
| 1-16 | $CO_2Me$ | 5-Me-6-CN-pyridin-3-yl | 4-F-Ph | Me | 166-169 |
| 1-17 | $CO_2Me$ | 6-Br-pyridin-3-yl | 4-F-Ph | Me | 128-129 |
| 1-18 | $CO_2Me$ | 6-Cl-pyridin-3-yl | 4-F-Ph | Me | 112-113 |
| 1-19 | $CO_2Me$ | 6-CN-pyridin-3-yl | Me | Me | |
| 1-20 | $CO_2Me$ | 6-CN-pyridin-3-yl | c-Pr | Me | |
| 1-21 | $CO_2Me$ | 6-CN-pyridin-3-yl | $CH_2CH_2OMe$ | Me | |

TABLE 1-continued (In Table 1, $R^3$ represents a hydrogen atom, n represents 0, and m represents 0.)

| Compound No. | $R^1$ | $R^2$ | $R^4$ | $R^5$ | Physical property value |
|---|---|---|---|---|---|
| 1-22 | $CO_2Me$ | 6-CN-pyridin-3-yl | $CH_2C{\equiv}CH$ | Me | |
| 1-23 | $CO_2Me$ | 6-CN-pyridin-3-yl | 6-OMe-pyridin-3-yl | Me | |
| 1-24 | $CO_2Me$ | 6-CN-pyridin-3-yl | 6-F-pyridin-3-yl | Me | 184-187 |
| 1-25 | $CO_2Me$ | 6-CN-pyridin-3-yl | 6-Cl-pyridin-3-yl | Me | 192-194 |
| 1-26 | $CO_2Me$ | 6-CN-pyridin-3-yl | 5-F-pyridin-2-yl | Me | |
| 1-27 | $CO_2Me$ | 6-CN-pyridin-3-yl | 5-Cl-pyridin-2-yl | Me | |
| 1-28 | $CO_2Me$ | 6-CN-pyridin-3-yl | 4-Me-Ph | Me | 136-139 |
| 1-29 | $CO_2Me$ | 6-CN-pyridin-3-yl | 4-F-Ph | Me | 185-187 |
| 1-30 | $CO_2Me$ | 6-CN-pyridin-3-yl | 4-F-Ph | Et | 150-152 |
| 1-31 | $CO_2Me$ | 6-CN-pyridin-3-yl | 4-F-Ph | $CH_2CN$ | |
| 1-32 | $CO_2Me$ | 6-CN-pyridin-3-yl | 4-F-Ph | $CH_2CF_3$ | |
| 1-33 | $CO_2Me$ | 6-CN-pyridin-3-yl | 4-F-Ph | $CH_2CH{=}CH_2$ | |
| 1-34 | $CO_2Me$ | 6-CN-pyridin-3-yl | 4-F-Ph | Bn | 137-141 |
| 1-35 | $CO_2Me$ | 6-CN-pyridin-3-yl | 4-F-Ph | 4-t-Bu-Bn | 156-158 |
| 1-36 | $CO_2Me$ | 6-CN-pyridin-3-yl | 4-F-Ph | 4-Cl-Bn | 161-163 |
| 1-37 | $CO_2Me$ | 6-CN-pyridin-3-yl | 4-F-Ph | 3-Cl-Bn | |
| 1-38 | $CO_2Me$ | 6-CN-pyridin-3-yl | 4-F-Ph | 2-Cl-Bn | 142-146 |
| 1-39 | $CO_2Me$ | 6-CN-pyridin-3-yl | 4-CN-Ph | Me | 193-195 |
| 1-40 | $CO_2Me$ | 6-CN-pyridin-3-yl | 4-Cl-Ph | Me | 166-169 |
| 1-41 | $CO_2Me$ | 6-CN-pyridin-3-yl | 3-Me-4-F-Ph | Me | 174-177 |
| 1-42 | $CO_2Me$ | 6-CN-pyridin-3-yl | 3,4-$F_2$-Ph | Me | 194-196 |
| 1-43 | COc-Pr | 6-$CF_3$-pyridin-3-yl | 4-F-Ph | Me | |
| 1-44 | COc-Pr | 6-CN-pyridin-3-yl | 4-F-Ph | Me | 207-208 |
| 1-45 | $CO_2$t-Bu | 3-F-4-CN-Ph | 4-F-Ph | Me | |
| 1-46 | $CO_2$t-Bu | 3-Me-4-CN-Ph | 4-F-Ph | Me | |
| 1-47 | $CO_2$t-Bu | 3-OMe-4-CN-Ph | 4-F-Ph | Me | |
| 1-48 | $CO_2$t-Bu | 4-CN-Ph | 4-F-Ph | Me | |
| 1-49 | $CO_2$t-Bu | 5-Cl-6-CN-pyridin-3-yl | 4-F-Ph | Me | |
| 1-50 | $CO_2$t-Bu | 5-Me-6-CN-pyridin-3-yl | 4-F-Ph | Me | |
| 1-51 | $CO_2$t-Bu | 6-Br-pyridin-3-yl | 4-F-Ph | Me | |
| 1-52 | $CO_2$t-Bu | 6-$CF_3$-pyridin-3-yl | Me | Me | |
| 1-53 | $CO_2$t-Bu | 6-$CF_3$-pyridin-3-yl | c-Pr | Me | NMR |
| 1-54 | $CO_2$t-Bu | 6-$CF_3$-pyridin-3-yl | c-Pr | Bn | 66-68 |
| 1-55 | $CO_2$t-Bu | 6-$CF_3$-pyridin-3-yl | $CH_2CH_2OMe$ | Me | |
| 1-56 | $CO_2$t-Bu | 6-$CF_3$-pyridin-3-yl | $CH_2C{\equiv}CH$ | Me | |
| 1-57 | $CO_2$t-Bu | 6-$CF_3$-pyridin-3-yl | 6-OMe-pyridin-3-yl | Me | |
| 1-58 | $CO_2$t-Bu | 6-$CF_3$-pyridin-3-yl | 6-F-pyridin-3-yl | Me | |
| 1-59 | $CO_2$t-Bu | 6-$CF_3$-pyridin-3-yl | 6-Cl-pyridin-3-yl | Me | |
| 1-60 | $CO_2$t-Bu | 6-$CF_3$-pyridin-3-yl | 5-F-pyridin-2-yl | Me | |
| 1-61 | $CO_2$t-Bu | 6-$CF_3$-pyridin-3-yl | 5-Cl-pyridin-2-yl | Me | |
| 1-62 | $CO_2$t-Bu | 6-$CF_3$-pyridin-3-yl | 4-Me-Ph | Me | |
| 1-63 | $CO_2$t-Bu | 6-$CF_3$-pyridin-3-yl | 4-F-Ph | Me | NMR |
| 1-64 | $CO_2$t-Bu | 6-$CF_3$-pyridin-3-yl | 4-F-Ph | Et | 118-122 |
| 1-65 | $CO_2$t-Bu | 6-$CF_3$-pyridin-3-yl | 4-F-Ph | $CH_2CN$ | 116-120 |
| 1-66 | $CO_2$t-Bu | 6-$CF_3$-pyridin-3-yl | 4-F-Ph | $CH_2CF_3$ | 149-151 |
| 1-67 | $CO_2$t-Bu | 6-$CF_3$-pyridin-3-yl | 4-F-Ph | $CH_2CH{=}CH_2$ | 85-87 |
| 1-68 | $CO_2$t-Bu | 6-$CF_3$-pyridin-3-yl | 4-F-Ph | 4-t-Bu-Bn | 38-42 |
| 1-69 | $CO_2$t-Bu | 6-$CF_3$-pyridin-3-yl | 4-F-Ph | 4-Cl-Bn | 138-140 |
| 1-70 | $CO_2$t-Bu | 6-$CF_3$-pyridin-3-yl | 4-F-Ph | 3-Cl-Bn | 137-140 |
| 1-71 | $CO_2$t-Bu | 6-$CF_3$-pyridin-3-yl | 4-F-Ph | 2-Cl-Bn | 1.4656(18.0° C.) |
| 1-72 | $CO_2$t-Bu | 6-$CF_3$-pyridin-3-yl | 4-CN-Ph | Me | |
| 1-73 | $CO_2$t-Bu | 6-$CF_3$-pyridin-3-yl | 4-Cl-Ph | Me | |
| 1-74 | $CO_2$t-Bu | 6-$CF_3$-pyridin-3-yl | 3-Me-4-F-Ph | Me | |
| 1-75 | $CO_2$t-Bu | 6-$CF_3$-pyridin-3-yl | 3,4-$F_2$-Ph | Me | |
| 1-76 | $CO_2$t-Bu | 6-Cl-pyridin-3-yl | 4-F-Ph | Me | |
| 1-77 | $CO_2CH_2CH_2OMe$ | 6-$CF_3$-pyridin-3-yl | 4-F-Ph | Me | |
| 1-78 | $CO_2CH_2CH_2OMe$ | 6-CN-pyridin-3-yl | 4-F-Ph | Me | 106-108 |
| 1-79 | CONHEt | 6-$CF_3$-pyridin-3-yl | 4-F-Ph | Me | |
| 1-80 | CONHEt | 6-CN-pyridin-3-yl | 4-F-Ph | Me | |
| 1-81 | CONH(c-Pr) | 6-$CF_3$-pyridin-3-yl | 4-F-Ph | Me | |
| 1-82 | CONH(c-Pr) | 6-CN-pyridin-3-yl | 4-F-Ph | Me | |
| 1-83 | CSNHEt | 6-$CF_3$-pyridin-3-yl | 4-F-Ph | Me | |
| 1-84 | CSNHEt | 6-CN-pyridin-3-yl | 4-F-Ph | Me | |
| 1-85 | CSNH(c-Pr) | 6-$CF_3$-pyridin-3-yl | 4-F-Ph | Me | |
| 1-86 | CSNH(c-Pr) | 6-CN-pyridin-3-yl | 4-F-Ph | Me | |
| 1-87* | $CO_2Me$ | 6-CN-pyridin-3-yl | 4-F-Ph | Me | 199-209 |
| 1-88* | $CO_2CH_2CH_2OMe$ | 6-CN-pyridin-3-yl | 4-F-Ph | Me | 265-267 |
| 1-89 | $CO_2Me$ | 6-CN-pyridin-3-yl | 3,5-$F_2$-Ph | Me | 171-174 |
| 1-90 | $CO_2Me$ | 6-CN-pyridin-3-yl | Ph | Me | 186-189 |
| 1-91 | $CO_2Me$ | 6-CN-pyridin-3-yl | 3-Me-Ph | Me | 124-127 |
| 1-92 | $CO_2Me$ | 6-CN-pyridin-3-yl | 4-SMe-Ph | Me | 125-128 |
| 1-93 | $CO_2Me$ | 6-CN-pyridin-3-yl | 4-F-Ph | 4-F-Bn | 149-151 |
| 1-94 | $CO_2Me$ | 6-CN-pyridin-3-yl | 4-F-Ph | 3,5-$(OMe)_2$-Bn | 150-152 |
| 1-95 | $CO_2Me$ | 6-CN-pyridin-3-yl | 4-OMe-Ph | Me | 161-164 |

TABLE 1-continued (In Table 1, $R^3$ represents a hydrogen atom, n represents 0, and m represents 0.)

| Compound No. | $R^1$ | $R^2$ | $R^4$ | $R^5$ | Physical property value |
|---|---|---|---|---|---|
| 1-96 | $CO_2Me$ | 6-CN-pyridin-3-yl | 4-$CO_2$Et-Ph | Me | 195-198 |
| 1-97 | $CO_2Me$ | 6-CN-pyridin-3-yl | 3-F-Ph | Me | 171-174 |
| 1-98 | $CO_2Me$ | 6-CN-pyridin-3-yl | 3-F-Ph | 4-CN-Bn | |
| 1-99 | $CO_2Me$ | 6-CN-pyridin-3-yl | 4-F-Ph | 4-$CO_2$Me-Bn | 131-133 |
| 1-100 | $CO_2Me$ | 6-CN-pyridin-3-yl | 4-F-Ph | 4-$CF_3$-Bn | 135-138 |
| 1-101 | $CO_2Me$ | 6-CN-pyridin-3-yl | 4-F-Ph | 4-$OCF_3$-Bn | 131-133 |
| 1-102 | $CO_2CH_2CH_2OMe$ | 6-CN-pyridin-3-yl | 4-$OCF_3$-Ph | Me | 131-135 |
| 1-103 | $CO_2Me$ | 6-CN-pyridin-3-yl | 4-F-Ph | 4-$NO_2$-Bn | 141-144 |
| 1-104 | $CO_2Me$ | 6-CN-pyridin-3-yl | 4-F-Ph | 3-Me-Bn | 135-138 |
| 1-105 | $CO_2Me$ | 6-CN-pyridin-3-yl | 4-F-Ph | 4-Br-Bn | 121-125 |
| 1-106 | H | 6-CN-pyridin-3-yl | 4-F-Ph | Me | 181-184 |
| 1-107 | $CO_2Me$ | 6-CN-pyridin-3-yl | 1-Me-pyrazol-4-yl | Me | 187-189 |
| 1-108 | $CO_2Me$ | 6-CN-pyridin-3-yl | 1-Me-pyrazol-3-yl | Me | 167-169 |
| 1-109** | $CO_2Me$ | 6-CN-pyridin-3-yl | 4-F-Ph | Me | 187-190 |
| 1-110 | $CO_2$t-Bu | 6-CN-pyridin-3-yl | 4-F-Ph | Me | 117-118 |
| 1-111 | $CO_2Me$ | 6-CN-pyridin-3-yl | 2-F-Ph | Me | 174-177 |
| 1-112 | $CO_2Me$ | 6-CN-pyridin-3-yl | 3,4,5-$F_3$-Ph | Me | 159-161 |
| 1-113 | $CO_2Me$ | 6-CN-pyridin-3-yl | 3-F-5-Cl-Ph | Me | 141-143 |
| 1-114 | $CO_2Me$ | 6-CN-pyridin-3-yl | 2-F-4-Cl-Ph | Me | |
| 1-115 | $CO_2Me$ | 6-CN-pyridin-3-yl | 4-F-Ph | (pyridin-2-yl)$CH_2$ | |
| 1-116 | $CO_2Me$ | 6-CN-pyridin-3-yl | 4-F-Ph | (pyridin-3-yl)$CH_2$ | |
| 1-117 | $CO_2Me$ | 6-CN-pyridin-3-yl | 4-F-Ph | (pyridin-4-yl)$CH_2$ | |
| 1-118 | $CO_2Me$ | 6-CN-pyridin-3-yl | 4-F-Ph | (naphthalen-1-yl)$CH_2$ | 139-142 |
| 1-119 | $CO_2Me$ | 6-CN-pyridin-3-yl | 4-F-Ph | 2-I-Bn | 232-235 |
| 1-120 | $CO_2Me$ | 6-CN-pyridin-3-yl | 4-F-Ph | 4-$SCF_3$-Bn | 107-110 |
| 1-121 | $CO_2Me$ | 6-CN-pyridin-3-yl | 4-F-Ph | (quinolin-2-yl)$CH_2$ | 203-206 |
| 1-122 | $CO_2Me$ | 6-CN-pyridin-3-yl | 4-F-Ph | 4-CN-Bn | 188-191 |
| 1-123 | $CO_2Me$ | 6-CN-pyridin-3-yl | 4-F-Ph | 3-CN-Bn | 161-163 |
| 1-124 | $CO_2Me$ | 6-CN-pyridin-3-yl | 4-F-Ph | 2-CN-Bn | 220-223 |
| 1-125 | $CO_2Me$ | 6-CN-pyridin-3-yl | 4-F-Ph | 4-SMe-Bn | 91-93 |
| 1-126 | $CO_2Me$ | 6-CN-pyridin-3-yl | 4-F-Ph | 4-SOMe-Bn | |
| 1-127 | $CO_2Me$ | 6-CN-pyridin-3-yl | 4-F-Ph | 4-$SO_2$Me-Bn | 204-207 |
| 1-128 | $CO_2Me$ | 6-CN-pyridin-3-yl | 4-F-Ph | 4-$NPh_2$-Bn | 152-157 |
| 1-129 | $CO_2Me$ | 6-CN-pyridin-3-yl | 4-F-Ph | 4-$OCHF_2$-Bn | 95-99 |
| 1-130 | $CO_2Me$ | 6-CN-pyridin-3-yl | 4-F-Ph | 4-c-Pr-Bn | 124-128 |
| 1-131 | $CO_2Me$ | 6-CN-pyridin-3-yl | 4-F-Ph | 2,4,6-$Me_3$-Bn | 124-128 |
| 1-132 | $CO_2Me$ | 6-CN-pyridin-3-yl | 4-F-Ph | 2,4-$Cl_2$-Bn | |
| 1-133 | $CO_2Me$ | 6-CN-pyridin-3-yl | 4-F-Ph | 2,6-$Cl_2$-Bn | 140-143 |
| 1-134 | $CO_2Me$ | 6-CN-pyridin-3-yl | 4-F-Ph | 2,5-$Me_2$-Bn | |
| 1-135 | $CO_2Me$ | 6-CN-pyridin-3-yl | 4-F-Ph | 3,4-$Me_2$-Bn | |
| 1-136 | $CO_2Me$ | 6-CN-pyridin-3-yl | 4-F-Ph | 2,4-$Me_2$-Bn | 163-165 |
| 1-137 | $CO_2Me$ | 6-CN-pyridin-3-yl | 4-F-Ph | 2,6-$F_2$-Bn | 101-104 |
| 1-138 | $CO_2Me$ | 6-CN-pyridin-3-yl | 4-F-Ph | 3,4-$F_2$-Bn | 118-121 |
| 1-139 | $CO_2Me$ | 6-CN-pyridin-3-yl | 4-F-Ph | 2,4,6-$Cl_3$-Bn | |
| 1-140 | $CO_2Me$ | 6-CN-pyridin-3-yl | 4-F-Ph | 2-F-6-Cl-Bn | 121-123 |
| 1-141 | $CO_2Me$ | 6-CN-pyridin-3-yl | 4-F-Ph | 2-Cl-4-F-Bn | 127-130 |
| 1-142 | $CO_2Me$ | 6-CN-pyridin-3-yl | 4-F-Ph | 3,4-$Cl_2$-Bn | 141-144 |
| 1-143 | $CO_2Me$ | 6-CN-pyridin-3-yl | 4-F-Ph | 2,3,4,5,6-$Me_5$-Bn | 227-230 |
| 1-144 | $CO_2Me$ | 6-CN-pyridin-3-yl | 4-F-Ph | 2-$NO_2$-4-Cl-Bn | |
| 1-145 | $CO_2Me$ | 6-CN-pyridin-3-yl | 4-F-Ph | 3,5-$F_2$-Bn | 109-111 |
| 1-146 | $CO_2Me$ | 6-CN-pyridin-3-yl | 4-F-Ph | 2-OPh-Bn | |
| 1-147 | $CO_2Me$ | 6-CN-pyridin-3-yl | 4-F-Ph | 2-F-4-Cl-Bn | |
| 1-148 | $CO_2Me$ | 6-CN-pyridin-3-yl | 4-F-Ph | 3-Cl-4-F-Bn | 105-110 |
| 1-149 | $CO_2Me$ | 6-CN-pyridin-3-yl | 4-F-Ph | 3-Me-4-$NO_2$-Bn | 129-134 |
| 1-150 | $CO_2Me$ | 6-CN-pyridin-3-yl | 4-F-Ph | 2,5-$Cl_2$-Bn | 108-110 |
| 1-151 | $CO_2Me$ | 6-CN-pyridin-3-yl | 4-F-Ph | 2-Cl-4,5-$F_2$-Bn | 208-213 |
| 1-152 | $CO_2Me$ | 6-CN-pyridin-3-yl | 4-F-Ph | 2,3,4,5,6,$F_5$-Bn | 174-177 |
| 1-153 | $CO_2Me$ | 6-CN-pyridin-3-yl | 4-F-Ph | 2-Cl-5-$CF_3$-Bn | 108-112 |
| 1-154 | $CO_2Me$ | 6-CN-pyridin-3-yl | 4-F-Ph | 2-Br-4-$CF_3$-Bn | |
| 1-155 | $CO_2Me$ | 6-CN-pyridin-3-yl | 4-F-Ph | 3,5-$(CF_3)_2$-Bn | |
| 1-156 | $CO_2Me$ | 6-CN-pyridin-3-yl | 4-F-Ph | $CH_2CHF_2$ | 153-155 |
| 1-157 | $CO_2Me$ | 6-CN-pyridin-3-yl | 4-F-Ph | (naphthalen-2-yl)$CH_2$ | 121-125 |
| 1-158 | $CO_2Me$ | 6-CN-pyridin-3-yl | 4-F-Ph | (1,3-benzodioxol-5-yl)$CH_2$ | |
| 1-159 | $CO_2Me$ | 6-CN-pyridin-3-yl | 4-F-Ph | (thien-3-yl)$CH_2$ | 91-93 |
| 1-160 | $CO_2Me$ | 6-CN-pyridin-3-yl | 4-F-Ph | (pyrazol-3-yl)$CH_2$ | |
| 1-161 | $CO_2Me$ | 6-CN-pyridin-3-yl | 4-F-Ph | (oxazol-2-yl)$CH_2$ | 99-103 |
| 1-162 | $CO_2Me$ | 6-CN-pyridin-3-yl | 4-F-Ph | (imidazol-4-yl)$CH_2$ | |
| 1-163 | $CO_2Me$ | 6-CN-pyridin-3-yl | 4-F-Ph | (1,2,4-oxadiazol-3-yl)$CH_2$ | |
| 1-164 | $CO_2Me$ | 6-CN-pyridin-3-yl | 4-F-Ph | (6-Cl-pyridin-2-yl)$CH_2$ | 169-171 |
| 1-165 | $CO_2Me$ | 6-CN-pyridin-3-yl | 4-F-Ph | (6-Cl-pyridin-3-yl)$CH_2$ | 136-139 |
| 1-166 | $CO_2Me$ | 6-CN-pyridin-3-yl | 4-F-Ph | (2-Cl-thiazol-5-yl)$CH_2$ | 106-109 |
| 1-167 | $CO_2Me$ | 6-CN-pyridin-3-yl | 4-F-Ph | (2-Cl-thiazol-4-yl)$CH_2$ | 122-126 |
| 1-168 | $CO_2Me$ | 6-CN-pyridin-3-yl | 4-F-Ph | (3-(pyridin-3-yl)-ozxadiazol-5-yl)$CH_2$ | 130-133 |

TABLE 1-continued (In Table 1, $R^3$ represents a hydrogen atom, n represents 0, and m represents 0.)

| Compound No. | $R^1$ | $R^2$ | $R^4$ | $R^5$ | Physical property value |
|---|---|---|---|---|---|
| 1-169 | $CO_2Me$ | 6-CN-pyridin-3-yl | 4-F-Ph | $CH_2COMe$ | |
| 1-170 | $CO_2Me$ | 6-CN-pyridin-3-yl | 4-F-Ph | $CH_2CO$(c-Pr) | |
| 1-171 | $CO_2Me$ | 6-CN-pyridin-3-yl | 4-F-Ph | $CH_2COPh$ | |
| 1-172 | $CO_2Me$ | 6-CN-pyridin-3-yl | 4-F-Ph | $CH_2CO_2Et$ | |
| 1-173 | $CO_2Me$ | 6-CN-pyridin-3-yl | 4-F-Ph | $CH_2CO_2$(t-Bu) | |
| 1-174 | $CO_2Me$ | 6-CN-pyridin-3-yl | 4-F-Ph | $CH_2CONH_2$ | 169-173 |
| 1-175 | $CO_2Me$ | 6-CN-pyridin-3-yl | 4-F-Ph | $CH_2COCF_3$ | |
| 1-176 | $CO_2Me$ | 6-CN-pyridin-3-yl | 4-F-Ph | $CH_2CH_2CN$ | |
| 1-177 | $CO_2Me$ | 6-CN-pyridin-3-yl | 4-F-Ph | $CH_2CH_2CH_2CN$ | |
| 1-178 | $CO_2Me$ | 6-CN-pyridin-3-yl | 4-F-Ph | $CH_2OMe$ | 157-160 |
| 1-179 | $CO_2Me$ | 6-CN-pyridin-3-yl | 4-F-Ph | $CH_2SMe$ | 187-189 |
| 1-180 | $CO_2Me$ | 6-CN-pyridin-3-yl | 4-F-Ph | $CH_2OCH_2CH_2$ TMS | 127-131 |
| 1-181 | $CO_2Me$ | 6-CN-pyridin-3-yl | 4-F-Ph | $CH_2TMS$ | |
| 1-182 | CONH(n-Pr) | 6-CN-pyridin-3-yl | 4-F-Ph | Me | 190-191 |
| 1-183 | $CH_2CF_3$ | 6-CN-pyridin-3-yl | 4-F-Ph | Me | 198-199 |
| 1-184 | $CH_2CHF_2$ | 6-CN-pyridin-3-yl | 4-F-Ph | Me | |
| 1-185 | $CO_2Me$ | 6-CN-pyridin-3-yl | 4-F-Ph | 4-$CF_3$-Ph | |
| 1-186 | H | 6-CN-pyridin-3-yl | 4-F-Ph | 4-$CF_3$-Ph | |
| 1-187 | $CO_2Me$ | 6-CN-pyridin-3-yl | 4-F-Ph | 4-Cl-Ph | |
| 1-188 | H | 6-CN-pyridin-3-yl | 4-F-Ph | 4-Cl-Ph | |
| 1-189 | $CO_2Me$ | 6-CN-pyridin-3-yl | 4-F-Ph | 4-OMe-Ph | |
| 1-190 | H | 6-CN-pyridin-3-yl | 4-F-Ph | 4-OMe-Ph | |
| 1-191 | $CO_2Me$ | 6-CN-pyridin-3-yl | 4-F-Ph | Ph | |
| 1-192 | H | 6-CN-pyridin-3-yl | 4-F-Ph | Ph | |
| 1-193 | $CO_2Me$ | 5-Cl-6-CN-pyridin-3-yl | 4-F-Ph | Et | 173-177 |
| 1-194 | $CO_2Me$ | 6-CN-pyridin-3-yl | 4-F-Ph | $CHF_2$ | |
| 1-195 | $CO_2Me$ | 6-CN-pyridin-3-yl | 6-Me-pyridin-2-yl | Me | 145-147 |
| 1-196 | $CO_2Et$ | 6-CN-pyridin-3-yl | 4-F-Ph | Me | 114-115 |
| 1-197 | Me | 6-CN-pyridin-3-yl | 4-F-Ph | Me | 237-238 |
| 1-198 | $CH_2OMe$ | 6-CN-pyridin-3-yl | 4-F-Ph | Me | 209-210 |
| 1-199 | $SO_2Me$ | 6-CN-pyridin-3-yl | 4-F-Ph | Me | |
| 1-200 | $SO_2Et$ | 6-CN-pyridin-3-yl | 4-F-Ph | Me | 185-186 |
| 1-201 | $SO_2$(4-Me-Ph) | 6-CN-pyridin-3-yl | 4-F-Ph | Me | |
| 1-202 | Bn | 6-CN-pyridin-3-yl | 4-F-Ph | Me | 198-199 |
| 1-203 | $CO_2Me$ | 5-Me-6-CN-pyridin-3-yl | 3-F-Ph | Me | 181-184 |
| 1-204 | $CO_2Me$ | 5-Me-6-CN-pyridin-3-yl | 2-F-Ph | Me | 206-209 |
| 1-205 | $CO_2Me$ | 5-Me-6-CN-pyridin-3-yl | 4-CN-Ph | Me | 137-140 |
| 1-206 | $CO_2Me$ | 5-Me-6-CN-pyridin-3-yl | 4-OMe-Ph | Me | 175-178 |
| 1-207 | $CO_2Me$ | 5-Me-6-CN-pyridin-3-yl | 6-Me-pyridin-2-yl | Me | 181-183 |
| 1-208 | $CO_2Me$ | 5-F-6-CN-pyridin-3-yl | 4-F-Ph | Me | |
| 1-209 | $CO_2Me$ | 5-F-6-CN-pyridin-3-yl | 3,4-$F_2$-Ph | Me | |
| 1-210 | $CO_2Me$ | 5-F-6-CN-pyridin-3-yl | 6-Me-pyridin-2-yl | Me | |
| 1-211 | $CO_2Et$ | 5-F-6-CN-pyridin-3-yl | 4-F-Ph | Me | 180-182 |
| 1-212 | $CO_2Et$ | 5-F-6-CN-pyridin-3-yl | 3,4-$F_2$-Ph | Me | |
| 1-213 | $CO_2Et$ | 5-Cl-6-CN-pyridin-3-yl | 4-F-Ph | Me | 191-193 |
| 1-214 | $CO_2Me$ | 5-Cl-6-CN-pyridin-3-yl | 2,4-$F_2$-Ph | Me | |
| 1-215 | $CO_2Me$ | 5-Cl-6-CN-pyridin-3-yl | 3,4-$F_2$-Ph | Me | 186-188 |
| 1-216 | $CO_2Me$ | 5-Cl-6-CN-pyridin-3-yl | 3,5-$F_2$-Ph | Me | 204-206 |
| 1-217 | $CO_2Me$ | 5-Cl-6-CN-pyridin-3-yl | 2-F-4-Cl-Ph | Me | |
| 1-218 | $CO_2Me$ | 5-Cl-6-CN-pyridin-3-yl | 6-Me-pyridin-2-yl | Me | |
| 1-219 | $CO_2Et$ | 5-Cl-6-CN-pyridin-3-yl | 2,4-$F_2$-Ph | Me | |
| 1-220 | $CO_2Et$ | 5-Cl-6-CN-pyridin-3-yl | 3,4-$F_2$-Ph | Me | |
| 1-221 | $CO_2Et$ | 5-Cl-6-CN-pyridin-3-yl | 3,5-$F_2$-Ph | Me | |
| 1-222 | $CO_2Et$ | 5-Cl-6-CN-pyridin-3-yl | 2-F-4-Cl-Ph | Me | |
| 1-223 | $CO_2nPr$ | 5-Cl-6-CN-pyridin-3-yl | 4-F-Ph | Me | 180-182 |
| 1-224 | $CO_2$-n-Pr | 5-Cl-6-CN-pyridin-3-yl | 6-Me-pyridin-2-yl | Me | 132-135 |
| 1-225 | $CO_2Me$ | 5-Br-6-CN-pyridin-3-yl | 4-F-Ph | Me | 152-154 |
| 1-226 | $CO_2Et$ | 5-Br-6-CN-pyridin-3-yl | 4-F-Ph | Me | |
| 1-227 | $CO_2Me$ | 5-Br-6-CN-pyridin-3-yl | 6-Me-pyridin-2-yl | Me | |
| 1-228 | $CO_2Me$ | 5-OMe-6-CN-pyridin-3-yl | 4-F-Ph | Me | 186-188 |
| 1-229 | $CO_2Et$ | 5-OMe-6-CN-pyridin-3-yl | 4-F-Ph | Me | |
| 1-230 | $CO_2Me$ | 5-OMe-6-CN-pyridin-3-yl | 6-Me-pyridin-2-yl | Me | |
| 1-231 | $CO_2Me$ | 5-SMe-6-CN-pyridin-3-yl | 4-F-Ph | Me | 120-122 |
| 1-232 | $CO_2Me$ | 5-SMe-6-CN-pyridin-3-yl | 3,4-$F_2$-Ph | Me | |
| 1-233 | $CO_2Me$ | 5-SMe-6-CN-pyridin-3-yl | 6-Me-pyridin-2-yl | Me | |
| 1-234 | $CO_2Et$ | 6-Cl-pyridin-3-yl | 4-F-Ph | Me | 112-113 |
| 1-235 | $CO_2Me$ | 6-Cl-pyridin-3-yl | 3,4-$F_2$-Ph | Me | NMR |
| 1-236 | $CO_2Et$ | 6-Cl-pyridin-3-yl | 4-F-Ph | Bn | |
| 1-237 | $CO_2Me$ | 6-Cl-pyridin-3-yl | 1-Me-pyrazol-4-yl | Me | |
| 1-238 | $CO_2Me$ | 6-Cl-pyridin-3-yl | 1-Me-pyrazol-3-yl | Me | |
| 1-239 | $CO_2Me$ | 6-Cl-pyridin-3-yl | 6-Me-pyridin-2-yl | Me | |
| 1-240 | $CO_2Me$ | 6-Br-pyridin-3-yl | 3-F-Ph | Me | 164-165 |
| 1-241 | $CO_2Et$ | 6-Br-pyridin-3-yl | 4-F-Ph | Me | |
| 1-242 | $CO_2Me$ | 6-Br-pyridin-3-yl | 1-Me-pyrazol-4-yl | Me | |

TABLE 1-continued (In Table 1, $R^3$ represents a hydrogen atom, n represents 0, and m represents 0.)

| Compound No. | $R^1$ | $R^2$ | $R^4$ | $R^5$ | Physical property value |
|---|---|---|---|---|---|
| 1-243 | $CO_2Me$ | 6-Br-pyridin-3-yl | 1-Me-pyrazol-3-yl | Me | |
| 1-244 | $CO_2Me$ | 6-Br-pyridin-3-yl | 6-Me-pyridin-2-yl | Me | |
| 1-245 | $CO_2Et$ | 6-Br-pyridin-3-yl | 1-Me-pyrazol-4-yl | Me | |
| 1-246 | $CO_2Et$ | 6-Br-pyridin-3-yl | 1-Me-pyrazol-3-yl | Me | |
| 1-247 | $CO_2Et$ | 6-Br-pyridin-3-yl | 6-Me-pyridin-2-yl | Me | |
| 1-248 | $CO_2Me$ | 5-CN-pyridin-2-yl | 4-F-Ph | Me | 95-97 |
| 1-249 | $CO_2Et$ | 5-CN-pyridin-2-yl | 4-F-Ph | Me | 112-114 |
| 1-250 | $CO_2Me$ | 5-CN-pyridin-2-yl | 6-Me-pyridin-2-yl | Me | |
| 1-251 | $CO_2Me$ | 5-CN-pyridin-2-yl | 4-F-Ph | Bn | 138-140 |
| 1-252 | $CO_2Et$ | 5-CN-pyridin-2-yl | 4-F-Ph | Bn | 190-192 |
| 1-253 | $CO_2Me$ | 5-CN-pyridin-2-yl | 3-F-Ph | Me | 132-134 |
| 1-254 | $CO_2Me$ | 5-Cl-pyridin-2-yl | 4-F-Ph | Me | |
| 1-255 | $CO_2Me$ | 5-Cl-pyridin-2-yl | 1-Me-pyrazol-4-yl | Me | |
| 1-256 | $CO_2Me$ | 5-Cl-pyridin-2-yl | 1-Me-pyrazol-3-yl | Me | |
| 1-257 | $CO_2Me$ | 5-Cl-pyridin-2-yl | 6-Me-pyridin-2-yl | Me | |
| 1-258 | $CO_2Me$ | 5-$CF_3$-pyridin-2-yl | 4-F-Ph | Me | |
| 1-259 | $CO_2Me$ | 5-$CF_3$-pyridin-2-yl | 1-Me-pyrazol-4-yl | Me | |
| 1-260 | $CO_2Me$ | 5-$CF_3$-pyridin-2-yl | 1-Me-pyrazol-3-yl | Me | |
| 1-261 | $CO_2Me$ | 5-$CF_3$-pyridin-2-yl | 6-Me-pyridin-2-yl | Me | |
| 1-262 | $CO_2Me$ | 4-CN-Ph | 3-F-Ph | Me | 196-199 |
| 1-263 | $CO_2Me$ | 4-CN-Ph | 3-F-Ph | 4-$CO_2Me$-Bn | 129-132 |
| 1-264 | $CO_2Me$ | 4-CN-Ph | 3-OMe-Ph | Me | 119-121 |
| 1-265 | $CO_2Me$ | 4-CN-Ph | 3-Me-4-F-Ph | Me | 171-174 |
| 1-266 | $CO_2Me$ | 4-CN-Ph | 5-Cl-pyridin-2-yl | Me | |
| 1-267 | $CO_2Me$ | 4-CN-Ph | 6-Cl-pyridin-3-yl | Me | 195-198 |
| 1-268 | $CO_2Me$ | 4-CN-Ph | 6-F-pyridin-3-yl | Me | 206-209 |
| 1-269 | $CO_2Me$ | 4-CN-Ph | 6-Me-pyridin-2-yl | Me | 203-206 |
| 1-270 | $CO_2Me$ | 4-CN-Ph | 6-CN-pyridin-3-yl | Me | |
| 1-271 | $CO_2Me$ | 4-CN-Ph | 3,4,5-$F_3$-Ph | Me | 229-232 |
| 1-272 | $CO_2Me$ | 4-CN-Ph | 2-F-Ph | Me | 187-190 |
| 1-273 | $CO_2Me$ | 4-CN-Ph | 3,5-$F_2$-Ph | Me | 194-197 |
| 1-274 | $CO_2Me$ | 4-CN-Ph | 4-Me-Ph | Me | 142-145 |
| 1-275 | $CO_2Me$ | 4-CN-Ph | 3,4,5-$F_3$-Ph | 4-$CO_2Me$-Bn | 113-116 |
| 1-276 | $CO_2Me$ | 4-CN-Ph | 2-F-Ph | 4-$CO_2Me$-Bn | 119-121 |
| 1-277 | $CO_2Me$ | 4-CN-Ph | 3,5-$F_2$-Ph | 4-$CO_2Me$-Bn | 116-119 |
| 1-278 | $CO_2Me$ | 4-CN-Ph | 4-Me-Ph | 4-$CO_2Me$-Bn | 114-117 |
| 1-279 | $CO_2Me$ | 4-CN-Ph | 6-Me-pyridin-3-yl | Me | 175-178 |
| 1-280 | $CO_2Me$ | 4-CN-Ph | 5-F-pyridin-2-yl | Me | 140-143 |
| 1-281 | $CO_2Me$ | 4-CN-Ph | 6-OMe-pyridin-3-yl | Me | 107-110 |
| 1-282 | $CO_2Me$ | 4-CN-Ph | 1-Me-pyrazol-4-yl | Me | 169-170 |
| 1-283 | $CO_2Me$ | 4-CN-Ph | 2-F-4-CN-Ph | Me | |
| 1-284 | $CO_2Et$ | 4-CN-Ph | 4-F-Ph | Me | 169-172 |
| 1-285 | $CO_2Et$ | 3-F-4-CN-Ph | 4-F-Ph | Me | 218-219 |
| 1-286 | $CO_2Et$ | 3-F-4-CN-Ph | 4-F-Ph | Bn | |
| 1-287 | $CO_2Me$ | 3-F-4-CN-Ph | 4-F-Ph | Bn | |
| 1-288 | $CO_2Me$ | 3-F-4-CN-Ph | 1-Me-pyrazol-4-yl | Me | |
| 1-289 | $CO_2Me$ | 3-F-4-CN-Ph | 1-Me-pyrazol-3-yl | Me | |
| 1-290 | $CO_2Me$ | 3-F-4-CN-Ph | 6-Me-pyridin-2-yl | Me | |
| 1-291 | $CO_2Me$ | 3-Cl-4-CN-Ph | 4-F-Ph | Me | 144-146 |
| 1-292 | $CO_2Et$ | 3-Cl-4-CN-Ph | 4-F-Ph | Me | |
| 1-293 | $CO_2Me$ | 3-Cl-4-CN-Ph | 3-F-Ph | Me | |
| 1-294 | $CO_2Et$ | 3-Cl-4-CN-Ph | 3-F-Ph | Me | 108-109 |
| 1-295 | $CO_2Me$ | 3-Cl-4-CN-Ph | 3,4-$F_2$-Ph | Me | |
| 1-296 | $CO_2Me$ | 3-Cl-4-CN-Ph | 3,4-$F_2$-Ph | Bn | |
| 1-297 | $CO_2Me$ | 3-Cl-4-CN-Ph | 6-Me-pyridin-2-yl | Me | |
| 1-298 | $CO_2Me$ | 3-Br-4-CN-Ph | 4-F-Ph | Me | 100-101 |
| 1-299 | $CO_2Me$ | 3-Br-4-CN-Ph | 1-Me-pyrazol-4-yl | Me | |
| 1-300 | $CO_2Me$ | 3-Br-4-CN-Ph | 1-Me-pyrazol-3-yl | Me | |
| 1-301 | $CO_2Me$ | 3-Br-4-CN-Ph | 6-Me-pyridin-2-yl | Me | |
| 1-302 | $CO_2Et$ | 3-OMe-4-CN-Ph | 4-F-Ph | Me | 114-117 |
| 1-303 | $CO_2Me$ | 3-OMe-4-CN-Ph | 6-Me-pyridin-2-yl | Me | 167-170 |
| 1-304 | $CO_2Me$ | 3-$CF_3$-4-CN-Ph | 4-F-Ph | Me | |
| 1-305 | $CO_2Me$ | 3-$CF_3$-4-CN-Ph | 6-Me-pyridin-2-yl | Me | |
| 1-306 | $CO_2Me$ | 3,4-$(CN)_2$-Ph | 4-F-Ph | Me | 176-178 |
| 1-307 | $CO_2Me$ | 3,4-$(CN)_2$-Ph | 6-Me-pyridin-2-yl | Me | |
| 1-308 | $CO_2Me$ | 4-$CF_3$-Ph | 4-F-Ph | Me | |
| 1-309 | $CO_2Me$ | 4-$CF_3$-Ph | 1-Me-pyrazol-4-yl | Me | |
| 1-310 | $CO_2Me$ | 4-$CF_3$-Ph | 1-Me-pyrazol-3-yl | Me | |
| 1-311 | $CO_2Me$ | 4-$CF_3$-Ph | 6-Me-pyridin-2-yl | Me | |
| 1-312 | $CO_2Me$ | 4-$OCF_3$-Ph | 4-F-Ph | Me | |
| 1-313 | $CO_2Me$ | 4-$OCF_3$-Ph | 1-Me-pyrazol-4-yl | Me | |
| 1-314 | $CO_2Me$ | 4-$OCF_3$-Ph | 1-Me-pyrazol-3-yl | Me | |
| 1-315 | $CO_2Me$ | 4-$OCF_3$-Ph | 6-Me-pyridin-2-yl | Me | |
| 1-316 | $CO_2Me$ | 4-c-Pr-Ph | 4-F-Ph | Me | |

TABLE 1-continued (In Table 1, $R^3$ represents a hydrogen atom, n represents 0, and m represents 0.)

| Compound No. | $R^1$ | $R^2$ | $R^4$ | $R^5$ | Physical property value |
|---|---|---|---|---|---|
| 1-317 | $CO_2Et$ | 6-$CF_3$-pyridin-3-yl | 4-F-Ph | Me | |
| 1-318 | $CO_2Me$ | 6-$CF_3$-pyridin-3-yl | 1-Me-pyrazol-4-yl | Me | |
| 1-319 | $CO_2Me$ | 6-$CF_3$-pyridin-3-yl | 1-Me-pyrazol-3-yl | Me | |
| 1-320 | $CO_2Me$ | 6-$CF_3$-pyridin-3-yl | 6-Me-pyridin-2-yl | Me | |
| 1-321 | $CO_2Me$ | 6-Cl-pyridazin-3-yl | 4-F-Ph | Me | 125-127 |
| 1-322 | $CO_2Me$ | 5-CN-pyrimidin-2-yl | 4-F-Ph | Me | 140-143 |
| 1-323 | $CO_2Me$ | 5-(2-Et-tetrazol-5-yl)-pyridin-2-yl | 4-F-Ph | Me | |
| 1-324 | $CO_2Me$ | 6-(1-Me-tetrazol-5-yl)-pyridin-3-yl | 4-F-Ph | Me | |
| 1-325 | $CO_2Me$ | 6-($SO_2NMe_2$)-pyridin-3-yl | 4-F-Ph | Me | |
| 1-326 | $CO_2Me$ | 6-ethylsulfonyl-pyridin-3-yl | 4-F-Ph | Me | |
| 1-327 | $CO_2Me$ | 5-Br-pyrazin-2-yl | 4-F-Ph | Me | |
| 1-328 | $CO_2Et$ | 5-CN-pyridin-2-yl | 3-F-Ph | Me | 204-205 |
| 1-329 | $CO_2Et$ | 5-CN-pyridin-2-yl | 3,4,5-$F_3$-Ph | Me | NMR |
| 1-330 | $CO_2Et$ | 5-CN-pyridin-2-yl | 3-F-Ph | Bn | NMR |
| 1-331 | $CO_2Me$ | 5-CN-pyridin-2-yl | 3,4-$F_2$-Ph | Me | 126-127 |
| 1-332 | $CO_2Et$ | 5-CN-pyridin-2-yl | 3,4-$F_2$-Ph | Me | 112-114 |
| 1-333 | $CO_2Me$ | 5-Cl-pyridin-2-yl | 3-F-Ph | Me | NMR |
| 1-334 | $CO_2Me$ | 5-Cl-pyridin-2-yl | 3-F-Ph | Bn | NMR |
| 1-335 | $CO_2Et$ | 6-Cl-pyridin-3-yl | 3,4-$F_2$-Ph | Me | 113-114 |
| 1-336 | $CO_2Me$ | 6-Br-pyridin-3-yl | 3,4-$F_2$-Ph | Me | 116-117 |
| 1-337 | $CO_2Et$ | 3-F-4-CN-Ph | 3,4-$F_2$-Ph | Me | 207-208 |
| 1-338 | $CO_2Et$ | 3-Me-4-CN-Ph | 4-F-Ph | Me | 121-124 |
| 1-339 | $CO_2Me$ | 3-Me-4-CN-Ph | 6-Me-pyridin-2-yl | Me | 179-182 |
| 1-340 | Et | 6-CN-pyridin-3-yl | 4-F-Ph | Me | 171-172 |
| 1-341 | $CH_2CN$ | 6-CN-pyridin-3-yl | 4-F-Ph | Me | 179-180 |
| 1-342 | $CH_2$(c-Pr) | 6-CN-pyridin-3-yl | 4-F-Ph | Me | 210-211 |
| 1-343 | (2-Cl-thiazol-5-yl)$CH_2$ | 6-CN-pyridin-3-yl | 4-F-Ph | Me | 231-232 |
| 1-344 | H | 5-SMe-6-CN-pyridin-3-yl | 4-F-Ph | Me | 129-131 |
| 1-345 | $CO_2Me$ | 5-Br-6-(aminocarbonyl)-pyridin-3-yl | 4-F-Ph | Me | 135-137 |

In Table 1, *represents potassium salt, and **represents sodium salt.

[Formula 15]

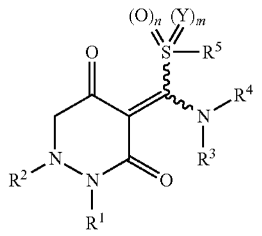

(1)

TABLE 2

(In Table 2, n represents 0, and m represents 0.)

| Compound No. | $R^1$ | $R^2$ | $R^3$ $R^5$ | $R^4$ | Physical property value |
|---|---|---|---|---|---|
| 2-1 | $CO_2Me$ | 6-$CF_3$-pyridin-3-yl | —C(=O)$CH_2CH_2$— | 4-F-Ph | |
| 2-2 | $CO_2Me$ | 6-$CF_3$-pyridin-3-yl | —C(=O)$CH_2$— | 4-F-Ph | |
| 2-3 | $CO_2Me$ | 6-$CF_3$-pyridin-3-yl | —$CH_2CH_2CH_2$— | 4-F-Ph | |
| 2-4 | $CO_2Me$ | 6-$CF_3$-pyridin-3-yl | —$CH_2CH_2$— | 4-F-Ph | |
| 2-5 | $CO_2Me$ | 6-$CF_3$-pyridin-3-yl | —$CH_2CH_2$C(=O)— | 4-F-Ph | |
| 2-6 | $CO_2Me$ | 6-$CF_3$-pyridin-3-yl | —$CH_2$C(=O)— | 4-F-Ph | |
| 2-7 | $CO_2Me$ | 6-CN-pyridin-3-yl | —C(=O)$CH_2CH_2$— | 4-F-Ph | 168-171 |
| 2-8 | $CO_2Me$ | 6-CN-pyridin-3-yl | —C(=O)$CH_2$— | 4-F-Ph | 161-166 |
| 2-9 | $CO_2Me$ | 6-CN-pyridin-3-yl | —$CH_2CH_2CH_2$— | 4-F-Ph | |
| 2-10 | $CO_2Me$ | 6-CN-pyridin-3-yl | —$CH_2CH_2$— | 4-F-Ph | |
| 2-11 | $CO_2Me$ | 6-CN-pyridin-3-yl | —$CH_2CH_2$C(=O)— | 4-F-Ph | |
| 2-12 | $CO_2Me$ | 6-CN-pyridin-3-yl | —$CH_2$C(=O)— | 4-F-Ph | |
| 2-13 | $CO_2Me$ | 4-CN-Ph | —C(=O)$CH_2CH_2$— | 4-F-Ph | |
| 2-14 | $CO_2Me$ | 4-CN-Ph | —C(=O)$CH_2$— | 4-F-Ph | |

TABLE 2-continued (In Table 2, n represents 0, and m represents 0.)

| Compound No. | $R^1$ | $R^2$ | $R^3$ | $R^5$ | $R^4$ | Physical property value |
|---|---|---|---|---|---|---|
| 2-15 | $CO_2Me$ | 5-Br-6-CN-pyridin-3-yl | —C(=O)$CH_2CH_2$— | | 4-F-Ph | |
| 2-16 | $CO_2Me$ | 5-Br-6-CN-pyridin-3-yl | —C(=O)$CH_2$— | | 4-F-Ph | |
| 2-17 | $CO_2Me$ | 5-Cl-6-CN-pyridin-3-yl | —C(=O)$CH_2CH_2$— | | 4-F-Ph | |
| 2-18 | $CO_2Me$ | 5-Cl-6-CN-pyridin-3-yl | —C(=O)$CH_2$— | | 4-F-Ph | |
| 2-19 | $CO_2Me$ | 5-F-6-CN-pyridin-3-yl | —C(=O)$CH_2CH_2$— | | 4-F-Ph | |
| 2-20 | $CO_2Me$ | 5-F-6-CN-pyridin-3-yl | —C(=O)$CH_2$— | | 4-F-Ph | |
| 2-21 | $CO_2Me$ | 6-Cl-pyridin-3-yl | —C(=O)$CH_2CH_2$— | | 4-F-Ph | |
| 2-22 | $CO_2Me$ | 6-Cl-pyridin-3-yl | —C(=O)$CH_2$— | | 4-F-Ph | |
| 2-23 | $CO_2Me$ | 6-Br-pyridin-3-yl | —C(=O)$CH_2CH_2$— | | 4-F-Ph | |
| 2-24 | $CO_2Me$ | 6-Br-pyridin-3-yl | —C(=O)$CH_2$— | | 4-F-Ph | |
| 2-25 | $CO_2Me$ | 3-Cl-4-CN-Ph | —C(=O)$CH_2CH_2$— | | 4-F-Ph | |
| 2-26 | $CO_2Me$ | 3-Cl-4-CN-Ph | —C(=O)$CH_2$— | | 4-F-Ph | |
| 2-27 | $CO_2Me$ | 3-F-4-CN-Ph | —C(=O)$CH_2CH_2$— | | 4-F-Ph | |
| 2-28 | $CO_2Me$ | 3-F-4-CN-Ph | —C(=O)$CH_2$— | | 4-F-Ph | |
| 2-29 | $CO_2Me$ | 5-CN-pyridin-2-yl | —C(=O)$CH_2CH_2$— | | 4-F-Ph | |
| 2-30 | $CO_2Me$ | 5-CN-pyridin-2-yl | —C(=O)$CH_2$— | | 4-F-Ph | |
| 2-31 | $CO_2$t-Bu | 6-$CF_3$-pyridin-3-yl | —C(=O)$CH_2CH_2$— | | 4-F-Ph | 134-137 |
| 2-32 | $CO_2$t-Bu | 6-$CF_3$-pyridin-3-yl | —C(=O)$CH_2$— | | 4-F-Ph | |
| 2-33 | H | 6-$CF_3$-pyridin-3-yl | —C(=O)$CH_2CH_2$— | | 4-F-Ph | 170-172 |
| 2-34 | H | 6-$CF_3$-pyridin-3-yl | —C(=O)$CH_2$— | | 4-F-Ph | |

In Table 2, "—" on the left side in $R^3$ and $R^5$ represents a binding position to $R^3$, and "—" on the right side therein represents a binding position to $R^5$.

[Formula 16]

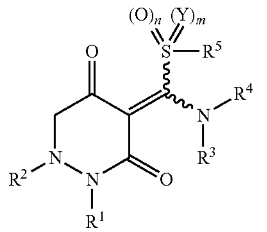

(1)

TABLE 3

(In Table 3, $R^3$ represents a hydrogen atom, n represents 0, and m represents 0.)

| Compound No. | $R^1$ | $R^2$ | $R^3$ | $R^4$ | $R^5$ | Physical property value |
|---|---|---|---|---|---|---|
| 3-1 | $CO_2Me$ | 5-CN-pyrimidin-2-yl | Me | 4-F—Ph | Me | 166-170 |
| 3-2 | $CO_2Me$ | 5-Br-6-CN-pyridin-3-yl | Me | 4-F—Ph | Me | 135-138 |
| 3-3 | $CO_2Me$ | 6-CN-pyridin-3-yl | Me | 4-F—Ph | Me | 182-185 |
| 3-4 | H | 5-SMe-6-CN-pyridin-3-yl | $CO_2Me$ | 4-F—Ph | Me | 174-176 |

[Formula 17]

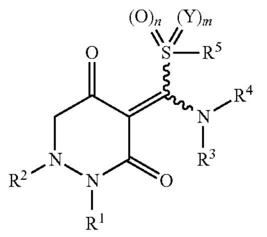

(1)

TABLE 4

| (In Table 4, $R^3$ represents a hydrogen atom.) | | | | | | | | |
|---|---|---|---|---|---|---|---|---|
| Compound No. | $R^1$ | $R^2$ | $R^4$ | $R^5$ | Y | n | m | Physical property value |
| 4-1 | $CO_2Me$ | 6-CN-pyridin-3-yl | 4-F—Ph | Me | — | 1 | 0 | |
| 4-2 | $CO_2Me$ | 6-CN-pyridin-3-yl | 4-F—Ph | Me | O | 1 | 1 | |
| 4-3 | $CO_2Me$ | 6-CN-pyridin-3-yl | 4-F—Ph | Me | NH | 0 | 1 | |
| 4-4 | $CO_2Me$ | 6-CN-pyridin-3-yl | 4-F—Ph | Me | NAc | 0 | 1 | |
| 4-5 | $CO_2Me$ | 6-CN-pyridin-3-yl | 4-F—Ph | Me | $NCO_2Et$ | 0 | 1 | |
| 4-6 | $CO_2Me$ | 6-CN-pyridin-3-yl | 4-F—Ph | Me | NCN | 0 | 1 | |
| 4-7 | $CO_2Me$ | 6-CN-pyridin-3-yl | 4-F—Ph | Me | NMe | 0 | 1 | |
| 4-8 | $CO_2Me$ | 6-CN-pyridin-3-yl | 4-F—Ph | Me | $NSO_2Ph$ | 0 | 1 | |
| 4-9 | $CO_2Me$ | 6-CN-pyridin-3-yl | 4-F—Ph | Me | $NSO_2$-4-Me—Ph | 0 | 1 | |
| 4-10 | $CO_2Me$ | 6-CN-pyridin-3-yl | 4-F—Ph | Me | NH | 1 | 1 | |
| 4-11 | $CO_2Me$ | 6-CN-pyridin-3-yl | 4-F—Ph | Me | NAc | 1 | 1 | |
| 4-12 | $CO_2Me$ | 6-CN-pyridin-3-yl | 4-F—Ph | Me | $NCO_2Et$ | 1 | 1 | |
| 4-13 | $CO_2Me$ | 6-CN-pyridin-3-yl | 4-F—Ph | Me | NCN | 1 | 1 | |
| 4-14 | $CO_2Me$ | 6-CN-pyridin-3-yl | 4-F—Ph | Me | NMe | 1 | 1 | |
| 4-15 | $CO_2Me$ | 6-CN-pyridin-3-yl | 4-F—Ph | Me | $NSO_2Ph$ | 1 | 1 | |
| 4-16 | $CO_2Me$ | 6-CN-pyridin-3-yl | 4-F—Ph | Me | $NSO_2$-4-Me—Ph | 1 | 1 | |

[Formula 18]

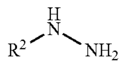

(21)

TABLE 5

| Compound No. | $R^2$ | Physical property value |
|---|---|---|
| 5-1 | 5-Cl-6-CN-pyridin-3-yl | NMR |
| 5-2 | 5-Me-6-CN-pyridin-3-yl | |
| 5-3 | 5-F-6-CN-pyridin-3-yl | |
| 5-4 | 5-Br-6-CN-pyridin-3-yl | 227-229 |
| 5-5 | 5-OMe-6-CN-pyridin-3-yl | |
| 5-6 | 5-SMe-6-CN-pyridin-3-yl | |
| 5-7 | 5-(2-Et-tetrazol-5-yl)-pyridin-2-yl | |
| 5-8 | 6-(1-Me-tetrazol-5-yl)-pyridin-3-yl | |
| 5-9 | 6-((Dimethylamino)sulfonyl)-pyridin-3-yl | |
| 5-10 | 6-ethylsulfonyl-pyridin-3-yl | |

[Formula 19]

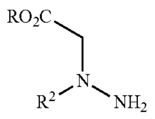

(9)

TABLE 6

| Compound No. | $R^2$ | R | Physical property value |
|---|---|---|---|
| 6-1 | 3-F-4-CN-Ph | Et | NMR |
| 6-2 | 3-Me-4-CN-Ph | Et | NMR |
| 6-3 | 3-OMe-4-CN-Ph | Et | NMR |
| 6-4 | 4-CN-Ph | Et | NMR |
| 6-5 | 5-Cl-6-CN-pyridin-3-yl | Et | NMR |
| 6-6 | 5-Me-6-CN-pyridin-3-yl | Et | NMR |
| 6-7 | 5-F-6-CN-pyridin-3-yl | Et | NMR |
| 6-8 | 5-Br-6-CN-pyridin-3-yl | Et | NMR |
| 6-9 | 5-OMe-6-CN-pyridin-3-yl | Et | 108-110 |
| 6-10 | 5-SMe-6-CN-pyridin-3-yl | Et | |
| 6-11 | 6-Br-pyridin-3-yl | Et | NMR |

TABLE 6-continued

| Compound No. | $R^2$ | R | Physical property value |
|---|---|---|---|
| 6-12 | 6-Cl-pyridin-3-yl | Et | NMR |
| 6-13 | 6-CN-pyridin-3-yl | Et | NMR |
| 6-14 | 5-CN-pyridin-2-yl | Et | NMR |
| 6-15 | 5-Cl-pyridin-2-yl | Et | NMR |
| 6-16 | 5-$CF_3$-pyridin-2-yl | Et | |
| 6-17 | 3-Cl-4-CN-Ph | Et | NMR |
| 6-18 | 3-Br-4-CN-Ph | Et | |
| 6-19 | 3-$CF_3$-4-CN-Ph | Et | NMR |
| 6-20 | 3,4-$(CN)_2$-Ph | Et | NMR |
| 6-21 | 4-$CF_3$-Ph | Et | NMR |
| 6-22 | 4-$OCF_3$-Ph | Et | NMR |
| 6-23 | 4-c-Pr-Ph | Et | |
| 6-24 | 6-Cl-pyridazin-3-yl | Et | NMR |
| 6-25 | 5-CN-pyrimidin-2-yl | Et | 86-87 |
| 6-26 | 5-(2-Et-tetrazol-5-yl)-pyridin-2-yl | Et | |
| 6-27 | 6-(1-Me-tetrazol-5-yl)-pyridin-3-yl | Et | NMR |
| 6-28 | 6-((Dimethylamino)sulfonyl)-pyridin-3-yl | Et | |
| 6-29 | 6-ethylsulfonyl-pyridin-3-yl | Et | NMR |
| 6-30 | 5-Br-pyrazin-2-yl | Et | |

TABLE 7

| Compound No. | $^1$H-NMR data |
|---|---|
| 1-53 | $^1$H-NMR($CDCl_3$/TMS, ppm) δ 11.6(s, 1H), 8.34(d, 1H), 7.57(d, 1H), 7.28(d, 1H), 4.31(dd, 2H), 2.87 – 2.84(m, 1H), 2.19(s, 3H), 1.54(s, 9H), 1.01 – 0.92(m, 2H), 0.83 – 0.75(m, 2H) |
| 1-63 | $^1$H-NMR(DMSO-$d_6$/TMS, ppm) δ 8.19(d, 1H), 7.57(d, 1H), 7.21(d, 1H), 6.79 – 6.63(brs, 4H), 4.25 – 3.85(brs, 2H), 2.11 (s, 3H), 1.41 (s, 9H) |
| 1-235 | $^1$H-NMR($CDCl_3$/TMS, ppm) δ 13.6(1H, br), 8.07 – 8.06(1H, m), 7.28 – 6.99(5H, m), 4.34(2H, br), 3.95(3H, s), 2.08(3H, s) |
| 1-329 | $^1$H-NMR($CDCl_3$/TMS, ppm) δ 13.6 (1H, br), 8.52 (1H, d), 7.82(1H, dd), 6.99 – 6.94(3H, m), 6, 60 – 6.57(1H, m), 5.47(1H, d), 4.45 – 4.36(4H, m), 2.15(3H, s), 1.37(3H, t) |
| 1-330 | $^1$H-NMR($CDCl_3$/TMS, ppm) δ 13.7(1H, br), 8.51(1H, d), 7.76(1H, dd), 7.38 – 7.32(1H, m), 7.23 – 7.13(3H, m), 7.05 – 6.88(6H, m), 5.48(1H, d), 4.46 – 4.37(2H, m), 4.16 – 4.09(2H, m), 3.95(1H, d), 3.58(1H, d), 1.37(3H, t) |
| 1-333 | $^1$H-NMR($CDCl_3$/TMS, ppm) δ 13.7(1H, br), 8.18(1H, d), 7.55(1H, dd), 7.41 – 7.35(1H, m), 7.07 – 6.99(3H, m), 6.88(1H, d), 5.30(1H, d), 4.12(2H, q), 3.96(3H, s), 2.06(3H, s) |
| 1-334 | $^1$H-NMR($CDCl_3$/TMS, ppm) δ 13.7(1H, br), 8.19(1H, d), 7.52(1H, d), 7.36 – 7.30(2H, m), 7.24 – 7.14(3H, m), 7.03 – 6.97(2H, m), 6.92(2H, d), 6.84(2H, d), 5.32(1H, d), 4.90(1H, d), 3.96(3H, s), 3.91(1H, d), 3.53(1H, d) |
| 5-1 | $^1$H-NMR($CDCl_3$/TMS, ppm) δ 8.51(1H, s), 8.05(1H, s), 7.23(1H, s), 4.55(2H, s) |
| 6-1 | $^1$H-NMR($CDCl_3$/TMS, ppm) δ 7.42 – 7.32 (m, 1H), 6.82 – 6.72 (m, 1H), 6.68 – 6.41 (1H, m), 4.27 (2H, s), 4.25 – 4.17 (2H, m) |
| 6-2 | $^1$H-NMR($CDCl_3$/TMS, ppm) δ 7.44 (1H, d), 6.81 (1H, d), 6.72 (1H, dd), 4.29 (2H, s), 4.21 (2H, q), 4.08 (2H, s), 2.48 (3H, s), 1.27 (3H, t) |
| 6-3 | $^1$H-NMR($CDCl_3$/TMS, ppm) δ 7.36 (1H, d), 6.67 (1H, d), 6.33 (1H, dd), 4.28 (2H, s), 4.22 (2H, q), 4.09 (2H, s), 3.91 (1H, s), 1.27 (3H, t) |
| 6-4 | $^1$H-NMR($CDCl_3$/TMS, ppm) δ 8.95 (br, 1H), 7.53 (2H, d), 6.84 (2H, d), 4.34 (2H, s), 4.29 – 4.21 (4H, m) |
| 6-5 | $^1$H-NMR($CDCl_3$/TMS, ppm) δ 8.21(1H, s), 7.39(1H, s), 4.30(2H, s), 4.25(2H, dd), 4.16(2H, s), 1.31(3H, t) |
| 6-6 | $^1$H-NMR($CDCl_3$/TMS, ppm) δ 8.19 (1H, d), 7.13 (1H, d), 4.30 (2H, s), 4.23 (2H, q), 4.18 – 4.00 (2H, br, s), 2.48 (3H, s), 1.29 (3H, t) |
| 6-7 | $^1$H-NMR($CDCl_3$/TMS, ppm) δ 8.14(1H, s), 7.15(1H, d), 4.31(2H, s), 4.25(2H, dd), 4.17(2H, s), 1.32(3H, t) |
| 6-8 | $^1$H-NMR($CDCl_3$/TMS, ppm) δ 8.25(1H, s), 7.56(1H, s), 4.36(2H, s), 4.25(2H, dd), 4.16(2H, s), 1.32(3H, t) |
| 6-11 | $^1$H-NMR($CDCl_3$/TMS, ppm) δ 8.02 (1H, d), 7.29 (1H, dd), 7.21 (1H, dd), 4.21 (2H, s), 4.20 (2H, q), 4.07 (2H, s), 1.26 (3H, t) |
| 6-12 | $^1$H-NMR($CDCl_3$/TMS, ppm) δ 8.02 (1H, d), 7.30 (1H, dd), 7.15 (1H, d), 4.21 (2H, s), 4.20 (2H, q), 4.07 (2H, s) |
| 6-13 | $^1$H-NMR($CDCl_3$/TMS, ppm) δ 8.39 (1H, dd), 7.51 (1H, dd), 7.27 (1H, d), 4.31 (2H, s), 4.23 (2H, q), 4.16 (2H, s), 1.29 (3H, t) |
| 6-14 | $^1$H-NMR($CDCl_3$/TMS, ppm) δ 8.35 (1H, dd), 7.67 (1H, dd), 7.30 (1H, d), 4.61 (2H, s), 4.22 (2H, q), 4.15 (2H, s), 1.29 (3H, t) |
| 6-15 | $^1$H-NMR($CDCl_3$/TMS, ppm) δ 8.03 (1H, d), 7.46 (1H, dd), 7.14 (1H, d), 4.50 (2H, s), 4.19 (2H, q), 4.10 (2H, s), 1.26 (3H, t) |
| 6-17 | $^1$H-NMR($CDCl_3$/TMS, ppm) δ 7.46 (1H, d), 7.08 (1H, d), 6.78 (1H ,dd), 4.28 (2H, s), 4.23 (2H, q), 4.10 (2H, s), 1.28 (3H, t) |

TABLE 7-continued

| Compound No. | $^1$H-NMR data |
|---|---|
| 6-19 | $^1$H-NMR($CDCl_3$/TMS, ppm) δ 7.62 (1H, d), 7.39 (1H, d), 7.00 (1H, dd), 4.33 (2H, s), 4.23 (2H, q), 4.14 (2H, s), 1.29 (3H, t) |
| 6-20 | $^1$H-NMR($CDCl_3$/TMS, ppm) δ 7.57 (1H, d), 7.38 (1H, d), 7.11 (1H, dd), 4.31 (2H, s), 4.28 (2H, q), 4.14 (2H, s), 1.30 (3H, t) |
| 6-21 | $^1$H-NMR($CDCl_3$/TMS, ppm) δ 7.47 (2H, d), 6.94 (2H, d), 4.29 (2H, s), 4.19 (2H, q), 4.09 (2H, br) |
| 6-22 | $^1$H-NMR($CDCl_3$/TMS, ppm) δ 7.10 (2H, d), 6.92 - 6.86 (2H, m), 4.33 - 4.01 (2H, br, s), 4.24 (2H, s), 4.19 (2H, q), 1.25 (2H, t) |
| 6-24 | $^1$H-NMR($CDCl_3$/TMS, ppm) δ 7.64 (1H, d), 7.25 (1H, d), 4.66 (2H, s), 4.21 (2H, q), 4.17 (2H, s), 1.28 (3H, t) |
| 6-27 | $^1$H-NMR($CDCl_3$/TMS, ppm) δ 8.49(1H, d), 8.18(1H, d), 7.38(1H, dd), 4.45(3H, s), 4.39(2H, s), 4.24(2H, q), 4.17(2H, brs), 1.29(3H, t) |
| 6-29 | $^1$H-NMR($CDCl_3$/TMS, ppm) δ 8.40 (1H, d), 7.87 (1H, d), 7.32 (1H, dd), 4.33 (2H, s), 4.23 (2H, q), 4.19 (2H, s), 3.30 (2H, q), 1.31 - 1.24 (6H, m) |

The agricultural and horticultural insecticidal agent comprising the compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, other pests such as nematodes, etc.

In addition, the agricultural and horticultural insecticidal agent comprising the compound represented by the general formula (1) of the present invention or a salt thereof as an active ingredient is excellent in properties suitable for various labor-saving application methods, penetration and translocation, environmental safety such as appropriate soil persistence, and the like.

Furthermore, the agricultural and horticultural insecticidal agent comprising the compound represented by the general formula (1) of the present invention or a salt thereof as an active ingredient has low influence on natural enemies; useful insects such as western honeybee (*Apis mellifera*), bumblebee (*Bombus* sp.), etc.; and environmental organisms such as chironomid (Chironomidae), etc.

Examples of the above pests or nematodes include the following.

Examples of the species of the order Lepidoptera include *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia cnigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis.*

Examples of the species of the order Hemiptera include *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopaloso-*

*phum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca* sp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii.*

Examples of the species of the order Coleoptera include *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis.*

Examples of the species of the order Diptera include *Culex pipiens pallens, Pegomya hyoscyami, Liriomyza huidobrensis, Musca domestica, Chlorops oryzae, Hydrellia sasakii, Agromyza oryzae, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella.*

Examples of the species of the order Hymenoptera include *Pristomyrmex pungens*, the species of the family Bethylidae, *Monomorium pharaonis, Pheidole noda, Athalia rosae, Dryocosmus kuriphilus, Formica fusca japonica*, the species of the subfamily Vespinae, *Athalia infumata infumata, Arge pagana, Athalia japonica, Acromyrmex* spp., *Solenopsis* spp., *Arge mali* and *Ochetellus glaber.*

Examples of the species of the order Orthoptera include *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma.*

Examples of the species of the order Thysanoptera include *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus,*

*Franklinella occidentalis, Thrips palmi, Frankliniella lilivora* and *Liothrips vaneeckei*.

Examples of the species of the order Acari include *Leptotrombidium akamushi, Tetranychus ludeni, Dermacentor variabilis, Tetranychus truncatus, Ornithonyssus bacoti, Demodex canis, Tetranychus viennensis, Tetranychus kanzawai, the species of the family Ixodidae such as Rhipicephalus sanguineus, Cheyletus malaccensis, Tyrophagus putrescentiae, Dermatophagoides farinae, Latrodectus hasseltii, Dermacentor taiwanensis, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.

Examples of the species of the order Isoptera include *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes quangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus*.

Examples of the species of the order Blattodea include *Periplaneta fuliginosa, Blattella germanica, Blatta orientalis, Periplaneta brunnea, Blattella lituricollis, Periplaneta japonica* and *Periplaneta americana*.

Examples of the species of the order Siphonaptera include *Pulex irritans, Ctenocephalides felis* and *Ceratophyllus gallinae*.

Examples of the species of the phylum Nematoda include *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans*.

Examples of the species of the phylum Mollusca include such as *Pomacea canaliculata, Achatina fulica, Meghimatium bilineatum, Lehmannina valentiana, Limax flavus* and *Acusta despecta sieboldiana*.

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanensis; Dermanyssus gallinae*; the species of the genus *Ornithonyssus* such as *Ornithonyssus sylviarum* and *Ornithonyssus* bursa; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium*.

The agricultural and horticultural insecticidal and acaricidal agent comprising the compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticidal agent is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticidal agent utilizes so-called penetration and translocation. That is, nursery soil, soil in transplanting holes, plant foot, irrigation water, cultivation water in hydroponics, or the like is treated with the agricultural and horticultural insecticidal and acaricidal agent to allow crops, ornamental flowering plants, etc. to absorb the compound of the present invention through the roots via soil or otherwise.

Examples of useful plants to which the agricultural and horticultural insecticidal agent of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticidal agent of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: 6-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticidal agent of the present invention can be used in combination or used systematically.

In order to control target pests, the agricultural and horticultural insecticidal agent of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticidal agent of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticidal agent of the present invention is commonly used as a formulation convenient for application, which is prepared by the usual method for preparing agrochemical formulations.

That is, the compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticidal agent or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and THF; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated aliphatic hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticidal agent of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticidal agent).

The application rate of the agricultural and horticultural insecticidal agent of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticidal agent of the present invention can be used after mixed with other agricultural and horticultural insecticidal agent, acaricides, nematicides, microbicides, biopesticides and/or the like. Further, the agricultural and horticultural insecticidal and acaricidal agent can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), fenobucarb (BPMC), Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, acynonapyr, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isocycloseram, isofenphos, isoprocarb (MIPC), epsilon-metofluthrin, epsilon-momfluorothrin, ivermectin, imicyafos, imidacloprid, imiprothrin, indazapyroxamet, indoxacarb, esfenvalerate, ethiofencarb, ethion, ethiprole, etoxazole, ethofenprox, ethoprophos, etrimfos, emamectin, emamectin-benzoate, endosulfan, empenthrin, oxazosulfyl, oxamyl, oxydemeton-methyl, oxydeprofos (ESP), oxibendazole, oxfendazole, potassium oleate, sodium oleate, cadusafos, kappa-bifenthrin, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, chloroprallethrin, kelthane (dicofol), salithion, cyhalodiamide, cyanophos (CYAP), diafenthiuron, diamidafos, cyantraniliprole, theta-cypermethrin, dienochlor, cyetpyrafen, cyenopyrafen, dioxabenzofos, diofenolan, sigma-cypermethrin, cyclaniliprole, dichlofenthion (ECP), cycloprothrin, dichlorvos (DDVP), dicloromezotiaz, disulfoton, dinotefuran, cyhalodiamide, cyhalothrin, cyphenothrin, cyfluthrin, diflubenzuron, cyflumetofen, diflovidazin, cyproflanilide, cyhexatin, cypermethrin, dimethylvinphos, dimethoate, dimpropyridaz, dimefluthrin, silafluofen, cyromazine, spidoxamat, spinetoram, spinosad, spirobudifen, spirodiclofen, spirotetramat, spiropidion, spiromesifen, sulfluramid, sulprofos, sulfoxaflor, zeta-cypermethrin, diazinon, tau-fluvalinate, dazomet, thiacloprid, thiamethoxam, tioxazafen, thiodicarb, thiocyclam, thiosultap, thiosultap-sodium, thionazin, thiometon, tiorantraniliprole, deet, dieldrin, tetrachlorantraniliprole, tyclopyrazoflor, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, doramectin, tralopyril, tralomethrin, transfluthrin, triazamate, triazuron, trichlamide, trichlorphon (DEP), trifluenfuronate, triflumezopyrium, triflumuron, tolfenpyrad, naled (BRP), nicofluprole, nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, pyflubumide, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pyriminostrobin, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fenmezoditiaz, fosthiazate, formetanate, butathiofos, buprofezin, furathiocarb, prallethrin, fluacrypyrim, fluazaindolizine, fluazinam, fluazuron, fluensulfone, fluxametamide, fluchlordiniliprole, flucycloxuron, flucythrinate, fluvalinate, flupyradifurone, flufiprole, flupyradifurone, flupyroxystrobin, flupyrazofos, flupyrimin, flufenerim, flufenoxystrobin, flufenoxuron, flufenzine, flufenprox, fluproxyfen, flubrocythrinate, fluhexafon, flubendiamide, flupentiofenox, flumethrin, flurimfen, prothiofos, protrifenbute, flonicamid, propaphos, propargite (BPPS), profenofos, broflanilide, profluthrin, propoxur (PHC), flometoquin, alpha-bromadiolone, bromopropylate, beta-cyfluthrin, hexaflumuron, hexythiazox, heptafluthrin, heptenophos, permethrin, benclothiaz, bendiocarb, benzpyrimoxan, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, momfluorothrin, lambda-cyhalothrin, ryanodine, lufenuron, rescalure, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isofetamid, isoflucypram, isoprothiolane, ipconazole, ipfentrifluconazole, ipflufenoquin, iprodione, iprovalicarb, iprobenfos, imazalil, iminoctadine, metam, iminoctadine-albesilate, iminoctadine-triacetate, imibenconazole, inpyrfluxam, uniconazole, uniconazole-P, echlomezole, edifenphos, etaconazole, ethaboxam, ethirimol, etem, ethoxyquin, etridiazole, enestroburin, enoxastrobin, epoxiconazole, oxadixyl, oxathiapiprolin, oxycarboxin, copper-8-quinolinolate, oxytetracycline, copper-oxinate, oxpoconazole, oxpoconazole-fumarate, oxolinic acid, octhilinone, ofurace, orysastrobin, carbam (metam-sodium), kasugamycin, carbamorph, carpropamid, carbendazim, carboxin, carvone, quinazamid, quinacetol, quinoxyfen, quinofumelin, chinomethionat (quinomethionate), captafol, captan, kiralaxyl, quinconazole, quintozene, guazatine, cufraneb, cuprobam, coumoxystrobin, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chloroinconazide, chlorodinitronaphthalene, chlorothalonil, chloroneb, salicylanilide, zarilamid, cyazofamid, diethyl pyrocarbonate, diethofencarb, cyclafuramid, diclocymet, dichlozoline, diclobutrazol, cyclobutrifluram, dichlofluanid, cycloheximide, dichlobentiazox, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipymetitrone, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thifluzamide, thicyofen, thioquinox, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, triclopyricarb, tricyclazole, triticonazole, tridemorph, tributyltin oxide, triflumizole, trifloxystrobin, triforine, tolylfluanid, tolclofos-methyl, tolprocarb, natamycin, nabam, nitrostyrene, nitrothal-isopropyl, nuarimol, copper nonylphenol sulfonate, halacrinate, validamycin, valifenalate, harpin protein, picarbutrazox, bixafen, picoxystrobin, picobenzamide, pydiflumetofen, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyraziflumid, pyrazophos, pyrapropoyne, pyrametostrobin, pyriofenone, pyridinitril, pydiflumetofen, pyrisoxazole, pyridachlometyl, pyrifenox, pyribencarb, pyriminostrobin, pyrimethanil, pyroxychlor, pyroxyfur, pyroquilon, vinclozolin, ferbam, famoxadone, fenapanil, fenamidone, fenaminosulf, fenaminstrobin, fenarimol, fenitropan, fenoxanil, ferimzone, ferbam, fentin, fenpiclonil, fenpicoxamid, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluindapyr, fluoxastrobin, fluoxapiprolin, fluoxytioconazole, fluotrimazole, fluopicolide, Fluopimomide, fluopyram, fluoroimide, furcarbanil, fluxapyroxad, fluquinconazole, furconazole, furconazole-cis, fludioxonil, flusilazole, flusulfamide, flutianil, flutolanil, flutriafol, flufenoxadiazam, flufenoxystrobin, furfural, flubeneteram, furmecyclox, flumetylsulforim, flumetover, flumorph, proquinazid, prochloraz, procymidone, prothiocarb, prothioconazole, pronitridine, propamocarb, propiconazole, propineb, furophanate, probenazole, bromuconazole, florylpicoxamid, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, benzovindiflupyr, bentaluron, benthiazole, benthiavalicarb, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, mandestrobin, myclozolin, myclobutanil, mildiomycin, milneb, mecarbinzid, methasulfocarb, metazoxolon, metam, metam-sodium, metalaxyl, metalaxyl-M, metarylpicoxamid, metiram, methyl isothiocyanate, meptyldinocap, metyltetraprole, metconazole, metsulfovax, methfuroxam, metominostrobin, metrafenone, mepanipyrim, mefenoxam, mefentrifluconazole, meptyldinocap, mepronil, mebenil, iodomethane, rabenzazole, methyl bromide, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, icafolin, icafolin-methyl, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, iptriazopyrid, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epyrifenacil, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, chloranocryl, chloramben, cloransulam, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorphthalim, chlorflurazole, chlorflurenol, chlorprocarb, chlorpropham, chlormequat, chloreturon, chloroxynil, chloroxuron, chlorotoluron, chloropon, saflufenacil, cyanazine, cyanatryn, di-allate, diuron, diethamquat, dioxopyritrione, dicamba, cycluron, cycloate, cycloxydim, diclosulam, cyclosulfamuron, cyclopyranil, cyclopyrimorate, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, cypyrafluone, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimesulfazet, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, tiafenacil, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetflupyrolimet, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, tripyrasulfone, trifludimoxazin, triflusulfuron, triflusulfuron-methyl, trifluralin, trifloxysulfuron, tripropindan, tribenuron, tribenuron-methyl, trifop, trifopsime, trimeturon, tolpyralate, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, haloxyfop, haloxyfop-P, haloxyfop-methyl, halosafen, halosulfuron, halosulfuron-methyl, bilanafos, bixlozone, picloram, picolinafen, bicyclopyrone, bispyribac, bispyribac-sodium, pydanon, pinoxaden, bipyrazone, bifenox, piperophos, hymexazol, pyraquinate, pyraclonil, pyrasulfotole, pyrazoxyfen, pyrazosulfuron, pyrazosulfuron-ethyl, pyrazolate, bilanafos, pyraflufen, pyraflufen-ethyl, pyriclor, pyridafol, pyrithiobac, pyrithiobac-sodium, pyridate, pyriftalid, pyributicarb, pyriflubenzoxim, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, fenpyrazone, phenmedipham, phenmedipham-ethyl, butachlor, butafenacil, butamifos, buthiuron, buthidazole, butylate, buturon, butenachlor, butroxydim, butralin, butroxydim, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloraminopyr, fluchloraminopyr-tefuryl, fluchloralin, flucetosulfuron, fluthiacet, fluthiacet-methyl, flusulfinam, flupyrsulfuron, flufenacet, flufenican, flufenoximacil, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, florpyrauxifen, hexachloroacetone, hexazinone, pethoxamid, benazolin, penoxsulam, pebulate, beflubutamid, beflubutamid-M, vernolate, perfluidone, bencarbazone, benquitrione, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, lancotrione, linuron, rimisoxafen, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor*, avirulent *Erwinia carotovora* and *Bacillus subtilis*; and biopesticides used as a herbicide, such as *Xanthomonas campestris*. Such a combined use of the agricultural and horticultural insecticidal and acaricidal agent of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

EXAMPLE

Hereinafter, the representative examples are exemplified, but the present invention is not limited to these examples.

Production Example 1

Production of tert-butyl (5EZ)-5-(((4-fluorophenyl)amino)(methylthio)methylene)-4,6-dioxo-2-[6-(trifluoromethyl)pyridin-3-yl]-tetrahydropyridazine-1(2H)-carboxylate (compound No. 1-63) and (4EZ)-4-(((4-fluorophenyl)amino)(methylthio)methylene)-1-[6-(trifluoromethyl)pyridin-3-yl]-tetrahydropyridazine-1(2H)-3,5-dione (Compound No. 1-1)

Production Example 1-1

Production of tert-butyl (5EZ)-5-(((4-fluorophenyl)amino)(methylthio)methylene)-4,6-dioxo-2-[6-(trifluoromethyl)pyridin-3-yl]-tetrahydropyridazine-1(2H)-carboxylate (Compound No. 1-63)

[Formula 20]

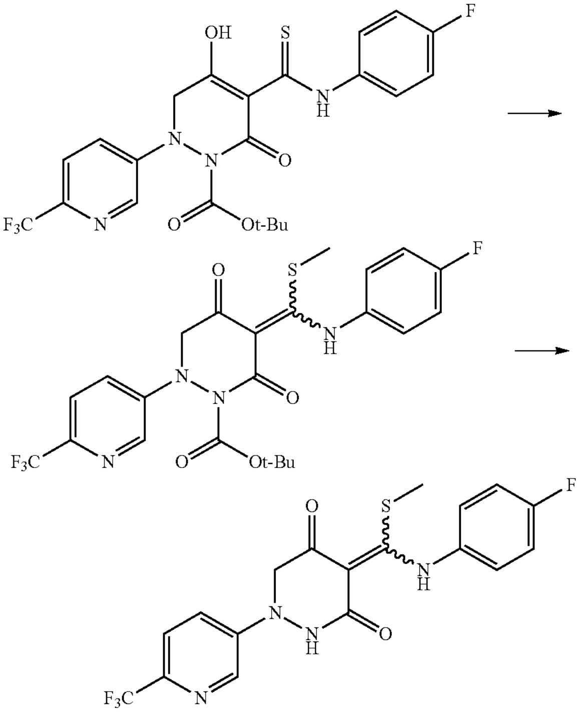

Potassium carbonate (75.0 mg, 0.547 mmol) and methyl iodide (67.0 mg, 0.469 mmol) were added in order to a solution of tert-butyl 5-((4-fluorophenyl)carbamothioyl)-4-hydroxy-6-oxo-2-(6-(trifluoromethyl)pyridin-3-yl)-2,3-dihydropyridazine-1(6H)-carboxylate (200 mg, 0.391 mmol) in acetonitrile (5 mL), and the mixture was stirred at room temperature for 1.2 hours. A saturated aqueous solution of ammonium chloride was added to the reaction solution, followed by extraction with ethyl acetate. The organic layer was washed with saturated saline, then dried over anhydrous sodium sulfate, and concentrated under reduced pressure. The residue was purified by silica gel column chromatography to obtain tert-butyl (5EZ)-5-(((4-fluorophenyl)amino)(methylthio)methylene)-4,6-dioxo-2-[6-(trifluoromethyl)pyridin-3-yl]-tetrahydropyridazine-1(2H)-carboxylate (174 mg, 0.331 mmol).

Yield: 85%

Physical property: $^1$H-NMR (DMSO-$d_6$/TMS, ppm) δ 8.19 (d, 1H), 7.57 (d, 1H), 7.21 (d, 1H), 6.79-6.63 (brs, 4H), 4.25-3.85 (brs, 2H), 2.11 (s, 3H), 1.41 (s, 9H)

Production Example 1-2

Production of (4EZ)-4-(((4-fluorophenyl)amino)(methylthio)methylene)-1-[6-(trifluoromethyl)pyridin-3-yl]-tetrahydropyridazine-1(2H)-3,5-dione (Compound No. 1-1)

tert-Butyl (5EZ)-5-(((4-fluorophenyl)amino)(methylthio)methylene)-4,6-dioxo-2-[6-(trifluoromethyl)pyridin-3-yl]-tetrahydropyridazine-1(2H)-carboxylate (34.7 mg, 0.0660 mmol) was dissolved in trifluoroacetic acid (1 mL), and the solution was stirred at room temperature for 3.3 hours. The reaction solution was concentrated under reduced pressure, and a saturated aqueous solution of ammonium chloride was then added to the residue, followed by extraction with ethyl acetate. The organic layer was washed with saturated saline, then dried over anhydrous sodium sulfate, and concentrated under reduced pressure to obtain (4EZ)-4-(((4-fluorophenyl)amino)(methylthio)methylene)-1-[6-(trifluoromethyl)pyridin-3-yl]-tetrahydropyridazine-1(2H)-3,5-dione (23.9 mg, 0.0561 mmol).

Yield: 85%

Physical property: melting point: 158-159° C.

Production Example 2

Production of (5EZ)-2-(6-cyanopyridin-3-yl)-5-(((4-fluorophenyl)amino)(methylthio)methylene)-4,6-dioxo-N-propyl-tetrahydropyridazine-1(2H)-carboxamide (Compound No. 1-182)

[Formula 21]

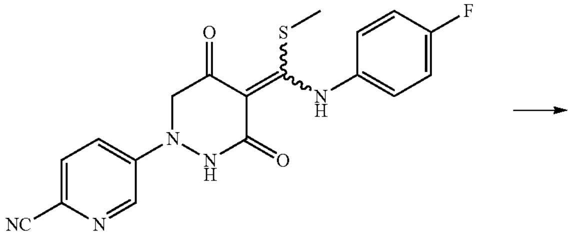

-continued

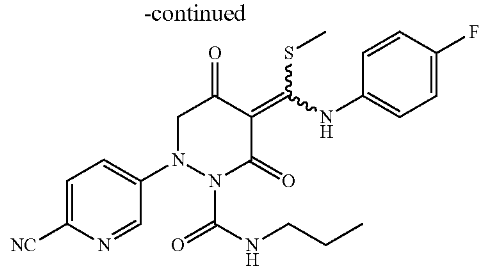

Propyl isocyanate (23 μL, 0.24 mmol) and N,N-diisopropylethylamine (44 μL, 0.26 mmol) were added to a solution of (4EZ)-5-(4-(((4-fluorophenyl)amino)(methylthio)methylene)-3,5-dioxotetrahydropyridazin-1(2H)-yl)picolinonitrile (83 mg, 0.22 mmol) in chloroform (1.5 mL), and the mixture was stirred at room temperature for 24 hours. After the completion of reaction, 1 N hydrochloric acid was added to the reaction solution, followed by extraction with ethyl acetate twice. The organic layer was washed with 1 N hydrochloric acid and saturated saline, dried over anhydrous sodium sulfate, and then concentrated under reduced pressure. The obtained residue was crystallized by the addition of a small amount of ethyl acetate and MTBE, and the crystals were then filtered by suction and washed with MTBE to obtain (5EZ)-2-(6-cyanopyridin-3-yl)-5-(((4-fluorophenyl)amino)(methylthio)methylene)-4,6-dioxo-N-propyl-tetrahydropyridazine-1(2H)-carboxamide (55 mg, 0.12 mmol).

Yield: 55%

Physical property: melting point: 190-191° C.

Production Example 3

Production of (4EZ)-5-(2-(cyclopropanecarbonyl)-4-(((4-fluorophenyl)amino)(methylthio)methylene)-3,5-dioxo-tetrahydropyridazin-1(2H)-yl)picolinonitrile (Compound No. 1-44)

[Formula 22]

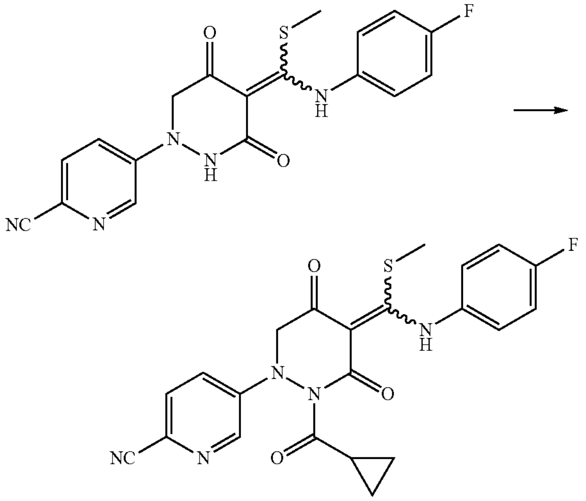

Cyclopropylcarbonyl chloride (32 μL, 0.35 mmol) and N,N-diisopropylethylamine (65 μL, 0.38 mmol) were added to a solution of (4EZ)-5-(4-(((4-fluorophenyl)amino)(methylthio)methylene)-3,5-dioxotetrahydropyridazin-1(2H)-yl) picolinonitrile (0.12 g, 0.32 mmol) in chloroform (1.6 mL), and the mixture was stirred at room temperature for 30 minutes. 4-Dimethylaminopyridine (8.2 mg, 63 μmol) was added to the reaction solution, and the mixture was stirred at room temperature for 2 hours. After the completion of reaction, 1 N hydrochloric acid was added to the reaction solution, followed by extraction with ethyl acetate twice. The organic layer was washed with 1 N hydrochloric acid and saturated saline, dried over anhydrous sodium sulfate, and then concentrated under reduced pressure. The obtained residue was purified by silica gel column chromatography to obtain (4EZ)-5-(2-(cyclopropanecarbonyl)-4-(((4-fluorophenyl)amino)(methylthio)methylene)-3,5-dioxotetrahydropyridazin-1(2H)-yl)picolinonitrile (56 mg, 0.12 mmol).

Yield: 39%

Physical property: melting point: 207-208° C.

Production Example 4

Production of (4EZ)-5-(4-(((4-fluorophenyl)amino)(methylthio)methylene)-2-methyl-3,5-dioxo-tetrahydropyridazin-1(2H)-yl)picolinonitrile (Compound No. 1-197)

[Formula 23]

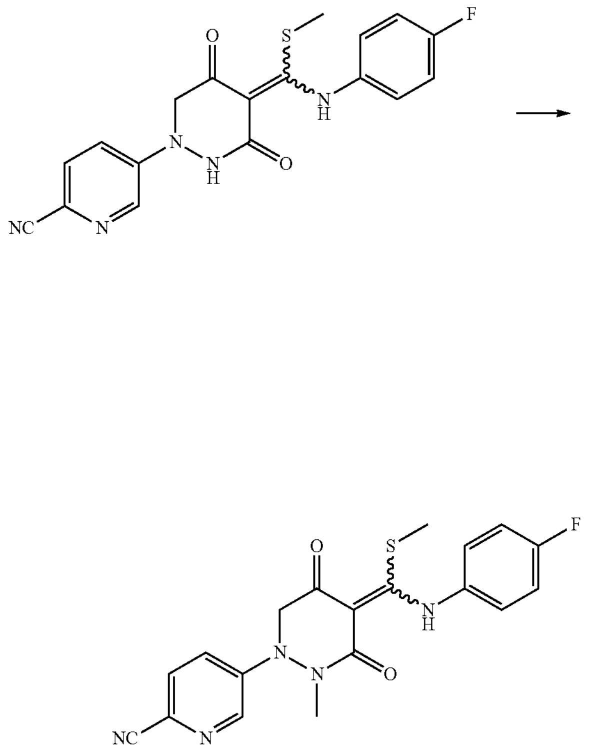

(4EZ)-5-(4-(((4-fluorophenyl)amino)(methylthio)methylene)-3,5-dioxotetrahydropyridazin-1(2H)-yl)picolinonitrile (0.20 g, 0.52 mmol) was dissolved in anhydrous N,N-dimethyl acetoamide (2.0 mL), and the solution was cooled to 0° C. Sodium hydride (53 mg, 1.2 mmol) was added to the solution, the solution was stirred under 0° C. for 10 minutes, iodomethane (36 μL, 0.57 mmol) was added to the resulting solution, followed by stirring at room temperature for 1 hour. 1 N hydrochloric acid was added to the reaction solution, followed by extraction with ethyl acetate. The organic layer was washed with 1 N hydrochloric acid and saturated saline, dried over anhydrous sodium sulfate. Solvent was evaporated under reduced pressure to precipitate solid. The solid was collected by filtration to obtain (4EZ)-5-(4-(((4-fluorophenyl)amino)(methylthio)methylene)-2-methyl-3,5-dioxo-tetrahydropyridazin-1(2H)-yl)picolinonitrile (99 mg, 0.25 mmol).

Yield: 48%

Physical property: melting point: 237-238° C.

Reference Example 1

Production of tert-butyl 5-((4-fluorophenyl)carbamothioyl)-4-hydroxy-6-oxo-2-(6-(trifluoromethyl)pyridin-3-yl)-2,3-dihydropyridazine-1(6H)-carboxylate Reference Example 1-1 Production of tert-butyl 4-hydroxy-6-oxo-2-(6-(trifluoromethyl)pyridin-3-yl)-2,3-dihydropyridazine-1(6H)-carboxylate

[Formula 24]

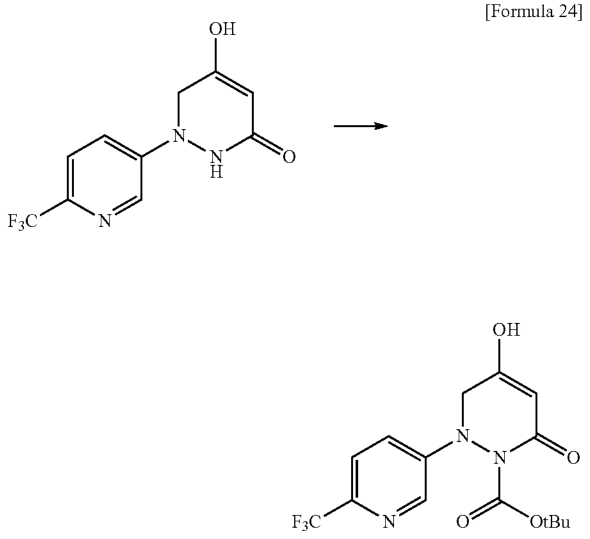

Under ice cooling, di-tertiary butyl dicarbonate (2.5 g, 11.6 mol) and N,N-dimethyl-4-aminopyridine (1.28 g, 10.6 mmol) were added to a solution of 5-hydroxy-1-(6-(trifluoromethyl)pyridin-3-yl)-1,6-dihydropyridazin-3(2H)-one (2.7 g, 10.6 mmol) in chloroform (10 mL), and the mixture was stirred at room temperature for 3 hours. An aqueous potassium bisulfate solution was added thereto, followed by extraction with ethyl acetate three times. The organic layer was dried over magnesium sulfate and then concentrated under reduced pressure. The obtained residue was purified by column chromatography to obtain tert-butyl 4-hydroxy-6-oxo-2-(6-(trifluoromethyl)pyridin-3-yl)-2,3-dihydropyridazine-1(6H)-carboxylate (1.85 g, 4.56 mmol).

Yield: 43%

Physical property: $^1$H-NMR ($CDCl_3$/TMS, ppm) δ 8.35 (d, 1H), 7.85 (d, 1H), 7.21 (d, 1H), 4.64 (brs, 1H), 4.19 (brs, 1H), 3.98 (s, 3H), 3.47 (s, 2H)

Reference Example 1-2

Production of tert-butyl 5-((4-fluorophenyl)carbamothioyl)-4-hydroxy-6-oxo-2-(6-(trifluoromethyl)pyridin-3-yl)-2,3-dihydropyridazine-1(6H)-carboxylate

[Formula 25]

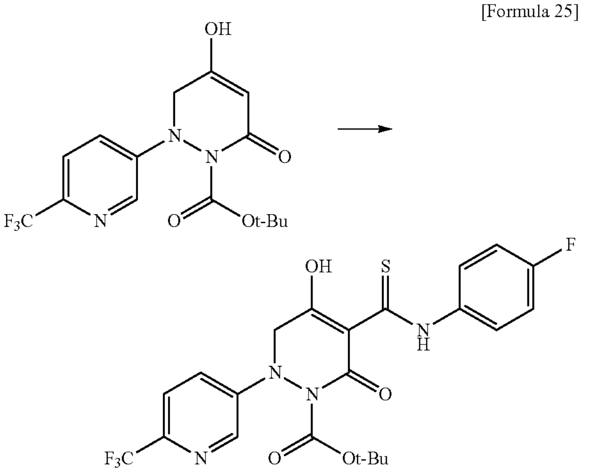

4-Fluorophenyl isothiocyanate (75 μl, 0.61 mmol) and cesium carbonate (200 mg, 0.45 mmol) were added in order to a solution of tert-butyl 4-hydroxy-6-oxo-2-(6-(trifluoromethyl)pyridin-3-yl)-2,3-dihydropyridazine-1(6H)-carboxylate (200 mg, 0.56 mmol) in dimethylacetamide (2 mL), and the mixture was stirred at room temperature for 2 hours. 1 N hydrochloric acid was added to the reaction solution, followed by extraction with ethyl acetate. The organic layer was dried over anhydrous magnesium sulfate and then concentrated under reduced pressure. The obtained residue was purified by silica gel column chromatography to obtain tert-butyl 5-((4-fluorophenyl)carbamothioyl)-4-hydroxy-6-oxo-2-(6-(trifluoromethyl)pyridin-3-yl)-2,3-dihydropyridazine-1(6H)-carboxylate (58 mg, 0.112 mmol).

Yield: 20%

Physical property: $^{1}$H-NMR ($CDCl_3$/TMS, ppm) δ 17.32 (s, 1H), 12.82 (brs, 1H), 8.41 (d, 1H), 7.62 (d, 1H), 7.40-7.35 (m, 4H), 7.15-7.09 (m, 2H), 4.65 (s, 2H), 1.55 (s, 9H)

Hereinafter, formulation examples are shown, but the present invention is not limited thereto. In the formulation examples, "part" means part by weight.

Formulation Example 1

Compound of the present invention 10 parts
Xylene 70 parts
N-methylpyrrolidone 10 parts
Mixture of polyoxyethylene nonylphenyl ether and calcium alkylbenzene sulfonate 10 parts The above ingredients are uniformly mixed for dissolution to give an emulsifiable concentrate formulation.

Formulation Example 2

Compound of the present invention 3 parts
Clay powder 82 parts
Diatomite powder 15 parts The above ingredients are uniformly mixed and then pulverized to give a dust formulation.

Formulation Example 3

Compound of the present invention 5 parts
Mixture of bentonite powder and clay powder 90 parts
Calcium lignosulfonate 5 parts The above ingredients are uniformly mixed. After addition of an appropriate volume of water, the mixture is kneaded, granulated and dried to give a granular formulation.

Formulation Example 4

Compound of the present invention 20 parts
Kaolin and synthetic high-dispersion silicic acid 75 parts
Mixture of polyoxyethylene nonylphenyl ether and calcium alkylbenzene sulfonate 5 parts The above ingredients are uniformly mixed and then pulverized to give a wettable powder formulation.

Hereinafter, biological test examples are shown, but the present invention is not limited thereto.

Test Example 1

Insecticidal Test on Diamondback moth (*Plutella xylostella*)

Adults of diamondback moth were released onto Chinese cabbage seedlings and allowed to lay eggs thereon. At 2 days after the release of the adults, the Chinese cabbage seedlings with laid eggs were dipped for about 30 seconds in agrochemical dispersions diluted to 50 ppm or 500 ppm, each of which contained a different compound represented by the general formula (1) of the present invention as an active ingredient. After air-dried, the seedlings were kept in a thermostatic chamber at 25° C. At 6 days after the dip treatment, the number of surviving larvae per plot was counted, the corrected mortality rate was calculated according to the formula shown below, and the insecticidal efficacy was evaluated according to the criteria shown below. This test was conducted in triplicate using 10 adults of diamondback moth per plot.

Corrected mortality rate (%)=(Survival rate in a non-treatment plot−Survival rate in a treatment plot)/(Survival rate in a non-treatment plot)×100 [Expression 1]

Criteria:

A: the mortality rate is 100%.
B: the mortality rate is 90 to 99%.
C: the mortality rate is 80 to 89%.
D: the mortality rate is 50 to 79%.
E: the mortality rate is 0 to 49%.

As a result, among the compounds represented by the general formula (1) of the present invention, the compounds of compound Nos. 1-1, 1-2, 1-3, 1-4, 1-5, 1-6, 1-7, 1-8, 1-14, 1-15, 1-17, 1-18, 1-29, 1-34, 1-35, 1-36, 1-38, 1-40, 1-44, 1-53, 1-54, 1-63, 1-64, 1-65, 1-66, 1-68, 1-69, 1-70, 1-71, 1-78, 1-87, 1-89, 1-93, 1-94, 1-97, 1-99, 1-100, 1-101, 1-102, 1-103, 1-104, 1-105, 1-106, 1-109, 1-110, 1-112, 1-113, 1-118, 1-120, 1-125, 1-127, 1-128, 1-130, 1-131, 1-133, 1-136, 1-137, 1-138, 1-140, 1-145, 1-148, 1-152, 1-153, 1-156, 1-161, 1-166, 1-167, 1-168, 1-174, 1-178, 1-179, 1-180, 1-193, 1-211, 1-213, 1-215, 1-216, 1-223, 1-224, 1-225, 1-234, 1-235, 1-248, 1-249, 1-251, 1-252, 1-263, 1-275, 1-277, 1-291, 1-328, 1-329, 1-330, 1-331, 1-332, 1-333, 1-334, 1-336, 1-340, 2-7, 2-8, 2-31 and 2-33 exhibited activity evaluated as A at 500 ppm against diamondback moth, and, particularly, the compounds of compound Nos. 1-1, 1-2, 1-3, 1-4, 1-5, 1-6, 1-7, 1-8, 1-15, 1-17, 1-18, 1-54, 1-63, 1-64, 1-65, 1-66, 1-68, 1-69, 1-70, 1-71, 1-87, 1-106, 1-168, 1-211, 1-215, 1-216, 1-223, 1-252, 1-332, 2-31 and 2-33 exhibited excellent activity evaluated as A at 50 ppm thereagainst.

Test Example 2

Insecticidal Test on Small Brown Planthopper (*Laodelphax striatellus*)

The compounds represented by the general formula (1) of the present invention or salts thereof were separately dispersed in water and diluted to 50 ppm or 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of small brown planthopper, and then the glass test tubes were capped with cotton plugs. At 8 days after the inoculation, the numbers of surviving larvae and dead larvae were counted, the corrected mortality rate was calculated according to the formula shown below, and the insecticidal efficacy was evaluated according to the criteria of Test Example 1.

Corrected mortality rate (%)=(Survival rate in a non-treatment plot−Survival rate in a treatment plot)/(Survival rate in a non-treatment plot)×100 [Expression 2]

As a result, among the compounds represented by the general formula (1) of the present invention, the compounds of compound Nos. 1-1, 1-2, 1-3, 1-4, 1-5, 1-6, 1-7, 1-8, 1-12, 1-14, 1-15, 1-16, 1-17, 1-18, 1-24, 1-28, 1-29, 1-30, 1-34, 1-35, 1-36, 1-38, 1-39, 1-40, 1-41, 1-42, 1-44, 1-53, 1-54, 1-63, 1-64, 1-65, 1-66, 1-67, 1-68, 1-69, 1-70, 1-71, 1-78, 1-87, 1-88, 1-89, 1-90, 1-91, 1-93, 1-94, 1-95, 1-96, 1-97, 1-99, 1-100, 1-101, 1-102, 1-103, 1-104, 1-105, 1-106, 1-109, 1-110, 1-111, 1-112, 1-113, 1-118, 1-119, 1-120, 1-121, 1-122, 1-123, 1-124, 1-125, 1-127, 1-128, 1-129, 1-130, 1-131, 1-133, 1-136, 1-137, 1-138, 1-140, 1-141, 1-142, 1-143, 1-145, 1-148, 1-149, 1-150, 1-151, 1-152, 1-153, 1-156, 1-157, 1-159, 1-161, 1-164, 1-165, 1-166, 1-167, 1-168, 1-174, 1-178, 1-179, 1-180, 1-182, 1-193, 1-196, 1-197, 1-198, 1-200, 1-202, 1-205, 1-206, 1-211, 1-213, 1-215, 1-216, 1-223, 1-224, 1-225, 1-228, 1-234, 1-235, 1-240, 1-248, 1-249, 1-251, 1-252, 1-253, 1-262, 1-263, 1-264, 1-265, 1-267, 1-268, 1-269, 1-271, 1-272, 1-273, 1-275, 1-276, 1-277, 1-278, 1-280, 1-281, 1-282, 1-284, 1-285, 1-291, 1-302, 1-303, 1-306, 1-321, 1-322, 1-328, 1-329, 1-330, 1-331, 1-332, 1-334, 1-335, 1-336, 1-337, 1-338, 1-339, 1-340, 1-341, 1-342, 1-343, 2-7, 2-8, 2-31, 2-33, 3-1 and 3-2 exhibited activity evaluated as A at 500 ppm against small brow planthopper, and, particularly, the compounds of compound Nos. 1-1, 1-2, 1-3, 1-4, 1-5, 1-6, 1-7, 1-8, 1-12, 1-14, 1-15, 1-16, 1-17, 1-18, 1-24, 1-28, 1-29, 1-30, 1-34, 1-35, 1-36, 1-38, 1-39, 1-40, 1-41, 1-42, 1-44, 1-53, 1-54, 1-63, 1-64, 1-65, 1-66, 1-67, 1-68, 1-69, 1-70, 1-71, 1-78, 1-87, 1-88, 1-89, 1-90, 1-91, 1-93, 1-94, 1-95, 1-97, 1-99, 1-100, 1-101, 1-103, 1-104, 1-105, 1-106, 1-109, 1-110, 1-111, 1-112, 1-113, 1-118, 1-119, 1-120, 1-121, 1-122, 1-123, 1-124, 1-125, 1-127, 1-128, 1-129, 1-130, 1-131, 1-133, 1-136, 1-137, 1-138, 1-140, 1-141, 1-142, 1-143, 1-145, 1-148, 1-149, 1-150, 1-151, 1-152, 1-153, 1-156, 1-157, 1-159, 1-161, 1-164, 1-165, 1-166, 1-167, 1-168, 1-174, 1-178, 1-179, 1-180, 1-182, 1-193, 1-196, 1-197, 1-198, 1-200, 1-202, 1-205, 1-206, 1-211, 1-213, 1-215, 1-216, 1-223, 1-224, 1-225, 1-228, 1-234, 1-235, 1-240, 1-248, 1-249, 1-251, 1-252, 1-253, 1-262, 1-263, 1-264, 1-265, 1-267, 1-268, 1-269, 1-271, 1-272, 1-273, 1-275, 1-276, 1-277, 1-278, 1-280, 1-281, 1-282, 1-284, 1-285, 1-291, 1-302, 1-303, 1-306, 1-321, 1-322, 1-328, 1-329, 1-330, 1-331, 1-332, 1-334, 1-335, 1-336, 1-337, 1-338, 1-339, 1-340, 1-341, 1-342, 1-343, 2-7, 2-8, 2-31, 2-33, 3-1 and 3-2 exhibited excellent activity evaluated as A at 50 ppm thereagainst.

Test Example 3

Insecticidal Test on Western Flower *thrips* (*Frankliniella occidentalis*)

Female adults of western flower *thrips* were inoculated onto kidney bean leaf pieces, and allowed to lay eggs thereon for one day, then the female adults were removed. After 3 days, the hatched larvae on the leaf pieces were counted, and then the agrochemical dispersions diluted to 50 ppm or 500 ppm, each of which contained the compound described in Tables 1 to 4 as an active ingredient were applied. The number of larvae of the species surviving at 4 days after the treatment was counted, and the corrected mortality rate was calculated according to the formula shown below, and the insecticidal efficacy was evaluated according to the criteria of Test Example 1. This test was conducted in duplicate.

Corrected mortality rate (%)=(Survival rate in a non-treatment plot−Survival rate in a treatment plot)/(Survival rate in a non-treatment plot)×100 [Expression 3]

As a result, among the compounds represented by the general formula (1) of the present invention, the compounds of compound Nos. 1-1, 1-2, 1-3, 1-4, 1-5, 1-6, 1-7, 1-8, 1-12, 1-14, 1-15, 1-18, 1-28, 1-29, 1-30, 1-34, 1-35, 1-36, 1-38, 1-39, 1-40, 1-41, 1-42, 1-44, 1-53, 1-54, 1-63, 1-64, 1-65, 1-66, 1-67, 1-68, 1-69, 1-70, 1-71, 1-78, 1-87, 1-88, 1-89, 1-90, 1-91, 1-93, 1-94, 1-96, 1-97, 1-99, 1-100, 1-101, 1-102, 1-103, 1-104, 1-105, 1-106, 1-109, 1-110, 1-111, 1-112, 1-113, 1-118, 1-119, 1-120, 1-122, 1-123, 1-124, 1-125, 1-128, 1-129, 1-130, 1-131, 1-133, 1-136, 1-137, 1-138, 1-140, 1-141, 1-142, 1-143, 1-145, 1-148, 1-149, 1-150, 1-151, 1-152, 1-153, 1-156, 1-157, 1-159, 1-161, 1-164, 1-165, 1-166, 1-167, 1-168, 1-174, 1-178, 1-179, 1-180, 1-193, 1-195, 1-196, 1-197, 1-198, 1-200, 1-207, 1-211, 1-213, 1-215, 1-216, 1-223, 1-224, 1-225, 1-228, 1-234, 1-248, 1-249, 1-251, 1-252, 1-253, 1-262, 1-263, 1-264, 1-267, 1-271, 1-272, 1-273, 1-275, 1-276, 1-277, 1-278, 1-279, 1-280, 1-281, 1-282, 1-284, 1-285, 1-291, 1-294, 1-302, 1-303, 1-306, 1-321, 1-322, 1-328, 1-329, 1-330, 1-332, 1-335, 1-336, 1-337, 1-338, 1-339, 1-340, 1-341, 1-342, 1-343, 2-7, 2-8, 2-31, 2-33, 3-1 and 3-2 exhibited activity evaluated as A at 500 ppm against western flower *thrips*, and, particularly, the compounds of compound Nos. 1-1, 1-2, 1-3, 1-4, 1-5, 1-6, 1-7, 1-8, 1-12, 1-14, 1-15, 1-18, 1-28, 1-29, 1-30, 1-34, 1-35, 1-36, 1-38, 1-39, 1-40, 1-41, 1-42, 1-44, 1-53, 1-54, 1-63, 1-64, 1-65, 1-66, 1-67, 1-68, 1-69, 1-70, 1-71, 1-78, 1-87, 1-88, 1-89, 1-90, 1-91, 1-93, 1-94, 1-97, 1-99, 1-100, 1-101, 1-102, 1-103, 1-104, 1-105, 1-109, 1-110, 1-111, 1-112, 1-113, 1-118, 1-119, 1-120, 1-122, 1-123, 1-124, 1-125, 1-128, 1-129, 1-130, 1-131, 1-133, 1-136, 1-137, 1-138, 1-140, 1-141, 1-142, 1-143, 1-145, 1-148, 1-149, 1-150, 1-151, 1-152, 1-153, 1-156, 1-157, 1-159, 1-161, 1-164, 1-165, 1-166, 1-167, 1-168, 1-174, 1-178, 1-179, 1-180, 1-193, 1-195, 1-196, 1-197, 1-198, 1-200, 1-207, 1-211, 1-213, 1-215, 1-216, 1-223, 1-224, 1-225, 1-228, 1-234, 1-248, 1-249, 1-251, 1-252, 1-253, 1-262, 1-263, 1-264, 1-267, 1-271, 1-272, 1-273, 1-275, 1-276, 1-277, 1-278, 1-279, 1-280, 1-281, 1-284, 1-285, 1-291, 1-294, 1-302, 1-303, 1-306, 1-321, 1-322, 1-328, 1-329, 1-330, 1-332, 1-335, 1-336, 1-337, 1-338, 1-339, 1-340, 1-341, 1-342, 1-343, 2-7, 2-8, 2-31, 2-33, 3-1 and 3-2 exhibited excellent activity evaluated as A at 50 ppm thereagainst.

INDUSTRIAL APPLICABILITY

The compounds or salts thereof of the present invention have an excellent effect as insecticidal agents.

The invention claimed is:

1. A compound represented by the general formula (1) or a salt thereof:

[Formula 1]

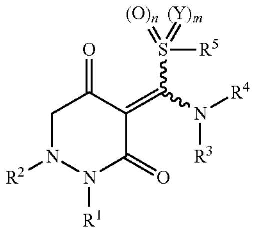

(1)

wherein $R^1$ represents (a1) a hydrogen atom;

(a2) a ($C_1$-$C_6$) alkyl group;

(a3) a ($C_2$-$C_6$) alkenyl group;

(a4) a ($C_2$-$C_6$) alkynyl group;

(a5) a ($C_3$-$C_6$) cycloalkyl group;

(a6) a halo ($C_1$-$C_6$) alkyl group;

(a7) a halo ($C_3$-$C_6$) cycloalkyl group;

(a8) a ($C_1$-$C_6$) alkoxy group;

(a9) a substituted ($C_1$-$C_6$) alkyl group having, on a chain, one to three substituents each independently selected from the group consisting of a cyano group, a ($C_1$-$C_6$) alkoxy group and a ($C_3$-$C_6$) cycloalkyl group;

(a10) a substituted ($C_3$-$C_6$) cycloalkyl group having one to three substituents each independently selected from the group consisting of a cyano group, a ($C_1$-$C_6$) alkyl group and a ($C_1$-$C_6$) alkoxy group;

(a11) a ($C_1$-$C_6$) alkylcarbonyl group;

(a12) a halo ($C_1$-$C_6$) alkylcarbonyl group;

(a13) a ($C_3$-$C_6$) cycloalkylcarbonyl group;

(a14) a ($C_1$-$C_6$) alkoxy ($C_1$-$C_6$) alkylcarbonyl group;

(a15) a ($C_1$-$C_6$) alkylsulfanyl ($C_1$-$C_6$) alkylcarbonyl group;

(a16) a phenylcarbonyl group;

(a17) a substituted phenylcarbonyl group having, on a ring, one to five substituents each independently selected from the group consisting of a halogen atom, a cyano group, a ($C_1$-$C_6$) alkyl group and a ($C_1$-$C_6$) alkoxy group;

(a18) a thienylcarbonyl group;

(a19) a substituted thienylcarbonyl group having, on a ring, one to three substituents each independently selected from the group consisting of a halogen atom, a cyano group, a ($C_1$-$C_6$) alkyl group and a ($C_1$-$C_6$) alkoxy group;

(a20) a thiazolylcarbonyl group;

(a21) a substituted thiazolylcarbonyl group having, on a ring, one or two substituents each independently selected from the group consisting of a halogen atom, a cyano group, a ($C_1$-$C_6$) alkyl group and a ($C_1$-$C_6$) alkoxy group;

(a22) a ($C_1$-$C_6$) alkoxycarbonyl group;

(a23) a halo ($C_1$-$C_6$) alkoxycarbonyl group;

(a24) a ($C_1$-$C_6$) alkoxy ($C_1$-$C_6$) alkoxycarbonyl group;

(a25) a ($C_1$-$C_6$) alkylsulfanyl ($C_1$-$C_6$) alkoxycarbonyl group;

(a26) a ($C_1$-$C_6$) alkoxy ($C_1$-$C_6$) alkoxy ($C_1$-$C_6$) alkoxycarbonyl group;

(a27) a ($C_2$-$C_6$) alkenyloxycarbonyl group;

(a28) a ($C_2$-$C_6$) alkynyloxycarbonyl group;

(a29) a ($C_3$-$C_6$) cycloalkoxycarbonyl group;

(a30) a phenyloxycarbonyl group;

(a31) a substituted phenyloxycarbonyl group having, on a ring, one to five substituents each independently selected from the group consisting of a halogen atom, a cyano group, a nitro group and a ($C_1$-$C_6$) alkyl group;

(a32) a phenyl ($C_1$-$C_6$) alkoxycarbonyl group;

(a33) a substituted phenyl ($C_1$-$C_6$) alkoxycarbonyl group having, on a ring, one to five substituents each independently selected from the group consisting of a halogen atom, a cyano group, a nitro group and a ($C_1$-$C_6$) alkyl group;

(a34) an aminocarbonyl group;

(a35) a N—($C_1$-$C_6$) alkylaminocarbonyl group;

(a36) a N,N-di-($C_1$-$C_6$) alkylaminocarbonyl group (wherein the ($C_1$-$C_6$) alkyl moieties are the same as or different from each other);

(a37) a N-halo ($C_1$-$C_6$) alkylaminocarbonyl group;

(a38) a N—($C_2$-$C_6$) alkenylaminocarbonyl group;

(a39) a N—($C_2$-$C_6$) alkynylaminocarbonyl group;

(a40) a N—($C_1$-$C_6$) alkyl-N—($C_2$-$C_6$) alkynylaminocarbonyl group;

(a41) a N—($C_3$-$C_6$) cycloalkylaminocarbonyl group;

(a42) a N—($C_1$-$C_6$) alkoxyaminocarbonyl group;

(a43) a N—($C_1$-$C_6$) alkoxy ($C_1$-$C_6$) alkylaminocarbonyl group;

(a44) a N—($C_1$-$C_6$) alkylsulfanyl ($C_1$-$C_6$) alkylaminocarbonyl group;

(a45) a N-phenyl ($C_1$-$C_6$) alkylaminocarbonyl group;

(a46) a N-substituted phenyl ($C_1$-$C_6$) alkylaminocarbonyl group having, on a ring, one to five substituents each independently selected from the group consisting of a halogen atom, a cyano group, a nitro group and a ($C_1$-$C_6$) alkyl group;

(a47) a pyrrolidinylcarbonyl group;

(a48) a N—($C_1$-$C_6$) alkylhydrazinocarbonyl group;

(a49) a N,N-di-($C_1$-$C_6$) alkylhydrazinocarbonyl group (wherein the ($C_1$-$C_6$) alkyl moieties are the same as or different from each other);

(a50) a N-phenylaminocarbonyl group;

(a51) a N-substituted phenylaminocarbonyl group having, on a ring, one to five substituents each independently selected from the group consisting of a halogen atom, a cyano group and a ($C_1$-$C_6$) alkyl group;

(a52) a ($C_1$-$C_6$) alkylsulfonyl group;

(a53) a halo ($C_1$-$C_6$) alkylsulfonyl group;

(a54) a N—($C_1$-$C_6$) alkylaminosulfonyl group;

(a55) a N-halo ($C_1$-$C_6$) alkylaminosulfonyl group;

(a56) a ($C_1$-$C_6$) alkylthiocarbonyl group;

(a57) a halo ($C_1$-$C_6$) alkylthiocarbonyl group;

(a58) a ($C_3$-$C_6$) cycloalkylthiocarbonyl group;

(a59) a ($C_1$-$C_6$) alkoxy ($C_1$-$C_6$) alkylthiocarbonyl group;

(a60) a ($C_1$-$C_6$) alkylthio ($C_1$-$C_6$) alkylthiocarbonyl group;

(a61) a ($C_1$-$C_6$) alkoxythiocarbonyl group;

(a62) a halo ($C_1$-$C_6$) alkoxythiocarbonyl group;
(a63) a pyrrolidinylthiocarbonyl group;
(a64) a phenylthiocarbonyl group;
(a65) a substituted phenylthiocarbonyl group having, on a ring, one to five substituents each independently selected from the group consisting of a halogen atom, a cyano group and a ($C_1$-$C_6$) alkyl group;
(a66) a phenyloxythiocarbonyl group;
(a67) a phenyl ($C_1$-$C_6$) alkylthiocarbonyl group;
(a68) a substituted phenyl ($C_1$-$C_6$) alkylthiocarbonyl group having, on a ring, one to five substituents each independently selected from the group consisting of a halogen atom, a cyano group and a ($C_1$-$C_6$) alkyl group;
(a69) a N—($C_1$-$C_6$) alkylaminothiocarbonyl group;
(a70) a N-halo ($C_1$-$C_6$) alkylaminothiocarbonyl group;
(a71) a N,N-di-($C_1$-$C_6$) alkylaminothiocarbonyl group (wherein the ($C_1$-$C_6$) alkyl moieties are the same as or different from each other);
(a72) a N—($C_2$-$C_6$) alkenylaminothiocarbonyl group;
(a73) a N—($C_2$-$C_6$) alkynylaminothiocarbonyl group;
(a74) a N—($C_1$-$C_6$) alkyl-N—($C_2$-$C_6$) alkynylaminothiocarbonyl group;
(a75) a N—($C_1$-$C_6$) alkylsulfanyl ($C_1$-$C_6$) alkylaminothiocarbonyl group;
(a76) a N—($C_3$-$C_6$) cycloalkylaminothiocarbonyl group;
(a77) a N—($C_1$-$C_6$) alkoxy ($C_1$-$C_6$) alkylaminothiocarbonyl group;
(a78) a N-phenylaminothiocarbonyl group;
(a79) a substituted N-phenylaminothiocarbonyl group having, on a ring, one to five substituents each independently selected from the group consisting of a halogen atom, a cyano group and a ($C_1$-$C_6$) alkyl group;
(a80) a N-phenyl ($C_1$-$C_6$) alkylaminothiocarbonyl group;
(a81) a substituted N-phenyl ($C_1$-$C_6$) alkylaminothiocarbonyl group having, on a ring, one to five substituents each independently selected from the group consisting of a halogen atom, a cyano group and a ($C_1$-$C_6$) alkyl group;
(a82) a phenyl ($C_1$-$C_6$) alkyl group;
(a83) a substituted phenyl ($C_1$-$C_6$) alkyl group having, on a ring, one to five substituents each independently selected from the group consisting of a halogen atom, a ($C_1$-$C_6$) alkyl group, a halo ($C_1$-$C_6$) alkyl group and a ($C_1$-$C_6$) alkoxy group;
(a84) a thiazolyl ($C_1$-$C_6$) alkyl group;
(a85) a substituted thiazolyl ($C_1$-$C_6$) alkyl group having, on a ring, one or two substituents each independently selected from the group consisting of a halogen atom, a ($C_1$-$C_6$) alkyl group, a halo ($C_1$-$C_6$) alkyl group and a ($C_1$-$C_6$) alkoxy group;
(a86) a phenylsulfonyl group; or
(a87) a substituted phenylsulfonyl group having, on a ring, one to five substituents each independently selected from the group consisting of a halogen atom, a ($C_1$-$C_6$) alkyl group, a halo ($C_1$-$C_6$) alkyl group and a ($C_1$-$C_6$) alkoxy group, $R^2$ represents
(b1) an aryl group;
(b2) a substituted aryl group having, on a ring, one or more substituents each independently selected from substituent group A;
(b3) a 5- to 10-membered ring heterocyclic group; or
(b4) a substituted 5- to 10-membered ring heterocyclic group having, on a ring, one or more substituents each independently selected from substituent group A, $R^3$ represents
(c1) a hydrogen atom;
(c2) a ($C_1$-$C_6$) alkyl group;
(c3) a ($C_3$-$C_6$) cycloalkyl group;
(c4) a ($C_1$-$C_6$) alkoxy group;
(c5) a ($C_1$-$C_6$) alkylcarbonyl group; or
(c6) a ($C_1$-$C_6$) alkoxycarbonyl group, $R^4$ represents
(d1) a ($C_1$-$C_6$) alkyl group;
(d2) a ($C_2$-$C_6$) alkenyl group;
(d3) a ($C_2$-$C_6$) alkynyl group;
(d4) a ($C_3$-$C_6$) cycloalkyl group;
(d5) a halo ($C_1$-$C_6$) alkyl group;
(d6) a halo ($C_2$-$C_6$) alkenyl group;
(d7) a halo ($C_2$-$C_6$) alkynyl group;
(d8) a halo ($C_3$-$C_6$) cycloalkyl group;
(d9) a substituted ($C_1$-$C_6$) alkyl group having one to three substituents each independently selected from substituent group B;
(d10) a substituted ($C_3$-$C_6$) cycloalkyl group having, on a ring, one to three substituents each independently selected from substituent group C;
(d11) a N,N-di-($C_1$-$C_6$) alkylamino group (wherein the ($C_1$-$C_6$) alkyl moieties are the same as or different from each other);
(d12) a N—($C_1$-$C_6$) alkyl-N-phenylamino group;
(d13) a ($C_1$-$C_6$) alkylsulfonyl group;
(d14) a N—($C_1$-$C_6$) alkylaminosulfonyl group;
(d15) a piperidinyl group;
(d16) a morpholinyl group;
(d17) a phenyl group;
(d18) a substituted phenyl group having, on a ring, one to five substituents each independently selected from substituent group D;
(d19) a pyridyl group;
(d20) a substituted pyridyl group having, on a ring, one to four substituents each independently selected from substituent group D;
(d21) a pyridazinyl group;
(d22) a substituted pyridazinyl group having, on a ring, one to three substituents each independently selected from substituent group D;
(d23) a pyrimidinyl group;
(d24) a substituted pyrimidinyl group having, on a ring, one to three substituents each independently selected from substituent group D;
(d25) a pyrazinyl group;
(d26) a substituted pyrazinyl group having, on a ring, one to three substituents each independently selected from substituent group D;
(d27) a triazinyl group;
(d28) a substituted triazinyl group having, on a ring, one or two substituents each independently selected from substituent group D;
(d29) a furanyl group;
(d30) a substituted furanyl group having, on a ring, one to three substituents each independently selected from substituent group D;
(d31) an oxazolyl group;
(d32) a substituted oxazolyl group having, on a ring, one or two substituents each independently selected from substituent group D;
(d33) an isoxazolyl group;
(d34) a substituted isoxazolyl group having, on a ring, one or two substituents each independently selected from substituent group D;
(d35) a thienyl group;

(d36) a substituted thienyl group having, on a ring, one to three substituents each independently selected from substituent group D;

(d37) a thiazolyl group;

(d38) a substituted thiazolyl group having, on a ring, one or two substituents each independently selected from substituent group D;

(d39) an isothiazolyl group;

(d40) a substituted isothiazolyl group having, on a ring, one or two substituents each independently selected from substituent group D;

(d41) a thiadiazolyl group;

(d42) a substituted thiadiazolyl group having, on a ring, one substituent each independently selected from substituent group D;

(d43) a pyrazolyl group;

(d44) a substituted pyrazolyl group having, on a ring, one to three substituents each independently selected from substituent group D;

(d45) a triazolyl group;

(d46) a substituted triazolyl group having, on a ring, one or two substituents each independently selected from substituent group D;

(d47) a tetrazolyl group;

(d48) a substituted tetrazolyl group having, on a ring, one substituent each independently selected from substituent group D;

(d49) a benzoxazolyl group;

(d50) a substituted benzoxazolyl group having, on a ring, one to four substituents each independently selected from substituent group D;

(d51) a benzothiazolyl group;

(d52) a substituted benzothiazolyl group having, on a ring, one to four substituents each independently selected from substituent group D;

(d53) a quinolinyl group;

(d54) a substituted quinolinyl group having, on a ring, one to six substituents each independently selected from substituent group D;

(d55) a naphthyl group;

(d56) a substituted naphthyl group having, on a ring, one to seven substituents each independently selected from substituent group D;

(d57) a tetrahydronaphthyl group;

(d58) a substituted tetrahydronaphthyl group having, on a ring, one to ten substituents each independently selected from substituent group D;

(d59) a phenyl ($C_1$-$C_6$) alkyl group;

(d60) a substituted phenyl ($C_1$-$C_6$) alkyl group having, on a ring, one to five substituents each independently selected from substituent group D;

(d61) a pyridyl ($C_1$-$C_6$) alkyl group;

(d62) a substituted pyridyl ($C_1$-$C_6$) alkyl group having, on a ring, one to four substituents each independently selected from substituent group D;

(d63) a pyrazinyl ($C_1$-$C_6$) alkyl group;

(d64) a substituted pyrazinyl ($C_1$-$C_6$) alkyl group having, on a ring, one to three substituents each independently selected from substituent group D;

(d65) a pyrimidinyl ($C_1$-$C_6$) alkyl group;

(d66) a substituted pyrimidinyl ($C_1$-$C_6$) alkyl group having, on a ring, one to three substituents each independently selected from substituent group D;

(d67) a furanyl ($C_1$-$C_6$) alkyl group;

(d68) a substituted furanyl ($C_1$-$C_6$) alkyl group having, on a ring, one to three substituents each independently selected from substituent group D;

(d69) a thienyl ($C_1$-$C_6$) alkyl group; or (d70) a substituted thienyl ($C_1$-$C_6$) alkyl group having, on a ring, one to three substituents each independently selected from substituent group D, $R^3$ and $R^4$ are optionally bonded to each other to form a ring, $R^5$ represents (e1) a ($C_1$-$C_6$) alkyl group;

(e2) a ($C_2$-$C_6$) alkenyl group;

(e3) a ($C_2$-$C_6$) alkynyl group;

(e4) a ($C_3$-$C_6$) cycloalkyl group;

(e5) a halo ($C_1$-$C_6$) alkyl group;

(e6) a halo ($C_2$-$C_6$) alkenyl group;

(e7) a halo ($C_2$-$C_6$) alkynyl group;

(e8) a halo ($C_3$-$C_6$) cycloalkyl group;

(e9) a substituted ($C_1$-$C_6$) alkyl group having, on a chain, one to three substituents each independently selected from the group consisting of a cyano group, a ($C_1$-$C_6$) alkoxy group, a ($C_3$-$C_6$) cycloalkyl group, a ($C_1$-$C_6$) alkylcarbonyl group, a ($C_3$-$C_6$) cycloalkylcarbonyl group, a phenylcarbonyl group, a ($C_1$-$C_6$) alkoxycarbonyl group, an aminocarbonyl group, a halo ($C_1$-$C_6$) alkylcarbonyl group, a ($C_1$-$C_6$) alkylsulfanyl group, a tri-($C_1$-$C_6$) alkylsilyl ($C_1$-$C_6$) alkoxy group (wherein the ($C_1$-$C_6$) alkyl groups are the same as or different from each other), and a tri-($C_1$-$C_6$) alkylsilyl group (wherein the ($C_1$-$C_6$) alkyl groups are the same as or different from each other);

(e10) a substituted ($C_3$-$C_6$) cycloalkyl group having one to three substituents each independently selected from the group consisting of a cyano group, a ($C_1$-$C_6$) alkyl group, and a ($C_1$-$C_6$) alkoxy group;

(e11) a phenyl ($C_1$-$C_6$) alkyl group;

(e12) a substituted phenyl ($C_1$-$C_6$) alkyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_3$-$C_6$) cycloalkyl group, a ($C_1$-$C_6$) alkoxycarbonyl group, a ($C_1$-$C_6$) alkylsulfanyl group, a ($C_1$-$C_6$) alkylsulfinyl group, a ($C_1$-$C_6$) alkylsulfonyl group, a halo ($C_1$-$C_6$) alkylsulfanyl group, a diphenylamino group, a phenoxy group, and a methylenedioxy group formed by two adjacent substituents together;

(e13) a pyridyl ($C_1$-$C_6$) alkyl group;

(e14) a substituted pyridyl ($C_1$-$C_6$) alkyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e15) a thiazolyl ($C_1$-$C_6$) alkyl group;

(e16) a substituted thiazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e17) an oxadiazolyl ($C_1$-$C_6$) alkyl group;

(e18) a substituted oxadiazolyl ($C_1$-$C_6$) alkyl group having a pyridyl group on a ring;

(e19) a naphthyl ($C_1$-$C_6$) alkyl group;

(e20) a substituted naphthyl ($C_1$-$C_6$) alkyl group having, on a ring, one to seven substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e21) a quinolinyl ($C_1$-$C_6$) alkyl group;

(e22) a substituted quinolinyl ($C_1$-$C_6$) alkyl group having, on a ring, one to six substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e23) a thienyl ($C_1$-$C_6$) alkyl group;

(e24) a substituted thienyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e25) a pyrazolyl ($C_1$-$C_6$) alkyl group;

(e26) a substituted pyrazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e27) an oxazolyl ($C_1$-$C_6$) alkyl group;

(e28) a substituted oxazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e29) an imidazolyl ($C_1$-$C_6$) alkyl group;

(e30) a substituted imidazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e31) a pyridyl group;

(e32) a substituted pyridyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e33) a phenyl group;

(e34) a substituted phenyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;

(e35) a ($C_1$-$C_6$) alkylcarbonyl group; or (e36) a hydrogen atom, $R^3$ and $R^5$ are optionally bonded to each other to form a 5- or 6-membered ring, when $R^5$ is (e36) a hydrogen atom, a group derived from $R^3$ by the removal of an arbitrary hydrogen atom is directly bonded to the sulfur atom bonded to $R^5$ from which the hydrogen atom is removed to form a 5- or 6-membered ring, Y represents an oxygen atom or $NR^6$ (wherein $R^6$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, a halo ($C_1$-$C_6$) alkylcarbonyl group, a ($C_1$-$C_6$) alkoxycarbonyl group, a phenylsulfonyl group, or a phenylsulfonyl group having, on a ring, one to five substituents each independently selected from the group consisting of a halogen atom, a cyano group, and a ($C_1$-$C_6$) alkyl group), m represents 0 or 1, n represents 0 or 1, substituent group A consists of (f1) a halogen atom;

(f2) a cyano group;

(f3) a nitro group;

(f4) a hydroxyl group;

(f5) a carboxyl group;

(f6) a ($C_1$-$C_6$) alkyl group;

(f7) a ($C_2$-$C_6$) alkenyl group;

(f8) a ($C_2$-$C_6$) alkynyl group;

(f9) a ($C_1$-$C_6$) alkoxy group;

(f10) a ($C_3$-$C_6$) cycloalkyl group;

(f11) a ($C_1$-$C_6$) alkylsulfanyl group;

(f12) a ($C_1$-$C_6$) alkylsulfinyl group;

(f13) a ($C_1$-$C_6$) alkylsulfonyl group;

(f14) a halo ($C_1$-$C_6$) alkyl group;

(f15) a halo ($C_2$-$C_6$) alkenyl group;

(f16) a halo ($C_2$-$C_6$) alkynyl group;

(f17) a halo ($C_1$-$C_6$) alkoxy group;

(f18) a halo ($C_3$-$C_6$) cycloalkyl group;

(f19) a halo ($C_1$-$C_6$) alkylsulfanyl group;

(f20) a halo ($C_1$-$C_6$) alkylsulfinyl group;

(f21) a halo ($C_1$-$C_6$) alkylsulfonyl group;

(f22) a N,N-di-($C_1$-$C_6$) alkylaminosulfonyl group (wherein the ($C_1$-$C_6$) alkyl moieties are the same as or different from each other);

(f23) a substituted ($C_3$-$C_6$) cycloalkyl group having, on a ring, one to three substituents each independently selected from the group consisting of a halogen atom, a cyano group, a ($C_1$-$C_6$) alkyl group, a ($C_1$-$C_6$) alkoxy group and a ($C_1$-$C_6$) alkylcarbonyl group;

(f24) a $SF_5$ group;

(f25) a ($C_1$-$C_6$) alkoxy ($C_1$-$C_6$) alkyl group;

(f26) a ($C_1$-$C_6$) alkoxy ($C_1$-$C_6$) alkoxy group;

(f27) a ($C_1$-$C_6$) alkylcarbonylamino group;

(f28) a halo ($C_1$-$C_6$) alkylcarbonylamino group;

(f29) a ($C_1$-$C_6$) alkylsulfonylamino group;

(f30) a halo ($C_1$-$C_6$) alkylsulfonylamino group;

(f31) a ($C_1$-$C_6$) alkoxycarbonyl group;

(f32) a methylenedioxy group formed by two adjacent substituents together and optionally substituted by one or two substituents each selected from the group consisting of a halogen atom, a phenyl group and a ($C_1$-$C_6$) alkyl group;

(f33) a ($C_1$-$C_6$) alkylaminocarbonyl group;

(f34) a N-halo ($C_1$-$C_6$) alkylaminocarbonyl group;

(f35) a furanyl group;

(f36) a substituted furanyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f37) an oxazolyl group;

(f38) a substituted oxazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f39) an isoxazolyl group;
(f40) a substituted isoxazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f41) an oxadiazolyl group;
(f42) a substituted oxadiazolyl group having, on a ring, one substituent each independently selected from the group consisting of a halogen atom, a cyano group, a ($C_1$-$C_6$) alkyl group, a ($C_1$-$C_6$) alkoxy group, a ($C_3$-$C_6$) cycloalkyl group, a halo ($C_1$-$C_6$) alkyl group and a halo ($C_1$-$C_6$) alkoxy group;
(f43) a thienyl group;
(f44) a substituted thienyl group having, on a ring, one to three substituents each independently selected from the group consisting of a halogen atom, a cyano group, a ($C_1$-$C_6$) alkyl group, a ($C_1$-$C_6$) alkoxy group, a ($C_3$-$C_6$) cycloalkyl group, a halo ($C_1$-$C_6$) alkyl group and a halo ($C_1$-$C_6$) alkoxy group;
(f45) a thiazolyl group;
(f46) a substituted thiazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f47) an isothiazolyl group;
(f48) a substituted isothiazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f49) a thiadiazolyl group;
(f50) a substituted thiadiazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f51) a pyrrolyl group;
(f52) a substituted pyrrolyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f53) a pyrazolyl group;
(f54) a substituted pyrazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f55) an imidazolyl group;
(f56) a substituted imidazolyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f57) a triazolyl group;
(f58) a substituted triazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f59) a tetrazolyl group;
(f60) a substituted tetrazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f61) an oxazolinyl group;
(f62) a substituted oxazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f63) a thiazolinyl group;
(f64) a substituted thiazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f65) an isoxazolinyl group;
(f66) a substituted isoxazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f67) an isothiazolinyl group;
(f68) a substituted isothiazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f69) a pyrrolidinyl group;
(f70) a substituted pyrrolidinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f71) an imidazolinyl group;
(f72) a substituted imidazolinyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f73) a phenyl group;
(f74) a substituted phenyl group having, on a ring, one to five substituents each independently selected from the group consisting of a halogen atom, a cyano group, a ($C_1$-$C_6$) alkyl group, a ($C_1$-$C_6$) alkoxy group, a ($C_3$-$C_6$) cycloalkyl group, a halo ($C_1$-$C_6$) alkyl group and a halo ($C_1$-$C_6$) alkoxy group;
(f75) a pyridyl group;
(f76) a substituted pyridyl group having, on a ring, one to four substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;
(f77) a pyridazinyl group;
(f78) a substituted pyridazinyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f79) a pyrimidinyl group;

(f80) a substituted pyrimidinyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f81) a pyrazinyl group;

(f82) a substituted pyrazinyl group having, on a ring, one to three substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f83) a triazinyl group;

(f84) a substituted triazinyl group having, on a ring, one or two substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f85) a dihydrofuranyl group;

(f86) a dihydropyranyl group;

(f87) a phenyloxy group;

(f88) a substituted phenyloxy group having, on a ring, one to five substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f89) a phenyl ($C_1$-$C_6$) alkoxy group;

(f90) a substituted phenyl ($C_1$-$C_6$) alkoxy group having, on a ring, one to five substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f91) a phenyl ($C_1$-$C_6$) alkylsulfanyl group;

(f92) a substituted phenyl ($C_1$-$C_6$) alkylsulfanyl group having, on a ring, one to five substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group;

(f93) a $R^6$—($R^7$—N═)O—S group (wherein $R^6$ represents a ($C_1$-$C_6$) alkyl group, a ($C_3$-$C_6$) cycloalkyl group, a halo ($C_1$-$C_6$) alkyl group, or ($C_1$-$C_6$) alkoxy ($C_1$-$C_6$) alkyl group, and $R^7$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, or a halo ($C_1$-$C_6$) alkylcarbonyl group); and (f94) an aminocarbonyl group, substituent group B consists of (g1) a cyano group;

(g2) a ($C_3$-$C_6$) cycloalkyl group;

(g3) a ($C_1$-$C_6$) alkoxy group;

(g4) a ($C_1$-$C_6$) alkylsulfanyl group;

(g5) a ($C_1$-$C_6$) alkylsulfinyl group;

(g6) a ($C_1$-$C_6$) alkylsulfonyl group;

(g7) a halo ($C_3$-$C_6$) cycloalkyl group;

(g8) a halo ($C_1$-$C_6$) alkoxy group;

(g9) a halo ($C_1$-$C_6$) alkylsulfanyl group;

(g10) a halo ($C_1$-$C_6$) alkylsulfinyl group;

(g11) a halo ($C_1$-$C_6$) alkylsulfonyl group;

(g12) a ($C_1$-$C_6$) alkoxycarbonyl group;

(g13) an aminocarbonyl group; and (g14) a phenylcarbonyl group, substituent group C consists of (h1) a cyano group;

(h2) a ($C_1$-$C_6$) alkyl group;

(h3) a ($C_2$-$C_6$) alkenyl group;

(h4) a ($C_2$-$C_6$) alkynyl group;

(h5) a ($C_3$-$C_6$) cycloalkyl group;

(h6) a ($C_1$-$C_6$) alkoxy group;

(h7) a ($C_1$-$C_6$) alkylsulfanyl group;

(h8) a ($C_1$-$C_6$) alkylsulfinyl group;

(h9) a ($C_1$-$C_6$) alkylsulfonyl group;

(h10) a halo ($C_1$-$C_6$) alkyl group;

(h11) a halo ($C_3$-$C_6$) cycloalkyl group;

(h12) a halo ($C_1$-$C_6$) alkoxy group;

(h13) a halo ($C_1$-$C_6$) alkylsulfanyl group;

(h14) a halo ($C_1$-$C_6$) alkylsulfinyl group;

(h15) a halo ($C_1$-$C_6$) alkylsulfonyl group;

(h16) an aminocarbonyl group; and (h17) a phenyl group, and substituent group D consists of (i1) a halogen atom;

(i2) a cyano group;

(i3) a nitro group;

(i4) an amino group;

(i5) a hydroxyl group;

(i6) a carboxyl group;

(i7) a ($C_1$-$C_6$) alkyl group;

(i8) a ($C_1$-$C_6$) alkoxy group;

(i9) a ($C_3$-$C_6$) cycloalkyl group;

(i10) a ($C_1$-$C_6$) alkylsulfanyl group;

(i11) a ($C_1$-$C_6$) alkylsulfinyl group;

(i12) a ($C_1$-$C_6$) alkylsulfonyl group;

(i13) a halo ($C_1$-$C_6$) alkyl group;

(i14) a halo ($C_1$-$C_6$) alkoxy group;

(i15) a halo ($C_3$-$C_6$) cycloalkyl group;

(i16) a halo ($C_1$-$C_6$) alkylsulfanyl group;

(i17) a halo ($C_1$-$C_6$) alkylsulfinyl group;

(i18) a halo ($C_1$-$C_6$) alkylsulfonyl group;

(i19) a ($C_1$-$C_6$) alkoxycarbonyl group;

(i20) a phenyl ($C_1$-$C_6$) alkoxycarbonyl group;

(i21) a ($C_1$-$C_6$) alkylaminocarbonyl group;

(i22) a N-halo ($C_1$-$C_6$) alkylaminocarbonyl group;

(i23) a phenyl group;

(i24) a substituted phenyl group having, on a ring, one to five substituents each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group; and (i25) a methylenedioxy group formed by two adjacent substituents together and optionally substituted by one or two substituents each selected from the group consisting of a halogen atom, a phenyl group and a ($C_1$-$C_6$) alkyl group, on the proviso that in $R^2$, an adjacent atom of an atom bonded to the tetrahydropyridazine ring is not substituted by a ($C_1$-$C_6$) alkylsulfonyl group, a halo ($C_1$-$C_6$) alkylsulfonyl group, N—($C_1$-$C_6$) alkylaminosulfonyl group, N,N-di-($C_1$-$C_6$) alkylaminosulfonyl group, and $R^6$—($R^7$—N═)O═S group (wherein $R^6$ represents a ($C_1$-$C_6$) alkyl group, a ($C_3$-$C_6$) cycloalkyl group, a halo ($C_1$-$C_6$) alkyl group, or a ($C_1$-$C_6$) alkoxy ($C_1$-$C_6$) alkyl group, and $R^7$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, or a halo ($C_1$-$C_6$) alkylcarbonyl group).

2. The compound according to claim 1 or a salt thereof, wherein $R^1$, $R^3$, $R^4$, $R^5$, Y, m, n, substituent groups A, B, C and D are as defined above, and $R^2$ is (b5) a phenyl group;

(b6) a substituted phenyl group having, on a ring, one to five substituents each independently selected from substituent group A;

(b7) a pyridyl group;

(b8) a substituted pyridyl group having, on a ring, one to four substituents each independently selected from substituent group A;

(b9) a pyridazinyl group;

(b10) a substituted pyridazinyl group having, on a ring, one to three substituents each independently selected from substituent group A;

(b11) a pyrimidinyl group;

(b12) a substituted pyrimidinyl group having, on a ring, one to three substituents each independently selected from substituent group A;

(b13) a pyrazinyl group;

(b14) a substituted pyrazinyl group having, on a ring, one to three substituents each independently selected from substituent group A;

(b15) a triazinyl group;

(b16) a substituted triazinyl group having, on a ring, one or two substituents each independently selected from substituent group A;

(b17) a 2-oxopyridyl group;

(b18) a substituted 2-oxopyridyl group having, on a ring, one to four substituents each independently selected from substituent group A;

(b19) a furanyl group;

(b20) a substituted furanyl group having, on a ring, one to three substituents each independently selected from substituent group A;

(b21) an oxazolyl group;

(b22) a substituted oxazolyl group having, on a ring, one or two substituents each independently selected from substituent group A;

(b23) an isoxazolyl group;

(b24) a substituted isoxazolyl group having, on a ring, one or two substituents each independently selected from substituent group A;

(b25) an oxadiazolyl group;

(b26) a substituted oxadiazolyl group having, on a ring, one substituent each independently selected from substituent group A;

(b27) a thienyl group;

(b28) a substituted thienyl group having, on a ring, one to three substituents each independently selected from substituent group A;

(b29) a thiazolyl group;

(b30) a substituted thiazolyl group having, on a ring, one or two substituents each independently selected from substituent group A;

(b31) an isothiazolyl group;

(b32) a substituted isothiazolyl group having, on a ring, one or two substituents each independently selected from substituent group A;

(b33) a thiadiazolyl group;

(b34) a substituted thiadiazolyl group having, on a ring, one substituent each independently selected from substituent group A;

(b35) a pyrrolyl group;

(b36) a substituted pyrrolyl group having, on a ring, one to four substituents each independently selected from substituent group A;

(b37) a pyrazolyl group;

(b38) a substituted pyrazolyl group having, on a ring, one to three substituents each independently selected from substituent group A;

(b39) an imidazolyl group;

(b40) a substituted imidazolyl group having, on a ring, one to three substituents each independently selected from substituent group A;

(b41) a triazolyl group;

(b42) a substituted triazolyl group having, on a ring, one or two substituents each independently selected from substituent group A;

(b43) a tetrazolyl group;

(b44) a substituted tetrazolyl group having, on a ring, one substituent each independently selected from substituent group A;

(b45) a benzofuranyl group;

(b46) a substituted benzofuranyl group having, on a ring, one to five substituents each independently selected from substituent group A;

(b47) a benzoxazolyl group;

(b48) a substituted benzoxazolyl group having, on a ring, one to four substituents each independently selected from substituent group A;

(b49) a benzisoxazolyl group;

(b50) a substituted benzisoxazolyl group having, on a ring, one to four substituents each independently selected from substituent group A;

(b51) a benzothienyl group;

(b52) a substituted benzothienyl group having, on a ring, one to five substituents each independently selected from substituent group A;

(b53) a benzothiazolyl group;

(b54) a substituted benzothiazolyl group having, on a ring, one to four substituents each independently selected from substituent group A;

(b55) a benzisothiazolyl group;

(b56) a substituted benzisothiazolyl group having, on a ring, one to four substituents each independently selected from substituent group A;

(b57) an indolyl group;

(b58) a substituted indolyl group having, on a ring, one to six substituents each independently selected from substituent group A;

(b59) an isoindolyl group;

(b60) a substituted isoindolyl group having, on a ring, one to six substituents each independently selected from substituent group A;

(b61) an indazolyl group;

(b62) a substituted indazolyl group having, on a ring, one to five substituents each independently selected from substituent group A;

(b63) a benzimidazolyl group;

(b64) a substituted benzimidazolyl group having, on a ring, one to five substituents each independently selected from substituent group A;

(b65) a benzotriazolyl group;

(b66) a substituted benzotriazolyl group having, on a ring, one to four substituents each independently selected from substituent group A;

(b67) a furopyridyl group;

(b68) a substituted furopyridyl group having, on a ring, one to four substituents each independently selected from substituent group A;

(b69) a thienopyridyl group;
(b70) a substituted thienopyridyl group having, on a ring, one to four substituents each independently selected from substituent group A;
(b71) a thiazolopyridyl group;
(b72) a substituted thiazolopyridyl group having, on a ring, one to four substituents each independently selected from substituent group A;
(b73) an imidazopyridyl group;
(b74) a substituted imidazopyridyl group having, on a ring, one to five substituents each independently selected from substituent group A;
(b75) an indolizinyl group;
(b76) a substituted indolizinyl group having, on a ring, one to six substituents each independently selected from substituent group A;
(b77) a pyrrolopyridyl group;
(b78) a substituted pyrrolopyridyl group having, on a ring, one to five substituents each independently selected from substituent group A;
(b79) a pyrrolopyrimidinyl group;
(b80) a substituted pyrrolopyrimidinyl group having, on a ring, one to five substituents each independently selected from substituent group A;
(b81) an oxazolopyridyl group;
(b82) a substituted oxazolopyridyl group having, on a ring, one to three substituents each independently selected from substituent group A;
(b83) an isoxazolopyridyl group;
(b84) a substituted isoxazolopyridyl group having, on a ring, one to three substituents each independently selected from substituent group A;
(b85) an isothiazolopyridyl group;
(b86) a substituted isothiazolopyridyl group having, on a ring, one to three substituents each independently selected from substituent group A;
(b87) an imidazopyrimidinyl group;
(b88) a substituted imidazopyrimidinyl group having, on a ring, one to five substituents each independently selected from substituent group A;
(b89) a pyrazolopyridyl group;
(b90) a substituted pyrazolopyridyl group having, on a ring, one to five substituents each independently selected from substituent group A;
(b91) a pyrazolopyrimidinyl group;
(b92) a substituted pyrazolopyrimidinyl group having, on a ring, one to five substituents each independently selected from substituent group A;
(b93) a triazolopyridyl group;
(b94) a substituted triazolopyridyl group having, on a ring, one to four substituents each independently selected from substituent group A;
(b95) a triazolopyrimidinyl group;
(b96) a substituted triazolopyrimidinyl group having, on a ring, one to four substituents each independently selected from substituent group A;
(b97) a quinoxalinyl group;
(b98) a substituted quinoxalinyl group having, on a ring, one to five substituents each independently selected from substituent group A;
(b99) a quinolinyl group;
(b100) a substituted quinolinyl group having, on a ring, one to six substituents each independently selected from substituent group A;
(b101) a naphthyl group;
(b102) a substituted naphthyl group having, on a ring, one to seven substituents each independently selected from substituent group A;
(b103) an isoquinolinyl group;
(b104) a substituted isoquinolinyl group having, on a ring, one to six substituents each independently selected from substituent group A;
(b105) a cinnolinyl group;
(b106) a substituted cinnolinyl group having, on a ring, one to five substituents each independently selected from substituent group A;
(b107) a phthalazinyl group;
(b108) a substituted phthalazinyl group having, on a ring, one to five substituents each independently selected from substituent group A;
(b109) a quinazolinyl group;
(b110) a substituted quinazolinyl group having, on a ring, one to five substituents each independently selected from substituent group A;
(b111) a naphthyridinyl group; or
(b112) a substituted naphthyridinyl group having, on a ring, one to five substituents each independently selected from substituent group A.

3. The compound according to claim 1 or a salt thereof, wherein $R^1$ is
(a1) a hydrogen atom;
(a2) a ($C_1$-$C_6$) alkyl group;
(a6) a halo ($C_1$-$C_6$) alkyl group;
(a9) a substituted ($C_1$-$C_6$) alkyl group having, on a chain, one to three substituents each independently selected from the group consisting of a cyano group, a ($C_1$-$C_6$) alkoxy group and a ($C_3$-$C_6$) cycloalkyl group;
(a11) a ($C_1$-$C_6$) alkylcarbonyl group;
(a12) a halo ($C_1$-$C_6$) alkylcarbonyl group;
(a13) a ($C_3$-$C_6$) cycloalkylcarbonyl group;
(a22) a ($C_1$-$C_6$) alkoxycarbonyl group;
(a23) a halo ($C_1$-$C_6$) alkoxycarbonyl group;
(a24) a ($C_1$-$C_6$) alkoxy ($C_1$-$C_6$) alkoxycarbonyl group;
(a35) a N—($C_1$-$C_6$) alkylaminocarbonyl group;
(a41) a N—($C_3$-$C_6$) cycloalkylaminocarbonyl group;
(a52) a ($C_1$-$C_6$) alkylsulfonyl group;
(a69) a N—($C_1$-$C_6$) alkylaminothiocarbonyl group;
(a76) a N—($C_3$-$C_6$) cycloalkylaminothiocarbonyl group;
(a82) a phenyl ($C_1$-$C_6$) alkyl group;
(a84) a thiazolyl ($C_1$-$C_6$) alkyl group;
(a85) a substituted thiazolyl ($C_1$-$C_6$) alkyl group having, on a ring, one or two substituents each independently selected from the group consisting of a halogen atom, a ($C_1$-$C_6$) alkyl group, a halo ($C_1$-$C_6$) alkyl group and a ($C_1$-$C_6$) alkoxy group;
(a86) a phenylsulfonyl group; or
(a87) a substituted phenylsulfonyl group having, on a ring, one to five substituents each independently selected from the group consisting of a halogen atom, a ($C_1$-$C_6$) alkyl group, a halo ($C_1$-$C_6$) alkyl group and a ($C_1$-$C_6$) alkoxy group, $R^2$ is
(b5) a phenyl group;
(b6) a substituted phenyl group having, on a ring, one to five substituents each independently selected from substituent group A;
(b7) a pyridyl group;
(b8) a substituted pyridyl group having, on a ring, one to four substituents each independently selected from substituent group A;
(b9) a pyridazinyl group;

(b10) a substituted pyridazinyl group having, on a ring, one to three substituents each independently selected from substituent group A;
(b11) a pyrimidinyl group;
(b12) a substituted pyrimidinyl group having, on a ring, one to three substituents each independently selected from substituent group A;
(b13) a pyrazinyl group;
(b14) a substituted pyrazinyl group having, on a ring, one to three substituents each independently selected from substituent group A;
(b21) an oxazolyl group;
(b22) a substituted oxazolyl group having, on a ring, one or two substituents each independently selected from substituent group A;
(b25) an oxadiazolyl group;
(b26) a substituted oxadiazolyl group having, on a ring, one substituent each independently selected from substituent group A;
(b27) a thienyl group;
(b28) a substituted thienyl group having, on a ring, one to three substituents each independently selected from substituent group A;
(b29) a thiazolyl group;
(b30) a substituted thiazolyl group having, on a ring, one or two substituents each independently selected from substituent group A;
(b31) an isothiazolyl group;
(b32) a substituted isothiazolyl group having, on a ring, one or two substituents each independently selected from substituent group A;
(b33) a thiadiazolyl group;
(b34) a substituted thiadiazolyl group having, on a ring, one substituent each independently selected from substituent group A;
(b97) a quinoxalinyl group;
(b98) a substituted quinoxalinyl group having, on a ring, one to five substituents each independently selected from substituent group A;
(b99) a quinolinyl group; or
(b100) a substituted quinolinyl group having, on a ring, one to six substituents each independently selected from substituent group A;
$R^3$ is
(c1) a hydrogen atom;
(c2) a $(C_1-C_6)$ alkyl group;
(c3) a $(C_3-C_6)$ cycloalkyl group;
(c5) a $(C_1-C_6)$ alkylcarbonyl group; or
(c6) a $(C_1-C_6)$ alkoxycarbonyl group,
$R^4$ is
(d1) a $(C_1-C_6)$ alkyl group;
(d3) a $(C_2-C_6)$ alkynyl group;
(d4) a $(C_3-C_6)$ cycloalkyl group;
(d5) a halo $(C_1-C_6)$ alkyl group;
(d9) a substituted $(C_1-C_6)$ alkyl group having one to three substituents each independently selected from substituent group B;
(d10) a substituted $(C_3-C_6)$ cycloalkyl group having, on a ring, one to three substituents each independently selected from substituent group C;
(d17) a phenyl group;
(d18) a substituted phenyl group having, on a ring, one to five substituents each independently selected from substituent group D;
(d19) a pyridyl group;
(d20) a substituted pyridyl group having, on a ring, one to four substituents each independently selected from substituent group D;
(d21) a pyridazinyl group;
(d22) a substituted pyridazinyl group having, on a ring, one to three substituents each independently selected from substituent group D;
(d23) a pyrimidinyl group;
(d24) a substituted pyrimidinyl group having, on a ring, one to three substituents each independently selected from substituent group D;
(d25) a pyrazinyl group;
(d26) a substituted pyrazinyl group having, on a ring, one to three substituents each independently selected from substituent group D;
(d43) a pyrazolyl group; or
(d44) a substituted pyrazolyl group having, on a ring, one to three substituents each independently selected from substituent group D,
$R^5$ is
(e1) a $(C_1-C_6)$ alkyl group;
(e2) a $(C_2-C_6)$ alkenyl group;
(e3) a $(C_2-C_6)$ alkynyl group;
(e4) a $(C_3-C_6)$ cycloalkyl group;
(e5) a halo $(C_1-C_6)$ alkyl group;
(e6) a halo $(C_2-C_6)$ alkenyl group;
(e9) a substituted $(C_1-C_6)$ alkyl group having, on a chain, one to three substituents each independently selected from the group consisting of a cyano group, a $(C_1-C_6)$ alkoxy group, a $(C_3-C_6)$ cycloalkyl group, a $(C_1-C_6)$ alkylcarbonyl group, a $(C_3-C_6)$ cycloalkylcarbonyl group, a phenylcarbonyl group, a $(C_1-C_6)$ alkoxycarbonyl group, an aminocarbonyl group, a halo $(C_1-C_6)$ alkylcarbonyl group, a $(C_1-C_6)$ alkylsulfanyl group, a tri-$(C_1-C_6)$ alkylsilyl $(C_1-C_6)$ alkoxy group (wherein the $(C_1-C_6)$ alkyl groups are the same as or different from each other), and a tri-$(C_1-C_6)$ alkylsilyl group (wherein the $(C_1-C_6)$ alkyl groups are the same as or different from each other);
(e11) a phenyl $(C_1-C_6)$ alkyl group;
(e12) a substituted phenyl $(C_1-C_6)$ alkyl group having, on a ring, one to five substituents each independently selected from the group consisting of a halogen atom, a cyano group, a nitro group, a $(C_1-C_6)$ alkyl group, a $(C_1-C_6)$ alkoxy group, a halo $(C_1-C_6)$ alkyl group, a halo $(C_1-C_6)$ alkoxy group, a $(C_3-C_6)$ cycloalkyl group, a $(C_1-C_6)$ alkoxycarbonyl group, a $(C_1-C_6)$ alkylsulfanyl group, a $(C_1-C_6)$ alkylsulfinyl group, a $(C_1-C_6)$ alkylsulfonyl group, a halo $(C_1-C_6)$ alkylsulfanyl group, a diphenylamino group, a phenoxy group, and a methylenedioxy group formed by two adjacent substituents together;
(e13) a pyridyl $(C_1-C_6)$ alkyl group;
(e14) a substituted pyridyl $(C_1-C_6)$ alkyl group having, on a ring, one to four substituents each independently selected from the group consisting of a halogen atom, a cyano group, a nitro group, a $(C_1-C_6)$ alkyl group, a $(C_1-C_6)$ alkoxy group, a halo $(C_1-C_6)$ alkyl group, a halo $(C_1-C_6)$ alkoxy group, a $(C_1-C_6)$ alkoxycarbonyl group and a halo $(C_1-C_6)$ alkylsulfanyl group;
(e15) a thiazolyl $(C_1-C_6)$ alkyl group;
(e16) a substituted thiazolyl $(C_1-C_6)$ alkyl group having, on a ring, one or two substituents each independently selected from the group consisting of a halogen atom, a cyano group, a nitro group, a $(C_1-C_6)$ alkyl group, a $(C_1-C_6)$ alkoxy group, a halo $(C_1-C_6)$ alkyl group, a halo ($C_1$-$C_6$) alkoxy group, a ($C_1$-$C_6$) alkoxycarbonyl group and a halo ($C_1$-$C_6$) alkylsulfanyl group;
(e17) an oxadiazolyl ($C_1$-$C_6$) alkyl group;
(e18) a substituted oxadiazolyl ($C_1$-$C_6$) alkyl group having a pyridyl group on a ring;
(e19) a naphthyl ($C_1$-$C_6$) alkyl group;
(e20) a substituted naphthyl ($C_1$-$C_6$) alkyl group having, on a ring, one to seven substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e21) a quinolinyl ($C_1$-$C_6$) alkyl group;
(e22) a substituted quinolinyl ($C_1$-$C_6$) alkyl group having, on a ring, one to six substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e23) a thienyl ($C_1$-$C_6$) alkyl group;
(e24) a substituted thienyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e25) a pyrazolyl ($C_1$-$C_6$) alkyl group;
(e26) a substituted pyrazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e27) an oxazolyl ($C_1$-$C_6$) alkyl group;
(e28) a substituted oxazolyl ($C_1$-$C_6$) alkyl group having, on a ring, one or two substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e29) an imidazolyl ($C_1$-$C_6$) alkyl group;
(e30) a substituted imidazolyl ($C_1$-$C_6$) alkyl group having, on a ring, one to three substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e31) a pyridyl group;
(e32) a substituted pyridyl group having, on a ring, one to four substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e33) a phenyl group;
(e34) a substituted phenyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_1$-$C_6$) alkoxycarbonyl group and a halo ($C_1$-$C_6$) alkylsulfanyl group;
(e35) a ($C_1$-$C_6$) alkylcarbonyl group; or
(e36) a hydrogen atom,
$R^3$ and $R^5$ are optionally bonded to each other to form a 5- or 6-membered ring,
Y is an oxygen atom or $NR^6$ (wherein $R^6$ represents a hydrogen atom, a cyano group, a ($C_1$-$C_6$) alkyl group, a ($C_3$-$C_6$) cycloalkyl group, a halo ($C_1$-$C_6$) alkyl group, a ($C_1$-$C_6$) alkylcarbonyl group, a halo ($C_1$-$C_6$) alkylcarbonyl group, a ($C_1$-$C_6$) alkoxycarbonyl group, a phenylsulfonyl group, or a phenylsulfonyl group having, on a ring, one to five substituents each independently selected from the group consisting of a halogen atom, a cyano group, and a ($C_1$-$C_6$) alkyl group),
m is 0 or 1,
n is 0 or 1,
substituent group A consists of
(f1) a halogen atom;
(f2) a cyano group;
(f6) a ($C_1$-$C_6$) alkyl group;
(f9) a ($C_1$-$C_6$) alkoxy group;
(f10) a ($C_3$-$C_6$) cycloalkyl group;
(f11) a ($C_1$-$C_6$) alkylsulfanyl group;
(f14) a halo ($C_1$-$C_6$) alkyl group;
(f17) a halo ($C_1$-$C_6$) alkoxy group;
(f22) a N,N-di-($C_1$-$C_6$) alkylaminosulfonyl group (wherein the ($C_1$-$C_6$) alkyl moieties are the same as or different from each other);
(f59) a tetrazolyl group;
(f60) a substituted tetrazolyl group having, on a ring, one substituent each independently selected from the group consisting of a halogen atom, a cyano group, a ($C_1$-$C_6$) alkyl group, a ($C_1$-$C_6$) alkoxy group, a halo ($C_1$-$C_6$) alkyl group and a halo ($C_1$-$C_6$) alkoxy group; and
(f94) an aminocarbonyl group,
substituent group B consists of
(g1) a cyano group;
(g2) a ($C_3$-$C_6$) cycloalkyl group;
(g3) a ($C_1$-$C_6$) alkoxy group; and
(g4) a ($C_1$-$C_6$) alkylsulfanyl group,
substituent group C consists of
(h1) a cyano group;
(h2) a ($C_1$-$C_6$) alkyl group; and
(h10) a halo ($C_1$-$C_6$) alkyl group, and
substituent group D consists of
(i1) a halogen atom;
(i2) a cyano group;
(i7) a ($C_1$-$C_6$) alkyl group;
(i8) a ($C_1$-$C_6$) alkoxy group;
(i9) a ($C_3$-$C_6$) cycloalkyl group;
(i10) a ($C_1$-$C_6$) alkylsulfanyl group;
(i13) a halo ($C_1$-$C_6$) alkyl group;
(i14) a halo ($C_1$-$C_6$) alkoxy group;
(i15) a halo ($C_3$-$C_6$) cycloalkyl group;
(i19) a ($C_1$-$C_6$) alkoxycarbonyl group; and
(i25) a methylenedioxy group formed by two adjacent substituents together and optionally substituted by one or two substituents each selected from the group consisting of a halogen atom, a phenyl group and a ($C_1$-$C_6$) alkyl group.

4. The compound according to claim 1 or a salt thereof, wherein
$R^1$ is
(a1) a hydrogen atom;
(a2) a ($C_1$-$C_6$) alkyl group;
(a6) a halo ($C_1$-$C_6$) alkyl group;

(a9) a substituted ($C_1$-$C_6$) alkyl group having, on a chain, one to three substituents each independently selected from the group consisting of a cyano group, a ($C_1$-$C_6$) alkoxy group and a ($C_3$-$C_6$) cycloalkyl group;
(a13) a ($C_3$-$C_6$) cycloalkylcarbonyl group;
(a22) a ($C_1$-$C_6$) alkoxycarbonyl group;
(a24) a ($C_1$-$C_6$) alkoxy ($C_1$-$C_6$) alkoxycarbonyl group;
(a35) a N—($C_1$-$C_6$) alkylaminocarbonyl group;
(a52) a ($C_1$-$C_6$) alkylsulfonyl group;
(a82) a phenyl ($C_1$-$C_6$) alkyl group; or
(a85') a substituted thiazolyl ($C_1$-$C_6$) alkyl group having, on a ring, one or two substituents each independently selected from the group consisting of a halogen atom,
$R^2$ is
(b5) a phenyl group;
(b6) a substituted phenyl group having, on a ring, one to five substituents each independently selected from substituent group A;
(b7) a pyridyl group;
(b8) a substituted pyridyl group having, on a ring, one to four substituents each independently selected from substituent group A;
(b10) a substituted pyridazinyl group having, on a ring, one to three substituents each independently selected from substituent group A; or
(b12) a substituted pyrimidinyl group having, on a ring, one to three substituents each independently selected from substituent group A,
$R^3$ is
(c1) a hydrogen atom;
(c2) a ($C_1$-$C_6$) alkyl group;
(c5) a ($C_1$-$C_6$) alkylcarbonyl group; or
(c6) a ($C_1$-$C_6$) alkoxycarbonyl group,
$R^4$ is
(d4) a ($C_3$-$C_6$) cycloalkyl group;
(d17) a phenyl group;
(d18) a substituted phenyl group having, on a ring, one to five substituents each independently selected from substituent group D;
(d20) a substituted pyridyl group having, on a ring, one to four substituents each independently selected from substituent group D; or
(d44) a substituted pyrazolyl group having, on a ring, one to three substituents each independently selected from substituent group D,
$R^5$ is
(e1) a ($C_1$-$C_6$) alkyl group;
(e2) a ($C_2$-$C_6$) alkenyl group;
(e5) a halo ($C_1$-$C_6$) alkyl group;
(e9') a substituted ($C_1$-$C_6$) alkyl group having, on a chain, one to three substituents each independently selected from the group consisting of a cyano group, a ($C_1$-$C_6$) alkoxy group, a ($C_3$-$C_6$) cycloalkyl group, an aminocarbonyl group, a ($C_1$-$C_6$) alkylsulfanyl group, and a tri-($C_1$-$C_6$) alkylsilyl ($C_1$-$C_6$) alkoxy group (wherein the ($C_1$-$C_6$) alkyl groups are the same as or different from each other);

(e11) a phenyl ($C_1$-$C_6$) alkyl group;
(e12') a substituted phenyl ($C_1$-$C_6$) alkyl group having, on a ring, one to five substituents each independently selected from the group consisting of a halogen atom, a cyano group, a nitro group, a ($C_1$-$C_6$) alkyl group, a ($C_1$-$C_6$) alkoxy group, a halo ($C_1$-$C_6$) alkyl group, a halo ($C_1$-$C_6$) alkoxy group, a ($C_3$-$C_6$) cycloalkyl group, a ($C_1$-$C_6$) alkoxycarbonyl group, a ($C_1$-$C_6$) alkylsulfanyl group, a ($C_1$-$C_6$) alkylsulfonyl group, a halo ($C_1$-$C_6$) alkylsulfanyl group, and a diphenylamino group;
(e14') a substituted pyridyl ($C_1$-$C_6$) alkyl group having, on a ring, one to four substituents each independently selected from a halogen atom;
(e16') a substituted thiazolyl ($C_1$-$C_6$) alkyl group having, on a ring, one or two substituents each independently selected from a halogen atom;
(e18) a substituted oxadiazolyl ($C_1$-$C_6$) alkyl group having a pyridyl group on a ring;
(e19) a naphthyl ($C_1$-$C_6$) alkyl group;
(e21) a quinolinyl ($C_1$-$C_6$) alkyl group;
(e23) a thienyl ($C_1$-$C_6$) alkyl group;
(e27) an oxazolyl ($C_1$-$C_6$) alkyl group;
(e35) a ($C_1$-$C_6$) alkylcarbonyl group; or
(e36) a hydrogen atom,
$R^3$ and $R^5$ are optionally bonded to each other to form a 5- or 6-membered ring,
each of n and m is 0,
substituent group A consists of
(f1) a halogen atom;
(f2) a cyano group;
(f6) a ($C_1$-$C_6$) alkyl group;
(f9) a ($C_1$-$C_6$) alkoxy group;
(f11) a ($C_1$-$C_6$) alkylsulfanyl group;
(f14) a halo ($C_1$-$C_6$) alkyl group; and
(f94) an aminocarbonyl group, and
substituent group D consists of
(i1) a halogen atom;
(i2) a cyano group;
(i7) a ($C_1$-$C_6$) alkyl group;
(i8) a ($C_1$-$C_6$) alkoxy group;
(i10) a ($C_1$-$C_6$) alkylsulfanyl group;
(i14) a halo ($C_1$-$C_6$) alkoxy group; and
(i19) a ($C_1$-$C_6$) alkoxycarbonyl group.

5. An insecticidal agent comprising a compound according to claim 1 or a salt thereof as an active ingredient.

6. An agricultural and horticultural insecticidal agent comprising a compound according to claim 1 or a salt thereof as an active ingredient.

7. A method for using an insecticidal agent according to claim 5, comprising treating a plant or soil with an effective amount of the insecticidal agent.

* * * * *